(12) United States Patent
Moshe

(10) Patent No.: US 10,317,571 B2
(45) Date of Patent: Jun. 11, 2019

(54) REAL-TIME MONITORING, PARAMETRIC PROFILING, AND REGULATING CONTAMINATED OUTDOOR AIR PARTICULATE MATTER THROUGHOUT A REGION, VIA HYPER-SPECTRAL IMAGING AND ANALYSIS

(75) Inventor: Danny S. Moshe, Tel-Aviv (IL)

(73) Assignee: Green Vision Systems Ltd., Tel-Aviv (IL)

( * ) Notice: Subject to any disclaimer, the term of this patent is extended or adjusted under 35 U.S.C. 154(b) by 505 days.

(21) Appl. No.: 13/807,017

(22) PCT Filed: Jun. 28, 2011

(86) PCT No.: PCT/IL2011/000514
§ 371 (c)(1),
(2), (4) Date: Dec. 27, 2012

(87) PCT Pub. No.: WO2012/001686
PCT Pub. Date: Jan. 5, 2012

(65) Prior Publication Data
US 2013/0110400 A1 May 2, 2013

Related U.S. Application Data

(60) Provisional application No. 61/344,314, filed on Jun. 28, 2010, provisional application No. 61/411,224, filed on Nov. 8, 2010.

(51) Int. Cl.
*G01W 1/02* (2006.01)
*G01N 1/26* (2006.01)
(Continued)

(52) U.S. Cl.
CPC ............ *G01W 1/02* (2013.01); *G01N 1/26* (2013.01); *G01W 1/00* (2013.01);
(Continued)

(58) Field of Classification Search
CPC .... G01N 3/0264; G01N 3/2823; G01N 21/94; G01N 1/26; G01N 33/0075; G01N 1/2273; G01W 1/00; G06K 9/0063; G06K 9/2018
(Continued)

(56) References Cited

U.S. PATENT DOCUMENTS 5,323,317 A * 6/1994 Hampton ................. B64G 1/66
702/3
5,831,876 A 11/1998 Orr et al.
(Continued)

FOREIGN PATENT DOCUMENTS

| CN | 1619336 | 5/2005 |
| CN | 201110848 | 9/2008 |

(Continued)

OTHER PUBLICATIONS

Patent Examination Report dated Oct. 20, 2014 From the Australian Government, IP Australia Re. Application No. 2011272910.
(Continued)

*Primary Examiner* — John E Breene
*Assistant Examiner* — Jeffrey P Aiello

(57) ABSTRACT

Real-time monitoring, parametric profiling, and regulating contaminated outdoor air particulate matter throughout a region, via hyper-spectral imaging and analysis. Includes: (12) real-time sampling, and hyper-spectrally imaging and analyzing, contaminated outdoor air particulate matter, simultaneously at separate locations throughout the region, for generating local contaminated outdoor air particulate matter data-information packages; (14) real-time measuring outdoor weather-meteorological conditions, simultaneously at the locations, synchronized with the real-time sampling, imaging, and analyzing, for generating local outdoor weather-meteorological conditions data-information pack-
(Continued)

ages; (16, 18) real-time processing and analyzing the local data-information packages, for generating sets of local and regional geographical distribution parametric data-information profiles of contaminated outdoor air particulate matter, showing real-time local and regional geographical distributions of qualitative or/and quantitative parameters of contaminated outdoor air particulate matter, via a global data-information processing and communications unit. Particularly suitable for monitoring, profiling, maintaining, operating and controlling, developing, and planning, infrastructure and vehicular traffic, of human populated regions.

46 Claims, 16 Drawing Sheets

(51) Int. Cl.

| | |
|---|---|
| *G01W 1/00* | (2006.01) |
| *G01N 33/00* | (2006.01) |
| *G01N 1/02* | (2006.01) |
| *G01N 1/22* | (2006.01) |

(52) U.S. Cl.
CPC ... *G01N 33/0075* (2013.01); *G01N 2001/021* (2013.01); *G01N 2001/2223* (2013.01); *Y02A 90/14* (2018.01)

(58) Field of Classification Search
USPC ..... 340/539.11, 539.28, 539.13; 702/1, 3, 4, 702/189, 183; 73/31.01, 31.02, 863.31; 435/309.1
See application file for complete search history.

(56) References Cited

U.S. PATENT DOCUMENTS

| | | | | |
|---|---|---|---|---|
| 5,880,830 | A | 3/1999 | Schechter | |
| 6,114,964 | A * | 9/2000 | Fasano | G01N 33/0075 340/628 |
| 6,275,774 | B1 * | 8/2001 | Baron et al. | 702/3 |
| 6,563,452 | B1 * | 5/2003 | Zheng | G01S 7/003 342/195 |
| 6,941,806 | B2 * | 9/2005 | Burns | G01N 1/26 73/170.01 |
| 7,006,923 | B1 * | 2/2006 | Rubin | G01N 15/1463 702/19 |
| 7,149,366 | B1 | 12/2006 | Sun | |
| 7,184,891 | B1 | 2/2007 | Kuleszynski et al. | |
| 7,349,076 | B2 * | 3/2008 | Yao | 356/72 |
| 7,411,682 | B2 * | 8/2008 | Moshe | 356/452 |
| 7,847,708 | B1 * | 12/2010 | Jones et al. | 340/905 |
| 7,949,548 | B2 * | 5/2011 | Mathai et al. | 705/4 |
| 8,264,345 | B2 * | 9/2012 | Baron et al. | 340/539.3 |
| 8,595,020 | B2 * | 11/2013 | Marino | G01N 21/3504 23/314 |
| 9,002,113 | B2 * | 4/2015 | Moshe | 382/191 |
| 2002/0186137 | A1 * | 12/2002 | Skardon | 340/573.1 |
| 2005/0104771 | A1 * | 5/2005 | Terry et al. | 342/195 |
| 2008/0040041 | A1 | 2/2008 | Kilgus | |
| 2008/0304752 | A1 * | 12/2008 | Matteoni | G01N 1/2214 382/209 |
| 2009/0095054 | A1 * | 4/2009 | Groves | G01N 1/2273 73/31.01 |
| 2009/0210447 | A1 | 8/2009 | Moshe | |
| 2009/0309744 | A1 | 12/2009 | Fu et al. | |
| 2010/0028859 | A1 * | 2/2010 | Moshe et al. | 435/5 |
| 2011/0052019 | A1 * | 3/2011 | Moshe | 382/128 |
| 2011/0295575 | A1 * | 12/2011 | Levine | G06Q 30/02 703/2 |

FOREIGN PATENT DOCUMENTS

| | | |
|---|---|---|
| EP | 1191355 | 3/2002 |
| EP | 2199790 | 6/2010 |
| JP | 2003-208686 | 7/2003 |
| JP | 2004-170112 | 6/2004 |
| JP | 2006-133121 | 5/2006 |
| JP | 2010-032379 | 2/2010 |
| WO | WO 2009/034296 | 3/2009 |

OTHER PUBLICATIONS

Communication Pursuant to Article 94(3) EPC dated Sep. 22, 2014 From the European Patent Office Re. Application No. 11749550.7.
International Search Report and the Written Opinion dated Oct. 17, 2011 From the International Searching Authority Re. Application No. PCT/IL2011/000514.
Baklanov et al. "Potential and Shortcomings of Numerical Weather Prediction Models in Providing Meteorological Data for Urban Air Pollution Forecasting", Water, Air and Soil Pollution: Focus, XP055008841, 2(5/6): 43-60, Jan. 1, 2002.
San Jose et al. "Real-Time Air Quality Operational Forecasting Systems in Spain: An Application of the MM5-CMAQ-EMIMO Modelling System", Fisica de la Tierra, XP055008829, 19: 73-86, Jun. 20, 2007.
International Preliminary Report on Patentability dated Jan. 10, 2013 From the International Bureau of WIPO Re. Application No. PCT/IL2011/000514.
Notification of Office Action and Search Report dated Oct. 10, 2014 From the State Intellectual Property Office of the People's Republic of China Re. Application No. 201180037358.6.
Notification of Reason for Refusal dated Jun. 23, 2015 From the Japanese Patent Office Re. Application No. 2013-517671 and Its Translation Into English.
Office Action dated Jul. 19, 2016 From the Israel Patent Office Re. Application No. 223984 and Its Translation Into English.
Examination Report Under Sections 12 & 13 of the Patents Act, 1970 and the Patents Rules, 2003 dated Dec. 6, 2017 From the Government of India, Intellectual Property India, Patents, Designs, Trade Marks, Geographical Indications Re. Application No. 93/MUMNP/2013. (7 Pages).

* cited by examiner

12 [ Real-time sampling and hyper-spectral imaging, analyzing the contaminated outdoor air particulate matter. ]

(a) Real-time sampling, and hyper-spectrally imaging and analyzing, the contaminated outdoor air particulate matter, separately and simultaneously at each of a plurality of separate locations throughout the region, for generating a corresponding plurality of real-time local contaminated outdoor air particulate matter data-information packages each associated with a separate location.

⇩

14 [ Real-time (synchronously) measuring outdoor weather conditions of the contaminated outdoor air particulate matter. ]

(b) Real-time measuring outdoor weather-meteorological conditions, separately and simultaneously at the plurality of separate locations, in a manner synchronized with the real-time sampling, imaging, and analyzing, for generating a corresponding plurality of real-time local outdoor weather-meteorological conditions data-information packages each associated with a separate location.

⇩

16 [ Real-time processing/analyzing the real-time local data-information packages. ]

(c) Real-time processing and analyzing the real-time local contaminated outdoor air particulate matter data-information packages and the real-time local outdoor weather-meteorological conditions data-information packages, for real-time generating a set of real-time local geographical distribution parametric data-information profiles of the contaminated outdoor air particulate matter, showing real-time local geographical distributions of qualitative or/and quantitative parameters of contaminated outdoor air particulate matter of each location.

⇩

18 [ Real-time processing/analyzing the real-time local geographical distribution parametric data-information profiles. ]

(d) Real-time processing and analyzing the set of real-time local geographical distribution parametric data-information profiles of the contaminated outdoor air particulate matter, for real-time generating a set of real-time regional geographical distribution parametric data-information profiles of the contaminated outdoor air particulate matter, showing real-time regional geographical distributions of the qualitative or/and quantitative parameters of the contaminated outdoor air particulate matter throughout the region.

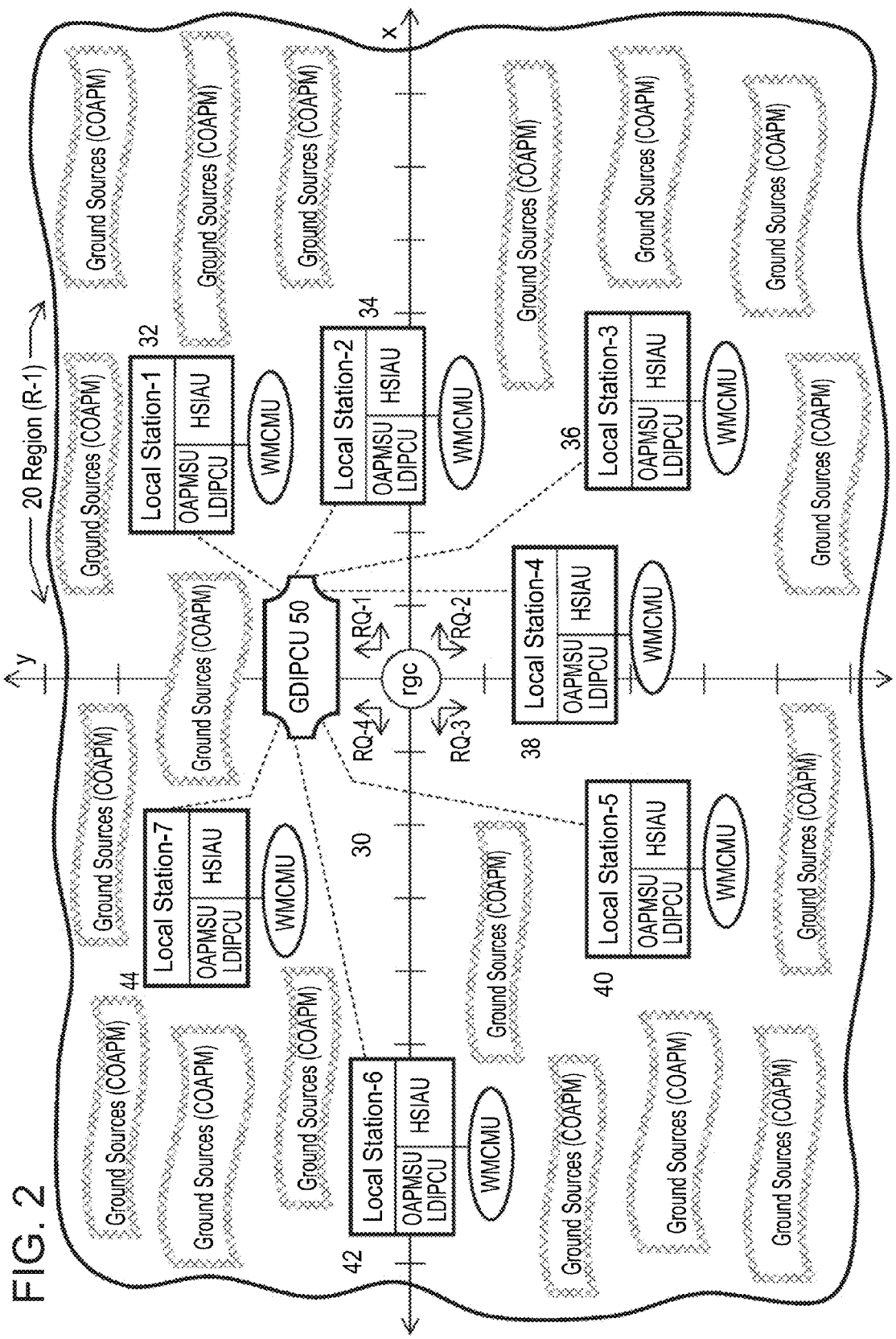

260 [ second type ground source (COAPM), at *first* test time (t = t1)]

402 [ Identifying and classifying ground sources of the contaminated outdoor air particulate matter, throughout the region. ]

| (a) | Identifying and classifying ground sources of the contaminated outdoor air particulate matter, for generating data-information of identified and classified ground sources of contaminated outdoor air particulate matter in the region. |
|---|---|

404 [ Real-time sampling and hyper-spectral imaging, analyzing the contaminated outdoor air particulate matter. ]

| (b) | Real-time sampling, and hyper-spectrally imaging and analyzing, the contaminated outdoor air particulate matter, separately and simultaneously at each of a plurality of separate locations throughout the region, for generating a corresponding plurality of real-time local contaminated outdoor air particulate matter data-information packages each associated with a separate location. |
|---|---|

406 [ Real-time (synchronously) measuring outdoor weather conditions of the outdoor air particulate matter. ]

| (c) | Real-time measuring outdoor weather-meteorological conditions, separately and simultaneously at the plurality of separate locations, in a manner synchronized with the real-time sampling, imaging, and analyzing, for generating a corresponding plurality of real-time local outdoor weather-meteorological conditions data-information packages each associated with a separate location. |
|---|---|

408 [ Real-time processing/analyzing the real-time local data-information packages. ]

| (d) | Real-time processing and analyzing the real-time local contaminated outdoor air particulate matter data-information packages and the real-time local outdoor weather-meteorological conditions data-information packages, for real-time generating a set of real-time local geographical distribution parametric data-information profiles of the contaminated outdoor air particulate matter, showing real-time local geographical distributions of qualitative or/and quantitative parameters of the contaminated outdoor air particulate matter of each location. |
|---|---|

400  FIG. 15B

410 [ Real-time processing/analyzing the set of real-time local geographical distribution parametric data-information profiles. ]

| | |
|---|---|
| (e) | Real-time processing and analyzing the set of real-time local geographical distribution parametric data-information profiles of the contaminated outdoor air particulate matter, for real-time generating a set of real-time regional geographical distribution parametric data-information profiles of the contaminated outdoor air particulate matter, showing real-time regional geographical distributions of the qualitative or/and quantitative parameters of the contaminated outdoor air particulate matter throughout the region. |

⇩

412 [ Real-time processing/analyzing the set of real-time regional geographical distribution parametric data-information profiles. ]

| | |
|---|---|
| (f) | Real-time processing and analyzing the set of real-time regional geographical distribution parametric data-information profiles of the contaminated outdoor air particulate matter, in relation to the data-information of the identified and classified ground sources of the contaminated air particulate matter, for determining at least one indication of needing to change operating conditions and contaminated air output of one or more of the ground sources. |

⇩

414 [ Real-time communicating the indication to the ground sources of the contaminated outdoor air particulate matter. ]

| | |
|---|---|
| (g) | Real-time communicating the at least one indication to an operator or controller of each of the one or more ground sources of the contaminated outdoor air particulate matter. |

⇩

416 [ Real-time changing outdoor air particulate matter output of one or more air particulate matter ground sources, in response to the indication. ]

| | |
|---|---|
| (h) | Real-time changing, in a controlled manner, the operating conditions and contaminated air output of the one or more ground sources, by each operator or controller, in response to the at least one indication, thereby regulating the contaminated outdoor air particulate matter throughout the region. |

REAL-TIME MONITORING, PARAMETRIC PROFILING, AND REGULATING CONTAMINATED OUTDOOR AIR PARTICULATE MATTER THROUGHOUT A REGION, VIA HYPER-SPECTRAL IMAGING AND ANALYSIS

RELATED APPLICATIONS

This application is a National Phase of PCT Patent Application No. PCT/IL2011/000514 having International filing date of Jun. 28, 2011, which claims the benefit of priority under 35 USC § 119(e) of U.S. Provisional Patent Application Nos. 61/344,314 filed on Jun. 28, 2010 and 61/411,224 filed on Nov. 8, 2010. The contents of the above applications are all incorporated by reference as if fully set forth herein in their entirety.

FIELD OF THE INVENTION

The present invention relates to monitoring, parametric profiling, and regulating contaminated outdoor air particulate matter throughout a region, and more particularly, but not exclusively, to real-time monitoring, parametric profiling, and regulating contaminated outdoor air particulate matter throughout a region, via hyper-spectral imaging and analysis.

Exemplary embodiments of the present invention are particularly applicable to those fields and areas of technology which are based on, or/and, involve monitoring, profiling, maintaining, controlling, and providing public health information and advisories about, outdoor air quality of human populated regions. Exemplary embodiments are especially applicable to urban (city) regions wherein there co-exist large sized, densely located human populations with large numbers of densely located ground sources of contaminated outdoor air particulate matter. Exemplary categories of such ground sources are: (1) actively used and operative infrastructure type ground sources, such as industrial, commercial, business, public, private, and residential, entities (building and building-like structures, especially, factories, manufacturing plants, power [coal and oil burning] plants, homes, food making and cooking establishments), and, vehicular roadways, bridges, and tunnels; (2) actively used and operative vehicular traffic type ground sources, such as automobiles, buses, trucks, vans, motorbikes, and scooters; and (3) plant matter and ground surface type ground sources, such as trees, bushes, shrubs, plants, flowers, grass, and soil. Such ground sources are (directly or/and indirectly) operable and controllable via human or/and machine type operators or/and controllers. Exemplary embodiments of the present invention are particularly suitable for applications which are based on, or/and, involve monitoring, profiling, maintaining, operating and controlling, developing, and planning, infrastructure and vehicular traffic, of human populated regions, where such applications include the important objective of achieving and maintaining high quality levels of outdoor air of the human populated regions, which, in turn, contributes to achieving and maintaining high quality levels of public health, welfare, and activities throughout the human populated regions.

BACKGROUND OF THE INVENTION

'Outdoor air' generally refers to air which is located outdoors (out-of-doors) or outside of (typically, automatically or/and manually climate controllable) closed types of structural entities (i.e., buildings), and which is normally, continuously breathed in by humans on a daily basis, among the myriad of other ways in which outdoor air is used or/and consumed. 'Outdoor air particulate matter' generally refers to essentially any type(s) or kind(s), size(s), and quantity(ies), and, ranges and distributions thereof, of matter being in particulate (or particulate-like) (solid phase) form, which is present in or throughout outdoor air. Such particulate (or particulate-like) matter is considered as being 'airborne' (i.e., moved or conveyed by or through air). Such particulate (or particulate-like) matter is composed or made up of essentially any type(s) or kind(s), size(s), and quantity(ies), and, ranges and distributions thereof, of inorganic or/and organic material(s) or substance(s). Such particulate (or particulate-like) matter is either visible (macro-sized) or invisible (micro-sized) to the naked eye. A well known and commonly used convention for characterizing the size of such particulate (or particulate-like) matter is based on the particulate (or particulate-like) matter having a characteristic diameter (such as an average or longest diameter) of less than a specified magnitude, for example, less than 2.5 microns (fine particulate matter), or less than 10 microns (course particulate matter), being referred to by the terms '$PM_{2.5}$', and '$PM_{10}$', respectively.

'Contaminated (polluted) outdoor air particulate matter' generally refers to outdoor air particulate matter (as described above) which, by itself is at least one type or kind, and form, of contaminant (pollutant), or/and is contaminated (polluted) by (i.e., includes) at least one type or kind, and form, of contaminant (pollutant). Alternatively stated, there are two 'main' cases, and a third 'combination' case thereof, of 'contaminated outdoor air particulate matter'. Namely, in the first main case, the outdoor air particulate matter is by itself at least one type or kind, and form, of contaminant, and is therefore, contaminated outdoor air particulate matter. In the second main case, the outdoor air particulate matter is not by itself a contaminant, rather, the outdoor air particulate matter is contaminated by (i.e., includes) at least one type or kind, and form, of contaminant, and is therefore, contaminated outdoor air particulate matter. In the third 'combination' case, the outdoor air particulate matter includes (is composed of) both the first and second main cases of contaminated outdoor air particulate matter.

A 'contaminant (pollutant)' generally refers to essentially any type(s) or kind(s), form(s), size(s), and quantity(ies), and, ranges and distributions thereof, of matter that, when a human (internally or/and externally) contacts (is exposed to) sufficient quantity(ies) or/and duration(s) thereof, such matter is considered (i.e., either known or suspected) as being, or potentially being, problematic, hazardous, or harmful to human health and well being.

For the case of outdoor air particulate matter itself not being at least one type or kind, and form, of contaminant, then, such outdoor air particular matter is contaminated by at least one type or kind, and form, of contaminant as a result of one or more physicochemical interaction mechanisms (such as physical or/and chemical absorption or/and adsorption) existing between the outdoor air particulate matter and the at least one contaminant, whereby the at least one contaminant is physically or/and chemically absorbed or/and adsorbed on or/and within the outdoor air particulate matter. In such a case, the outdoor air particulate matter serves as the mobile medium or carrier (transporter, conveyor) of the at least one contaminant.

For either case of the outdoor air particulate matter itself being at least one contaminant, or, being contaminated by (i.e., including) at least one contaminant, or, being a combination thereof, then, in view and by extension of the preceding description, 'contaminated outdoor air particulate matter' generally refers to matter that, when a human (internally or/and externally) contacts (is exposed to) sufficient quantity(ies) or/and duration(s) thereof, such matter is considered (i.e., either known or suspected) as being, or potentially being, problematic, hazardous, or harmful to human health and well being. Such human (internal or/and external) contact with (exposure to) contaminated outdoor air particulate matter is generally effected by normal human air-breathing mechanisms (i.e., via nasal passageways or/and skin pores), and by normal human air-contacting (exposure) mechanisms (i.e., direct contact (exposure) of non-porous areas of skin to air).

A direct result and consequence of contaminated outdoor air particulate matter, considered (i.e., either known or suspected) as being, or potentially being, problematic, hazardous, or harmful to human health and well being, is the need for monitoring, parametric profiling, and regulating contaminated outdoor air particulate matter throughout regions populated by humans. Such is especially the case for fulfilling the important objective of achieving and maintaining high quality levels of outdoor air of the human populated regions, which, in turn, contributes to achieving and maintaining high quality levels of public health, welfare, and activities throughout the human populated regions.

Monitoring, parametric profiling, and regulating contaminated outdoor air particulate matter throughout a region involve the following three main aspects: (1) monitoring (tracking, checking, testing) the (contents or/and quality of the) contaminated outdoor air particulate matter throughout the region, (2) parametric profiling (characterizing, classifying, correlating) the (contents or/and quality of the) contaminated outdoor air particulate matter throughout the region, and (3) regulating (controlling, changing) the (contents or/and quality of the) contaminated outdoor air particulate matter throughout the region.

Teachings of or/and relating to monitoring, parametric profiling, and regulating contaminated outdoor air particulate matter throughout a region, and of related or/and associated subjects and applications thereof (such as monitoring, parametric profiling, and regulating outdoor air, or/and contaminated (polluted) outdoor air), are well known and taught about in scientific, technical, and patent, literature, and currently practiced in a wide variety of numerous different fields and areas of technology.

There exists teachings and practices of a wide variety of different analytical methods and techniques, and associated analytical equipment, instrumentation, hardware, and software, which are suitable for on-line (real time, near-real time) or off-line analysis of contaminated outdoor air or/and contaminated outdoor air particulate matter. Clearly, many factors, parameters, conditions, criteria, and requirements, are involved that need to be identified, analyzed, considered, accounted for, and possibly tested, in order to properly determine which particular analytical method or technique, and, associated analytical equipment, instrumentation, hardware, and software, are most suitable for analyzing a particular type or kind, form, and quantity, of contaminated outdoor air or/and contaminated outdoor air particulate matter.

Hyper-Spectral Imaging and Analysis

Hyper-spectral imaging and analysis has been established as a highly unique, specialized, and sophisticated, combined spectroscopy and imaging type of analytical method or technique, in the more encompassing field or area of analytical science and technology, involving the sciences and technologies of spectroscopy and imaging. By definition, hyper-spectral imaging and analysis is based on a combination of spectroscopy and imaging theories, principles, and practices, which are exploitable for analyzing and classifying various different types and kinds of samples of matter in a highly unique, specialized, and sophisticated, manner.

Hyper-spectral imaging, in general, generating and collecting hyper-spectral images, and, processing and analyzing hyper-spectral image data and information, in particular, theory, principles, and practices thereof, and, related and associated applications and subjects thereof, such as the more general subject of spectral imaging, are well known and taught about in scientific, technical, and patent, literature, and currently practiced in a wide variety of numerous different fields and areas of technology. Selected teachings and practices of hyper-spectral imaging and analysis by the same applicant/assignee of the present invention are disclosed in references 1-8 (and references cited therein).

In sharp contrast to the regular or standard spectroscopic imaging technique of 'spectral' imaging and analysis, the more highly specialized, complex, and sophisticated, spectroscopic imaging technique of 'hyper-spectral' imaging and analysis, consists of using a hyper-spectral imaging and analysis system for on-line (real time, near-real time) or off-line generating and collecting (acquiring) hyper-spectral images and spectra (herein, together, generally referred to as hyper-spectral image data and information), and, processing and analyzing the acquired hyper-spectral image data and information. In hyper-spectral imaging, multiple fields of view of an object (and components thereof) (for example, included in a sample of matter) is 'hyper-spectrally' scanned and imaged while the object (and components thereof) is exposed to electromagnetic radiation.

During the hyper-spectral scanning and imaging there is generating and collecting relatively large numbers (up to the order of millions) of multiple spectral (i.e., hyper-spectral) images, 'one-at-a-time', but, in an extremely fast or rapid sequential manner, of the objects (and components thereof) emitting electromagnetic radiation at a plurality of many wavelengths (or frequencies, or energies), where the wavelengths (or frequencies, or energies) are associated with different selected (relatively narrow) portions or bands, or bands therein, of an entire hyper-spectrum emitted by the objects (and components thereof). A hyper-spectral imaging and analysis system can be operated in an extremely fast or rapid manner for providing exceptionally highly resolved spectral and spatial data and information of an imaged object (and components thereof), with high accuracy and high precision (reproducibility), which are fundamentally unattainable by using a regular or standard spectral imaging and analysis system.

In general, when electromagnetic radiation, for example, in the form of light such as that supplied by the sun, or by a man-made imaging type of illuminating or energy source, such as that used during hyper-spectral imaging, is incident upon an object, the electromagnetic radiation is affected by one or more of the species or components making up the object, by any combination of electromagnetic radiation absorption, diffusion, reflection, diffraction, scattering, or/and transmission, mechanisms. Moreover, an object whose composition includes organic chemical species or components, ordinarily exhibits some degree or extent of fluorescent or/and phosphorescent properties, characteristics, and behavior, when illuminated by some type of electromagnetic radiation or light, such as ultra-violet (UV), visible (VIS), or infrared (IR), types of light. The affected electromagnetic radiation, in the form of diffused, reflected, diffracted, scattered, or/and transmitted, electromagnetic radiation emitted by, or/and emerging from, the object (and components thereof), is directly and uniquely related to, and can be correlated with, the physical, chemical, or/and biological properties, characteristics, and behavior, of the object, in general, and of the species or components making up the object, in particular, and therefore represents a spectral ('fingerprint' or 'signature') pattern type of identification and characterization of the object, which is directly applicable for analyzing and classifying the object.

Accordingly, hyper-spectral images generated by, and collected from, an object (and components thereof) are correlated with emission spectra of the object (and components thereof), where the emission spectra correspond to spectral representations in the form of spectral 'fingerprint' or 'signature' pattern types of identification and characterization, of the hyper-spectrally imaged object (and components thereof). Such hyper-spectral image data and information are processed and analyzed by using automatic pattern recognition (APR) or/and optical character recognition (OCR) types of hyper-spectral imaging data and information processing and analysis, for identifying, characterizing, or/and classifying, the physical, chemical, or/and biological properties, characteristics, and behavior, and, species or components, of the hyper-spectrally imaged object (and components thereof).

Teachings of or/and relating to monitoring, parametric profiling, and regulating contaminated outdoor air particulate matter throughout a region, include various different significant limitations, as well as theoretical or/and practical difficulties and complexities, so as to be impractical or/and economically unfeasible to implement, especially for commercial scale industrial applications. Accordingly, in view of such teachings, there is an on-going need for developing and practicing improved or/and new techniques for monitoring, parametric profiling, and regulating contaminated outdoor air particulate matter throughout a region. There is thus a need for, and it would be highly advantageous and useful to have an invention which includes various exemplary embodiments which can be implemented for real-time monitoring, parametric profiling, and regulating contaminated outdoor air particulate matter throughout a region, via hyper-spectral imaging and analysis.

SUMMARY OF THE INVENTION

The present invention relates to real-time monitoring, parametric profiling, and regulating contaminated outdoor air particulate matter throughout a region, via hyper-spectral imaging and analysis.

Exemplary embodiments of the present invention are particularly applicable to those fields and areas of technology which are based on, or/and, involve monitoring, profiling, maintaining, controlling, and providing public health information and advisories about, outdoor air quality of human populated regions. Exemplary embodiments are especially applicable to urban (city) regions wherein there co-exist large sized, densely located human populations with large numbers of densely located ground sources of contaminated outdoor air particulate matter. Exemplary categories of such ground sources are: (1) actively used and operative infrastructure type ground sources, such as industrial, commercial, business, public, private, and residential, entities (building and building-like structures, especially, factories, manufacturing plants, power [coal and oil burning] plants, homes, food making and cooking establishments), and, vehicular roadways, bridges, and tunnels; (2) actively used and operative vehicular traffic type ground sources, such as automobiles, buses, trucks, vans, motorbikes, and scooters; and (3) plant matter and ground surface type ground sources, such as trees, bushes, shrubs, plants, flowers, grass, and soil. Such ground sources are (directly or/and indirectly) operable and controllable via human or/and machine type operators or/and controllers. Exemplary embodiments of the present invention are particularly suitable for applications which are based on, or/and, involve monitoring, profiling, maintaining, operating and controlling, developing, and planning, infrastructure and vehicular traffic, of human populated regions, where such applications include the important objective of achieving and maintaining high quality levels of outdoor air of the human populated regions, which, in turn, contributes to achieving and maintaining high quality levels of public health, welfare, and activities throughout the human populated regions.

Exemplary embodiments of the present invention address and overcome at least some of the problems or/and limitations of teachings in the relevant fields and arts thereof.

According to a main aspect of some exemplary embodiments of the present invention, there is provided a method for real-time monitoring and parametric profiling contaminated outdoor air particulate matter throughout a region, via hyper-spectral imaging and analysis, the method comprising: (a) real-time sampling, and hyper-spectrally imaging and analyzing, the contaminated outdoor air particulate matter, separately and simultaneously at each of a plurality of separate locations throughout the region, for generating a corresponding plurality of real-time local contaminated outdoor air particulate matter data-information packages each associated with a separate location in the region; (b) real-time measuring outdoor weather-meteorological conditions, separately and simultaneously at the plurality of separate locations, in a manner synchronized with the real-time sampling, imaging, and analyzing, for generating a corresponding plurality of real-time local outdoor weather-meteorological conditions data-information packages each associated with a separate location; (c) real-time processing and analyzing the real-time local contaminated outdoor air particulate matter data-information packages and the real-time local outdoor weather-meteorological conditions data-information packages, for real-time generating a set of real-time local geographical distribution parametric data-information profiles of the contaminated outdoor air particulate matter, showing real-time local geographical distributions of qualitative or/and quantitative parameters of the contaminated outdoor air particulate matter associated with each separate location, via a global data-information processing and communications unit; and (d) real-time processing and analyzing the set of real-time local geographical distribution parametric data-information profiles of the contaminated outdoor air particulate matter, for real-time generating a set of real-time regional geographical distribution parametric data-information profiles of the contaminated outdoor air particulate matter, showing real-time regional geographical distributions of the qualitative or/and quantitative parameters of the contaminated outdoor air particulate matter throughout the region, via the global data-information processing and communications unit.

According to another main aspect of some exemplary embodiments of the present invention, there is provided a system for real-time monitoring and parametric profiling contaminated outdoor air particulate matter throughout a region, via hyper-spectral imaging and analysis, the system comprising: (a) a plurality of local contaminated outdoor air particulate matter monitoring, sampling, and data-information processing stations, configured for separately and simultaneously operating at a corresponding plurality of separate locations throughout the region, and for real-time sampling, and hyper-spectrally imaging and analyzing the contaminated outdoor air particulate matter, separately and simultaneously at the plurality of separate locations, for generating a corresponding plurality of real-time local contaminated outdoor air particulate matter data-information packages each associated with a separate location; (b) a plurality of local weather-meteorological conditions measuring units, configured for separately and simultaneously operating at the plurality of separate locations, and for real-time measuring weather-meteorological conditions, separately and simultaneously at the plurality of separate locations, in a manner synchronized with the real-time sampling, imaging, and analyzing, for generating a corresponding plurality of real-time local outdoor weather-meteorological conditions data-information packages each associated with a separate location; and (c) a global data-information processing and communications unit, configured for: (i) real-time processing and analyzing the real-time local contaminated outdoor air particulate matter data-information packages and the real-time local outdoor weather-meteorological conditions data-information packages, for real-time generating a set of real-time local geographical distribution parametric data-information profiles of the contaminated outdoor air particulate matter, showing real-time local geographical distributions of qualitative or/and quantitative parameters of the contaminated outdoor air particulate matter associated with each separate location; and (ii) real-time processing and analyzing the set of real-time local geographical distribution parametric data-information profiles of the contaminated outdoor air particulate matter, for real-time generating a set of real-time regional geographical distribution parametric data-information profiles of the contaminated outdoor air particulate matter, showing real-time regional geographical distributions of the qualitative or/and quantitative parameters of the contaminated outdoor air particulate matter throughout the region.

According to another main aspect of some exemplary embodiments of the present invention, there is provided a method for real-time monitoring and regulating contaminated outdoor air particulate matter throughout a region, via hyper-spectral imaging and analysis, the method comprising: (a) identifying and classifying ground sources of the contaminated outdoor air particulate matter, wherein the ground sources are located throughout the region, for generating data-information of identified and classified ground sources of the contaminated outdoor air particulate matter throughout the region; (b) real-time sampling, and hyper-spectrally imaging and analyzing, the contaminated outdoor air particulate matter, separately and simultaneously at each of a plurality of separate locations throughout the region, for generating a corresponding plurality of real-time local contaminated outdoor air particulate matter data-information packages each associated with a separate location; (c) real-time measuring outdoor weather-meteorological conditions, separately and simultaneously at the plurality of separate locations, in a manner synchronized with the real-time sampling, imaging, and analyzing, for generating a corresponding plurality of real-time local outdoor weather-meteorological conditions data-information packages each associated with a separate location; (d) real-time processing and analyzing the real-time local contaminated outdoor air particulate matter data-information packages and the real-time local outdoor weather-meteorological conditions data-information packages, for real-time generating a set of real-time local geographical distribution parametric data-information profiles of the contaminated outdoor air particulate matter, showing real-time local geographical distributions of qualitative or/and quantitative parameters of the contaminated outdoor air particulate matter associated with each separate location, via a global data-information processing and communications unit; (e) real-time processing and analyzing the set of real-time local geographical distribution parametric data-information profiles of the contaminated outdoor air particulate matter, for real-time generating a set of real-time regional geographical distribution parametric data-information profiles of the contaminated outdoor air particulate matter, showing real-time regional geographical distributions of the qualitative or/and quantitative parameters of the contaminated outdoor air particulate matter throughout the region, via the global data-information processing and communications unit; (f) real-time processing and analyzing the set of real-time regional geographical distribution parametric data-information profiles of the contaminated outdoor air particulate matter, in relation to the data-information of the identified and classified ground sources of the contaminated outdoor air particulate matter, for determining at least one indication of needing to change operating conditions and contaminated air output of one or more of the ground sources, via the global data-information processing and communications unit; (g) real-time communicating the at least one indication to an operator or/and controller of each of the one or more ground sources of the contaminated outdoor air particulate matter; and (h) real-time changing, in a controlled manner, the operating conditions and the contaminated air output of the one or more ground sources, by each operator or controller, in response to the at least one indication, thereby regulating the contaminated outdoor air particulate matter throughout the region.

According to another main aspect of some exemplary embodiments of the present invention, there is provided a system for real-time monitoring and regulating contaminated outdoor air particulate matter throughout a region, via hyper-spectral imaging and analysis, the system comprising: (a) a plurality of local contaminated outdoor air particulate matter monitoring, sampling, and data-information processing stations, configured for separate and simultaneous operation at a corresponding plurality of separate locations throughout the region, and for real-time sampling, and hyper-spectrally imaging and analyzing the contaminated outdoor air particulate matter, separately and simultaneously at the plurality of separate locations, for generating a corresponding plurality of real-time local contaminated outdoor air particulate matter data-information packages each associated with a separate location; (b) a plurality of local weather-meteorological conditions measuring units, configured for separate and simultaneous operation at the plurality of separate locations, and for real-time measuring weather-meteorological conditions, separately and simultaneously at the plurality of separate locations, in a manner synchronized with the real-time sampling, imaging, and analyzing, for generating a corresponding plurality of real-time local outdoor weather-meteorological conditions data-information packages each associated with a separate location; and (c) a global data-information processing and communications unit, configured for: (i) classifying identified ground sources of the contaminated outdoor air particulate matter, wherein the ground sources are located throughout the region, for generating data-information of identified and classified ground sources of the contaminated outdoor air particulate matter throughout the region; (ii) real-time processing and analyzing the real-time local contaminated outdoor air particulate matter data-information packages and the real-time local outdoor weather-meteorological conditions data-information packages, for real-time generating a set of real-time local geographical distribution parametric data-information profiles of the contaminated outdoor air particulate matter, showing real-time local geographical distributions of qualitative or/and quantitative parameters of the contaminated outdoor air particulate matter associated with each separate location; (iii) real-time processing and analyzing the set of real-time local geographical distribution parametric data-information profiles of the contaminated outdoor air particulate matter, for real-time generating a set of real-time regional geographical distribution parametric data-information profiles of the contaminated outdoor air particulate matter, showing real-time regional geographical distributions of the qualitative or/and quantitative parameters of the contaminated outdoor air particulate matter throughout the region; and (iv) real-time processing and analyzing the set of real-time regional geographical distribution parametric data-information profiles of the contaminated outdoor air particulate matter, in relation to the data-information of the identified and classified ground sources of the contaminated outdoor air particulate matter, for determining at least one indication of needing to change operating conditions and contaminated air output of one or more of the ground sources; and (d) communications equipment, configured for real-time communicating the at least one indication to an operator or/and controller of each of the one or more ground sources of the contaminated outdoor air particulate matter, in order for each operator or controller to real-time change, in a controlled manner, the operating conditions and contaminated air output thereof, in response to the at least one indication, thereby regulating the contaminated outdoor air particulate matter throughout the region.

According to exemplary embodiments of the present invention, the main steps of real-time processing and analyzing the real-time local contaminated outdoor air particulate matter data-information packages and the real-time local outdoor weather-meteorological conditions data-information packages, and, real-time processing and analyzing the set of real-time local geographical distribution parametric data-information profiles of the contaminated outdoor air particulate matter, can be performed by including the use of highly specific, 'additional' data-information processing and analyzing techniques or/and procedures, for the purpose of refining and improving the accuracy and precision (reproducibility) of the results generated by these main steps.

A first exemplary 'additional' data-information processing and analyzing technique or/and procedure is based on accounting for, and using, (continuously or periodically updated) real-time local (bottom-up [ground-air] type) inventory data and information of the exemplary categories of the ground sources of contaminated outdoor air particulate matter throughout the region, namely, of: (1) actively used and operative infrastructure type ground sources, such as industrial, commercial, business, public, private, and residential, entities (building and building-like structures, especially, factories, manufacturing plants, power [coal and oil burning] plants, homes, food making and cooking establishments), and, vehicular roadways, bridges, and tunnels; (2) actively used and operative vehicular traffic type ground sources, such as automobiles, buses, trucks, vans, motorbikes, and scooters; and (3) plant matter and ground surface type ground sources, such as trees, bushes, shrubs, plants, flowers, grass, and soil.

A second exemplary 'additional' data-information processing and analyzing technique or/and procedure is based on accounting for, and using, (continuously or periodically updated) real-time local (bottom-up [ground-air] type) inventory data and information of atmospheric gas content, particularly with respect to potential gas phase contaminants in the outdoor air, throughout the region.

According to exemplary embodiments of the present invention, the outdoor weather-meteorological conditions are selected from the group consisting of: (a) temperature; (b) humidity; (c) barometric pressure; (d) wind movement; (e) precipitation type, extent, and movement; and (f) clouds type, extent, and movement.

According to exemplary embodiments of the present invention, the real-time measuring outdoor weather-meteorological conditions is performed using a weather-meteorological conditions measuring unit configured and operative for detecting, measuring, acquiring, collecting, processing, analyzing, and generating, local weather-meteorological conditions data and information of outdoor air, at each separate location.

According to exemplary embodiments of the present invention, weather-meteorological conditions data and information of the real-time local outdoor weather-meteorological conditions data-information package are detected, measured, and acquired, by at least one of the following outdoor air parametric measuring apparatuses: (i) an outdoor air temperature measuring apparatus; (ii) an outdoor air humidity measuring apparatus; (iii) an outdoor air barometric pressure measuring apparatus; (iv) an outdoor air wind movement measuring apparatus; (v) an outdoor air precipitation type, extent, and movement measuring apparatus; and (vi) an outdoor air cloud type, extent, and movement measuring apparatus.

According to exemplary embodiments of the present invention, the real-time local outdoor weather-meteorological conditions data-information packages are sent from a local outdoor air weather-meteorological conditions measuring unit to a local data-information processing and communications unit which is operatively connected to and in communication with the global data-information processing and communications unit.

According to exemplary embodiments of the present invention, the real-time processing and analyzing the real-time local outdoor air particulate matter data-information packages and the real-time local outdoor weather-meteorological conditions data-information packages, is performed using: (1) bottom-up, ground to air, based data-information processing and analyzing techniques and procedures, or/and (2) top-down, air to ground, based data-information techniques and procedures.

According to exemplary embodiments of the present invention, there further includes a data-information processing and analyzing technique based on accounting for, and using, continuously or periodically updated real-time local bottom-up, ground to air, type inventory data and information of ground sources of the contaminated outdoor air particulate matter throughout the region.

According to exemplary embodiments of the present invention, there further includes a data-information processing and analyzing technique based on accounting for, and using, continuously or periodically updated real-time local bottom-up, ground to air, type inventory data and information of atmospheric gas content in outdoor air throughout the region.

According to exemplary embodiments of the present invention, there further includes correlating results obtained from using a data-information processing and analyzing technique based on accounting for, and using, continuously or periodically updated real-time local bottom-up, ground to air, type inventory data and information of ground sources of the contaminated outdoor air particulate matter throughout the region, with results obtained from using a data-information processing and analyzing technique based on accounting for, and using, continuously or periodically updated real-time local bottom-up, ground to air, type inventory data and information of atmospheric gas content in outdoor air throughout the region.

Exemplary embodiments of the present invention are implemented by performing steps or procedures, and sub-steps or sub-procedures, in a manner selected from the group consisting of manually, semi-automatically, fully automatically, and a combination thereof, involving use and operation of system units, system sub-units, devices, assemblies, sub-assemblies, mechanisms, structures, components, and elements, and, peripheral equipment, utilities, accessories, and materials. Moreover, according to actual steps or procedures, sub-steps or sub-procedures, system units, system sub-units, devices, assemblies, sub-assemblies, mechanisms, structures, components, and elements, and, peripheral equipment, utilities, accessories, and materials, used for implementing a particular embodiment of the disclosed invention, the steps or procedures, and sub-steps or sub-procedures, are performed by using hardware, software, or/and an integrated combination thereof, and the system units, sub-units, devices, assemblies, sub-assemblies, mechanisms, structures, components, and elements, and, peripheral equipment, utilities, accessories, and materials, operate by using hardware, software, or/and an integrated combination thereof.

For example, software used, via an operating system, for implementing exemplary embodiments of the present invention can include operatively interfaced, integrated, connected, or/and functioning written or/and printed data, in the form of software programs, software routines, software sub-routines, software symbolic languages, software code, software instructions or protocols, software algorithms, or a combination thereof. For example, hardware used for implementing exemplary embodiments of the present invention can include operatively interfaced, integrated, connected, or/and functioning electrical, electronic or/and electromechanical system units, sub-units, devices, assemblies, sub-assemblies, mechanisms, structures, components, and elements, and, peripheral equipment, utilities, accessories, and materials, which may include one or more computer chips, integrated circuits, electronic circuits, electronic sub-circuits, hard-wired electrical circuits, or a combination thereof, involving digital or/and analog operations. Exemplary embodiments of the present invention can be implemented by using an integrated combination of the just described exemplary software and hardware.

In exemplary embodiments of the present invention, steps or procedures, and sub-steps or sub-procedures, can be performed by a data processor, such as a computing platform, for executing a plurality of instructions. Optionally, the data processor includes volatile memory for storing instructions or/and data, or/and includes non-volatile storage, for example, a magnetic hard-disk or/and removable media, for storing instructions or/and data. Optionally, exemplary embodiments of the present invention include a network connection. Optionally, exemplary embodiments of the present invention include a display device and a user input device, such as a keyboard or/and 'mouse'.

BRIEF DESCRIPTION OF THE DRAWINGS

Exemplary embodiments of the present invention are herein described, by way of example only, with reference to the accompanying drawings. With specific reference now to the drawings in detail, it is stressed that the particulars shown are by way of example and for purposes of illustrative description of some embodiments of the present invention. In this regard, the description taken together with the accompanying drawings make apparent to those skilled in the art how exemplary embodiments of the present invention may be practiced. In the drawings:

FIG. 1 is a (block-type) flow diagram of an exemplary embodiment of the method for real-time monitoring and parametric profiling contaminated outdoor air particulate matter throughout a region, via hyper-spectral imaging and analysis, in accordance with the present invention;

FIG. 2 is a schematic diagram illustrating an exemplary embodiment of the system for real-time monitoring and parametric profiling contaminated outdoor air particulate matter throughout a region, via hyper-spectral imaging and analysis, shown for an exemplary region (R-1) with respect to an exemplary geographical direction and distance grid (x-y coordinate axis system), wherein the exemplary embodiment of the system is particularly suitable for implementing the exemplary embodiment of the method presented in FIG. 1, and for implementing the exemplary embodiment of the method presented in FIGS. 15A and 15B (below), in accordance with the present invention;

FIGS. 15A and 15B are (block-type) flow diagrams of [main steps (a)-(d), and main steps (e)-(h), respectively] of an exemplary embodiment of the method for real-time monitoring and regulating contaminated outdoor air particulate matter throughout a region, via hyper-spectral imaging and analysis, in accordance with the present invention.

DESCRIPTION OF SPECIFIC EMBODIMENTS OF THE INVENTION

Figure 3:
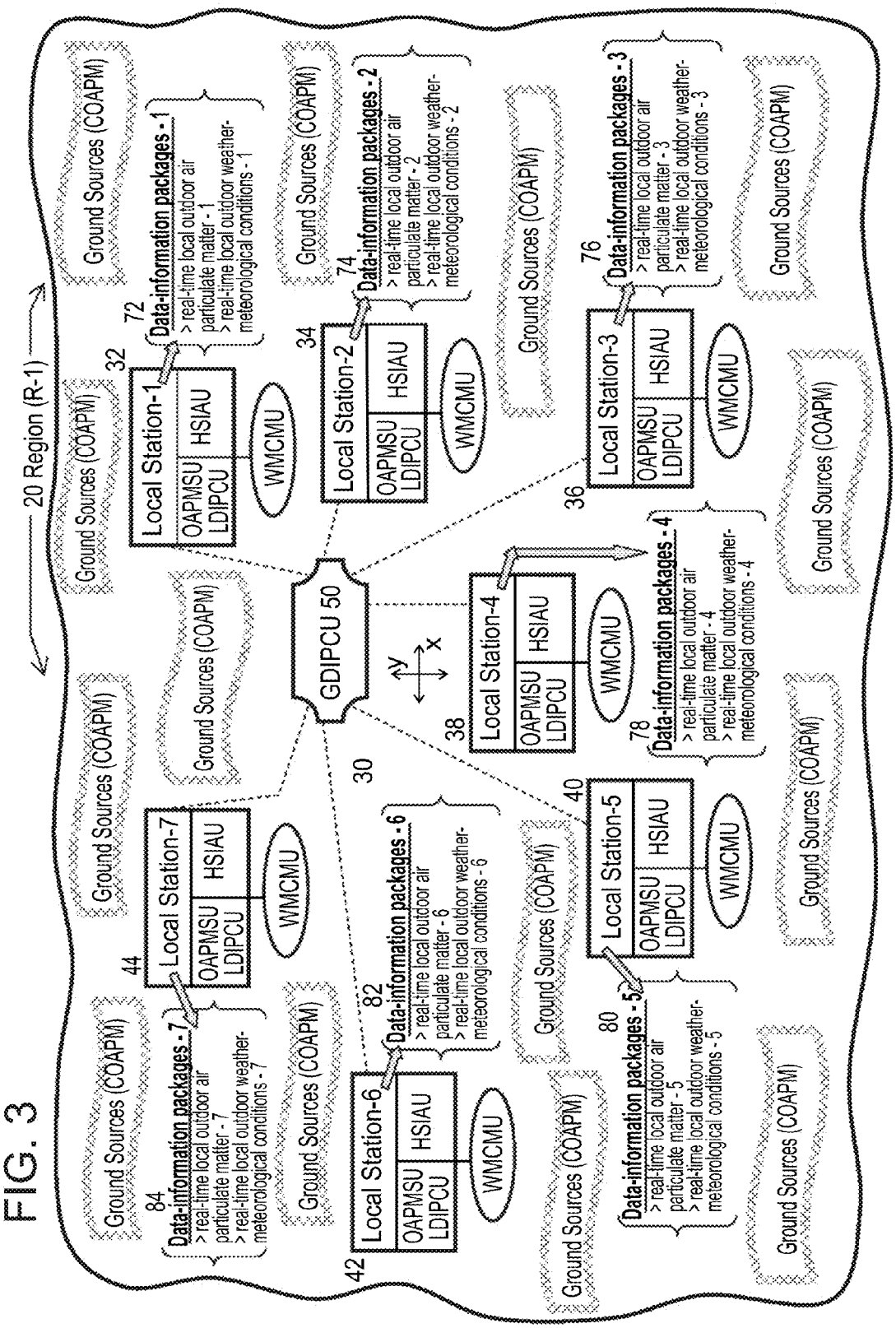
FIG. 3 is a schematic diagram illustrating the exemplary embodiment of the system presented in FIG. 2, particularly showing performance of main Steps (a) and (b) of the exemplary embodiment of the method presented in FIG. 1, in accordance with the present invention.

The present invention relates to real-time monitoring, parametric profiling, and regulating contaminated outdoor air particulate matter throughout a region, via hyper-spectral imaging and analysis.

Exemplary embodiments of the present invention are particularly applicable to those fields and areas of technology which are based on, or/and, involve monitoring, profiling, maintaining, controlling, and providing public health information and advisories about, outdoor air quality of human populated regions. Exemplary embodiments are especially applicable to urban (city) regions wherein there co-exist large sized, densely located human populations with large numbers of densely located ground sources of contaminated outdoor air particulate matter. Exemplary categories of such ground sources are: (1) actively used and operative infrastructure type ground sources, such as industrial, commercial, business, public, private, and residential, entities (essentially any building or building-like structure, especially, factories, manufacturing plants, power [coal and oil burning] plants, homes, food making and cooking establishments), and, vehicular roadways, bridges, and tunnels; (2) actively used and operative vehicular traffic type ground sources, such as automobiles, buses, trucks, vans, motorbikes, and scooters; and (3) plant matter and ground surface type ground sources, such as trees, bushes, shrubs, plants, flowers, grass, and soil. Such ground sources are (directly or/and indirectly) operable and controllable via human or/and machine type operators or/and controllers. Exemplary embodiments of the present invention are particularly suitable for applications which are based on, or/and, involve monitoring, profiling, maintaining, operating and controlling, developing, and planning, infrastructure and vehicular traffic, of human populated regions, where such applications include the important objective of achieving and maintaining high quality levels of outdoor air of the human populated regions, which, in turn, contributes to achieving and maintaining high quality levels of public health, welfare, and activities throughout the human populated regions.

A main aspect of some exemplary embodiments of the present invention is of a method for real-time monitoring and parametric profiling contaminated outdoor air particulate matter throughout a region, via hyper-spectral imaging and analysis.

An exemplary embodiment of such method includes the following main steps or procedures, and, components and functionalities thereof: (a) real-time sampling, and hyper-spectrally imaging and analyzing, the contaminated outdoor air particulate matter, separately and simultaneously at each of a plurality of separate locations throughout the region, for generating a corresponding plurality of real-time local contaminated outdoor air particulate matter data-information packages each associated with a separate location in the region; (b) real-time measuring outdoor weather-meteorological conditions, separately and simultaneously at the plurality of separate locations, in a manner synchronized with the real-time sampling, imaging, and analyzing, for generating a corresponding plurality of real-time local outdoor weather-meteorological conditions data-information packages each associated with a separate location; (c) real-time processing and analyzing the real-time local contaminated outdoor air particulate matter data-information packages and the real-time local outdoor weather-meteorological conditions data-information packages, for real-time generating a set of real-time local geographical distribution parametric data-information profiles of the contaminated outdoor air particulate matter, showing real-time local geographical distributions of qualitative or/and quantitative parameters of the contaminated outdoor air particulate matter associated with each separate location, via a global data-information processing and communications unit; and (d) real-time processing and analyzing the set of real-time local geographical distribution parametric data-information profiles of the contaminated outdoor air particulate matter, for real-time generating a set of real-time regional geographical distribution parametric data-information profiles of the contaminated outdoor air particulate matter, showing real-time regional geographical distributions of the qualitative or/and quantitative parameters of the contaminated outdoor air particulate matter throughout the region, via the global data-information processing and communications unit.

Another main aspect of some exemplary embodiments of the present invention is of a system for real-time monitoring and parametric profiling contaminated outdoor air particulate matter throughout a region, via hyper-spectral imaging and analysis.

An exemplary embodiment of such system includes the following main components and functionalities thereof: (a) a plurality of local contaminated outdoor air particulate matter monitoring, sampling, and data-information processing stations, configured for separately and simultaneously operating at a corresponding plurality of separate locations throughout the region, and for real-time sampling, and hyper-spectrally imaging and analyzing the contaminated outdoor air particulate matter, separately and simultaneously at the plurality of separate locations, for generating a corresponding plurality of real-time local contaminated outdoor air particulate matter data-information packages each associated with a separate location; (b) a plurality of local weather-meteorological conditions measuring units, configured for separately and simultaneously operating at the plurality of separate locations, and for real-time measuring weather-meteorological conditions, separately and simultaneously at the plurality of separate locations, in a manner synchronized with the real-time sampling, imaging, and analyzing, for generating a corresponding plurality of real-time local outdoor weather-meteorological conditions data-information packages each associated with a separate location; and (c) a global data-information processing and communications unit, configured for: (i) real-time processing and analyzing the real-time local contaminated outdoor air particulate matter data-information packages and the real-time local outdoor weather-meteorological conditions data-information packages, for real-time generating a set of real-time local geographical distribution parametric data-information profiles of the contaminated outdoor air particulate matter, showing real-time local geographical distributions of qualitative or/and quantitative parameters of the contaminated outdoor air particulate matter associated with each separate location; and (ii) real-time processing and analyzing the set of real-time local geographical distribution parametric data-information profiles of the contaminated outdoor air particulate matter, for real-time generating a set of real-time regional geographical distribution parametric data-information profiles of the contaminated outdoor air particulate matter, showing real-time regional geographical distributions of the qualitative or/and quantitative parameters of the contaminated outdoor air particulate matter throughout the region.

Another main aspect of some exemplary embodiments of the present invention is of a method for real-time monitoring and regulating contaminated outdoor air particulate matter throughout a region, via hyper-spectral imaging and analysis.

An exemplary embodiment of such method includes the following main steps or procedures, and, components and functionalities thereof: (a) identifying and classifying ground sources of the contaminated outdoor air particulate matter, wherein the ground sources are located throughout the region, for generating data-information of identified and classified ground sources of the contaminated outdoor air particulate matter throughout the region; (b) real-time sampling, and hyper-spectrally imaging and analyzing, the contaminated outdoor air particulate matter, separately and simultaneously at each of a plurality of separate locations throughout the region, for generating a corresponding plurality of real-time local contaminated outdoor air particulate matter data-information packages each associated with a separate location; (c) real-time measuring outdoor weather-meteorological conditions, separately and simultaneously at the plurality of separate locations, in a manner synchronized with the real-time sampling, imaging, and analyzing, for generating a corresponding plurality of real-time local outdoor weather-meteorological conditions data-information packages each associated with a separate location; (d) real-time processing and analyzing the real-time local contaminated outdoor air particulate matter data-information packages and the real-time local outdoor weather-meteorological conditions data-information packages, for real-time generating a set of real-time local geographical distribution parametric data-information profiles of the contaminated outdoor air particulate matter, showing real-time local geographical distributions of qualitative or/and quantitative parameters of the contaminated outdoor air particulate matter associated with each separate location, via a global data-information processing and communications unit; (e) real-time processing and analyzing the set of real-time local geographical distribution parametric data-information profiles of the contaminated outdoor air particulate matter, for real-time generating a set of real-time regional geographical distribution parametric data-information profiles of the contaminated outdoor air particulate matter, showing real-time regional geographical distributions of the qualitative or/and quantitative parameters of the contaminated outdoor air particulate matter throughout the region, via the global data-information processing and communications unit; (f) real-time processing and analyzing the set of real-time regional geographical distribution parametric data-information profiles of the contaminated outdoor air particulate matter, in relation to the data-information of the identified and classified ground sources of the contaminated outdoor air particulate matter, for determining at least one indication of needing to change operating conditions and contaminated air output of one or more of the ground sources, via the global data-information processing and communications unit; (g) real-time communicating the at least one indication to an operator or/and controller of each of the one or more ground sources of the contaminated outdoor air particulate matter; and (h) real-time changing, in a controlled manner, the operating conditions and the contaminated air output of the one or more ground sources, by each operator or controller, in response to the at least one indication, thereby regulating the contaminated outdoor air particulate matter throughout the region.

Another main aspect of some exemplary embodiments of the present invention is of a system for real-time monitoring and regulating contaminated outdoor air particulate matter throughout a region, via hyper-spectral imaging and analysis.

An exemplary embodiment of such system includes the following main components and functionalities thereof: (a) a plurality of local contaminated outdoor air particulate matter monitoring, sampling, and data-information processing stations, configured for separate and simultaneous operation at a corresponding plurality of separate locations throughout the region, and for real-time sampling, and hyper-spectrally imaging and analyzing the contaminated outdoor air particulate matter, separately and simultaneously at the plurality of separate locations, for generating a corresponding plurality of real-time local contaminated outdoor air particulate matter data-information packages each associated with a separate location; (b) a plurality of local weather-meteorological conditions measuring units, configured for separate and simultaneous operation at the plurality of separate locations, and for real-time measuring weather-meteorological conditions, separately and simultaneously at the plurality of separate locations, in a manner synchronized with the real-time sampling, imaging, and analyzing, for generating a corresponding plurality of real-time local outdoor weather-meteorological conditions data-information packages each associated with a separate location; and (c) a global data-information processing and communications unit, configured for: (i) classifying identified ground sources of the contaminated outdoor air particulate matter, wherein the ground sources are located throughout the region, for generating data-information of identified and classified ground sources of the contaminated outdoor air particulate matter throughout the region; (ii) real-time processing and analyzing the real-time local contaminated outdoor air particulate matter data-information packages and the real-time local outdoor weather-meteorological conditions data-information packages, for real-time generating a set of real-time local geographical distribution parametric data-information profiles of the contaminated outdoor air particulate matter, showing real-time local geographical distributions of qualitative or/and quantitative parameters of the contaminated outdoor air particulate matter associated with each separate location; (iii) real-time processing and analyzing the set of real-time local geographical distribution parametric data-information profiles of the contaminated outdoor air particulate matter, for real-time generating a set of real-time regional geographical distribution parametric data-information profiles of the contaminated outdoor air particulate matter, showing real-time regional geographical distributions of the qualitative or/and quantitative parameters of the contaminated outdoor air particulate matter throughout the region; and (iv) real-time processing and analyzing the set of real-time regional geographical distribution parametric data-information profiles of the contaminated outdoor air particulate matter, in relation to the data-information of the identified and classified ground sources of the contaminated outdoor air particulate matter, for determining at least one indication of needing to change operating conditions and contaminated air output of one or more of the ground sources; and (d) communications equipment, configured for real-time communicating the at least one indication to an operator or/and controller of each of the one or more ground sources of the contaminated outdoor air particulate matter, in order for each operator or controller to real-time change, in a controlled manner, the operating conditions and contaminated air output thereof, in response to the at least one indication, thereby regulating the contaminated outdoor air particulate matter throughout the region.

Exemplary embodiments of the present invention include several special technical features, and, aspects of novelty and inventiveness over teachings of monitoring, parametric profiling, and regulating contaminated outdoor air particulate matter throughout a region. Exemplary embodiments of the present invention address and overcome at least some of the problems or/and limitations of teachings in the relevant fields and arts thereof.

It is to be understood that the present invention is not limited in its application to the details of the order or sequence, and number, of steps or procedures, and sub-steps or sub-procedures, of operation or implementation of exemplary embodiments of the method, or to the details of type, composition, construction, arrangement, order, and number, of the system units, system sub-units, devices, assemblies, sub-assemblies, mechanisms, structures, components, elements, and configurations, and, peripheral equipment, utilities, accessories, and materials, of exemplary embodiments of the system, set forth in the following illustrative description, and accompanying drawings, unless otherwise specifically stated herein. The present invention can be practiced or implemented according to various other alternative embodiments and in various other alternative ways.

It is also to be understood that all technical and scientific words, terms, or/and phrases, used herein throughout the present disclosure have either the identical or similar meaning as commonly understood by one of ordinary skill in the art to which this invention belongs, unless otherwise specifically defined or stated herein. Phraseology, terminology, and, notation, employed herein throughout the present disclosure are for the purpose of description and should not be regarded as limiting. Moreover, all technical and scientific words, terms, or/and phrases, introduced, defined, described, or/and exemplified, in the above Field and Background sections, are equally or similarly applicable in the illustrative description of the embodiments, examples, and appended claims, of the present invention. Immediately following are selected definitions and exemplary usages of words, terms, or/and phrases, which are used throughout the illustrative description of the exemplary embodiments, examples, and appended claims, of the present invention, and are especially relevant for understanding thereof.

Each of the following terms written in singular grammatical form: 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', and 'an element', as used herein, may also refer to, and encompass, a plurality of units, a plurality of devices, a plurality of assemblies, a plurality of mechanisms, a plurality of components, and a plurality of elements, respectively.

Each of the following terms: 'includes', 'including', 'has', 'having', 'comprises', and 'comprising', and, their linguistic/grammatical variants, derivatives, or/and conjugates, as used herein, means 'including, but not limited to'.

The phrase 'operatively connected', as used herein, equivalently refers to the corresponding synonymous phrases 'operatively joined', or 'operatively attached', where the operative connection, operative joint, or operative attachment, is according to a physical, or/and electrical, or/and electronic, or/and mechanical, or/and electro-mechanical, manner or nature, involving various types and kinds of hardware or/and software equipment and components.

Outdoor Air

The phrase 'outdoor air', as used herein, generally refers to air which is located outdoors (out-of-doors) or outside of (typically, automatically or/and manually climate controllable) closed types of structural entities (i.e., buildings), and which is normally, continuously breathed in by humans on a daily basis, among the myriad of other ways in which outdoor air is used or/and consumed.

Outdoor Air Particulate Matter

The phrase 'outdoor air particulate matter', as used herein, generally refers to essentially any type(s) or kind(s), size(s), and quantity(ies), and, ranges and distributions thereof, of matter being in particulate (or particulate-like) (solid phase) form, which is present in or throughout outdoor air. Such particulate (or particulate-like) matter is considered as being 'airborne' (i.e., moved or conveyed by or through air). Such particulate (or particulate-like) matter is composed or made up of essentially any type(s) or kind(s), size(s), and quantity(ies), and, ranges and distributions thereof, of inorganic or/and organic material(s) or substance(s). Such particulate (or particulate-like) matter is either visible (macro-sized) or invisible (micro-sized) to the naked eye.

A well known and commonly used convention for characterizing the size of such particulate (or particulate-like) matter is based on the particulate (or particulate-like) matter having a characteristic diameter (such as an average diameter, or a longest diameter) of less than a specified magnitude, for example, less than 2.5 microns (fine particulate matter), or less than 10 microns (coarse particulate matter), being referred to by the terms '$PM_{2.5}$', and '$PM_{10}$', respectively.

Contaminated Outdoor Air Particulate Matter, and Contaminants

The phrase 'contaminated outdoor air particulate matter', as used herein, generally refers to outdoor air particulate matter (as defined above) which, by itself is at least one type or kind, and form, of contaminant (pollutant), or/and is contaminated (polluted) by (i.e., includes) at least one type or kind, and form, of contaminant (pollutant). Alternatively stated, there are two 'main' cases, and a third 'combination' case thereof, of 'contaminated outdoor air particulate matter'. Namely, in the first main case, the outdoor air particulate matter is by itself at least one type or kind, and form, of contaminant, and is therefore, contaminated outdoor air particulate matter. In the second main case, the outdoor air particulate matter is not by itself a contaminant, rather, the outdoor air particulate matter is contaminated by (i.e., includes) at least one type or kind, and form, of contaminant, and is therefore contaminated outdoor air particulate matter. In the third 'combination' case, the outdoor air particulate matter includes (is composed of) both the first and second main cases of contaminated outdoor air particulate matter. The phrase 'contaminated outdoor air particulate matter', for brevity, is herein abbreviated as the parenthesized term '(COAPM)'.

The term 'contaminant', as used herein, generally refers to essentially any type(s) or kind(s), form(s), size(s), and quantity(ies), and, ranges and distributions thereof, of matter that, when a human (internally or/and externally) contacts (is exposed to) sufficient quantity(ies) or/and duration(s) thereof, such matter is considered (i.e., either known or suspected) as being, or potentially being, problematic, hazardous, or harmful to human health and well being. The terms 'contaminant(s)' and 'contaminated', and their linguistic/grammatical variants, derivatives, or/and conjugates, as used herein, are synonymous with, and equivalent to, the respective terms 'pollutant(s)' and 'polluted', and their linguistic/grammatical variants, derivatives, or/and conjugates, and for consistency, the terms 'contaminant(s)' and 'contaminated' are generally used herein.

A contaminant is composed or made up of essentially any type(s) or kind(s), form(s), size(s), and quantity(ies), and, ranges and distributions thereof, of inorganic or/and organic material(s), substance(s), and, species and components thereof, which is/are in a solid (e.g., particulate, or particulate-like) phase, a liquid (e.g., solution, or suspension) phase, or/and a gaseous (e.g., gas, vapor, or aerosol [gaseous suspension of fine solid or liquid particles circulating throughout air]) phase. According to its composition or make up, a contaminant is definable and characterizable by a set of a wide variety of numerous possible biological, physical, or/and chemical, (biophysicochemical) properties, characteristics, and behavior.

Types or kinds of contaminants which are particularly applicable to implementing embodiments of the present invention are the various different materials and substances that originate (i.e., emitted, exhausted, output into outdoor air or/and make their way into outdoor air) from ground sources of contaminated outdoor air particulate matter. Exemplary categories of such ground sources are: (1) actively used and operative infrastructure type ground sources, such as industrial, commercial, business, public, private, and residential, entities (building and building-like structures, especially, factories, manufacturing plants, power [coal and oil burning] plants, homes, food making and cooking establishments), and, vehicular roadways, bridges, and tunnels; (2) actively used and operative vehicular traffic type ground sources, such as automobiles, buses, trucks, vans, motorbikes, and scooters; and (3) plant matter and ground surface type ground sources, such as trees, bushes, shrubs, plants, flowers, grass, and soil.

Two specific types or kinds of contaminants being in particulate (especially, as powder) forms which are emitted (output) into outdoor air or/and make their way into outdoor air are: (a) dust, originating from essentially all of the above stated examples included in the three exemplary categories of ground sources, namely, infrastructure type ground sources, vehicular traffic type ground sources, and, plant matter and ground surface type ground sources, and (b) pollen, originating from plant matter and ground surface type ground sources, particularly, from (pollen generating) plants and flowers.

All of the above stated types or kinds of contaminants, in non-particulate or/and particulate forms, are emitted (exhausted, output) into outdoor air, and either directly become contaminated outdoor air particulate matter, or first interact with particulate (or/and particulate-like) components of outdoor air which, together, then become contaminated outdoor air particulate matter. More specifically, for the second case of the outdoor air particulate matter itself not being at least one type or kind, and form, of contaminant, then, such outdoor air particular matter is contaminated by at least one type or kind, and form, of contaminant as a result of one or more physicochemical interaction mechanisms (such as physical or/and chemical absorption or/and adsorption) existing between the outdoor air particulate matter and the at least one contaminant, whereby the at least one contaminant is physically or/and chemically absorbed or/and adsorbed on or/and within the outdoor air particulate matter, which together become contaminated outdoor air particulate matter. In such a case, the outdoor air particulate matter serves as the mobile medium or carrier (transporter, conveyor) of the at least one contaminant.

For either case of the outdoor air particulate matter itself being at least one type or kind, and form, of contaminant, or, being contaminated by (i.e., including) at least one type or kind, and form, of contaminant, or, being a combination thereof, then, in view and by extension of the preceding definitions, 'contaminated outdoor air particulate matter' generally refers to matter that, when a human (internally or/and externally) contacts (is exposed to) sufficient quantity(ies) or/and duration(s) thereof, such matter is considered (i.e., either known or suspected) as being, or potentially being, problematic, hazardous, or harmful to human health and well being. Such human (internal or/and external) contact with (exposure to) contaminated outdoor air particulate matter is generally effected by normal human air-breathing mechanisms (i.e., via nasal passageways or/and skin pores), and by normal human air-contacting (exposure) mechanisms (i.e., direct contact (exposure) of non-porous areas of skin to air).

Ground Sources of Contaminated Outdoor Air Particulate Matter

The phrase 'ground source of contaminated outdoor air particulate matter', as used herein, generally refers to essentially any entity that is at least partially (e.g., via a bottom part, base, or foundation) located on (upon) ground level, and whose (intended or/and unintended) existence, or/and operation, or/and control (via human or/and machine type operators or/and controllers) involves being a 'source (originator)' (via emission, exhaustion, or output) of one or more contaminants (as defined hereinabove) that eventually end(s) up in outdoor air, which, as described above, either directly become contaminated outdoor air particulate matter, or first interact with particulate (or/and particulate-like) components of outdoor air which, together, then become contaminated outdoor air particulate matter.

More specifically, the phrase 'ground source of contaminated outdoor air particulate matter', as used herein, generally refers to essentially any entity that is at least partially (e.g., via a bottom part, base, or foundation) located on (upon) ground level, and whose existence, or/and operation, or/and control, via human or/and machine type operators or/and controllers, involves being a 'source (originator)' (via emission, exhaustion, or output) of essentially any type(s) or kind(s), form(s), size(s), and quantity(ies), and, ranges and distributions thereof, of inorganic or/and organic material(s), substance(s), and, species and components thereof, which is/are in a solid (e.g., particulate, or particulate-like) phase, a liquid (e.g., solution, or suspension) phase, or/and a gaseous (e.g., gas, vapor, or aerosol) phase, which is/are considered one or more contaminants that eventually end(s) up in outdoor air, which either directly become contaminated outdoor air particulate matter, or first interact with particulate (or/and particulate-like) components of outdoor air which, together, then become contaminated outdoor air particulate matter. Exemplary categories (and examples thereof) of 'ground sources of contaminated outdoor air particulate matter' are stated hereinabove. The phrase 'ground sources of contaminated outdoor air particulate matter', for brevity, is herein indicated in the drawings (figures) as the phrase 'Ground Sources (COAPM)'.

The term 'real-time', as used herein, generally refers to essentially any action, activity, step, procedure, process, or operation, which is (automatically or/and manually) performed or implemented at the same time, or at nearly the same time, with negligible or insignificant time lag, that the targeted (monitored, tracked, observed) event or situation of interest occurs or takes place.

Accordingly, the phrase 'real-time monitoring and parametric profiling contaminated outdoor air particulate matter throughout a region, via hyper-spectral imaging and analysis', as used herein, generally refers to the various actions, activities, steps, procedures, processes, or operations, of monitoring (tracking, checking, testing) and parametric profiling (characterizing, classifying, correlating) contaminated outdoor air particulate matter throughout a region, via hyper-spectral imaging and analysis, which are (automatically or/and manually) performed or implemented (by any number of human or/and machine type operators or/and controllers) at the same time, or at nearly the same time, with negligible or insignificant time lag, that the targeted (monitored, tracked, observed) event or situation of interest (i.e., generation or/and changes of contaminated outdoor air particulate matter) occurs or takes place.

Accordingly, the phrase 'real-time monitoring and regulating contaminated outdoor air particulate matter throughout a region, via hyper-spectral imaging and analysis', as used herein, generally refers to the various actions, activities, steps, procedures, processes, or operations, of monitoring (tracking, checking, testing), and regulating (controlling, changing) contaminated outdoor air particulate matter throughout a region, via hyper-spectral imaging and analysis, which are (automatically or/and manually) performed or implemented (by any number of human or/and machine type operators or/and controllers) at the same time, or at nearly the same time, with negligible or insignificant time lag, that the targeted (monitored, tracked, observed) event or situation of interest (i.e., generation or/and changes of contaminated outdoor air particulate matter) occurs or takes place.

The phrase 'monitoring contaminated outdoor air particulate matter throughout a region', as used herein, generally refers to systematically (temporally [i.e., as related to time] or/and spatially [i.e., as related to space]) tracking (keeping track of), observing, checking, testing, or/and measuring, any of a wide variety of different (temporally or/and spatially static or/and dynamic) qualitative or/and quantitative properties, parameters, characteristics, or/and behavior, of contaminated outdoor air particulate matter throughout a region. The term 'monitoring', and its linguistic/grammatical variants, derivatives, or/and conjugates, as used herein, are synonymous with, and equivalent to, the term 'tracking (keeping track of)', and its linguistic/grammatical variants, derivatives, or/and conjugates, and for consistency, the term 'monitoring' is generally used herein. The term 'monitoring', and its linguistic/grammatical variants, derivatives, or/and conjugates, as used herein, are either synonymous with, and equivalent to, or, are directly related to or/and involve the same aspects of, the terms 'observing', 'checking', 'testing', or/and 'measuring', and their linguistic/grammatical variants, derivatives, or/and conjugates, and for consistency, the term 'monitoring' is generally used herein.

The phrase 'micrograms per cubic meter', as used herein, refers to concentration of contaminated outdoor air particulate matter (COAPM) in outdoor air expressed in terms of mass (weight) (i.e., micrograms ($\mu$g)) of contaminated outdoor air particulate matter per unit volume (i.e., cubic meter ($m^3$)) of outdoor air, and is herein abbreviated as '$\mu g/m^3$'. With respect to concentration of contaminated outdoor particulate matter (COAPM), although not mentioned herein, alternative phrases and units of mass (weight) and volume are applicable for understanding and implementing exemplary embodiments of the present invention.

Herein, a contaminated outdoor air particulate matter concentration 'range' is expressed in terms of two values of contaminated outdoor air particulate matter concentration, represented as n1 $\mu g/m^3$ and n2 $\mu g/m^3$, and for brevity, as (n1-n2 $\mu g/m^3$). For example, the below illustrative description, along with accompanying FIGS. 7-14, relate to exemplary real-time geographical distribution parametric data-information profiles (in the form of multi-color coded maps) of various contaminated outdoor air particulate matter concentration ranges (n1-n2 $\mu g/m^3$) associated with two exemplary types (namely, a first and a second type) of ground source of contaminated outdoor air particulate matter (Ground Source (COAPM)), at several exemplary test times (t=t1, t2, t3, and t4), for an exemplary window or view within an exemplary first regional quadrant (RQ-1) presented in FIG. 6.

The term 'about', as used herein, refers to ±10% of the stated numerical value.

The phrase 'room temperature', as used herein, refers to a temperature in a range of between about 20° C. and about 25° C.

Throughout the illustrative description of exemplary embodiments, the examples, and the appended claims, of the present invention, a numerical value of a parameter, feature, object, or dimension, may be stated or described in terms of a numerical range format. It is to be fully understood that the stated numerical range format is provided for illustrating implementation of exemplary embodiments of the present invention, and is not to be understood or construed as inflexibly limiting the scope of the exemplary embodiments of the present invention.

Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', is considered equivalent to, and meaning the same as, the phrase 'room temperature refers to a temperature in a range of from about 20° C. to about 25° C.'.

Steps or procedures, sub-steps or sub-procedures, and, equipment and materials, system units, system sub-units, devices, assemblies, sub-assemblies, mechanisms, structures, components, elements, and configurations, and, peripheral equipment, utilities, accessories, and materials, as well as operation and implementation, of exemplary embodiments, alternative embodiments, specific configurations, and, additional and optional aspects, characteristics, or features, thereof, of the present invention, are better understood with reference to the following illustrative description and accompanying drawings. Throughout the following illustrative description and accompanying drawings, same reference notation and terminology (i.e., numbers, letters, symbols, terms, and phrases) are consistently used and refer to same steps or procedures, sub-steps or sub-procedures, system units, system sub-units, devices, assemblies, sub-assemblies, mechanisms, structures, components, elements, and configurations, and, peripheral equipment, utilities, accessories, materials, components, elements, or/and parameters. Some of the accompanying drawings includes a reference x-y coordinate axis system (grid) for indicating x and y directions and (arbitrary) distances with respect to a geographical origin or center, herein, referred to as the 'regional geographical center', abbreviated by the term 'rgc'.

A main aspect of some exemplary embodiments of the present invention relates to a method for real-time monitoring and parametric profiling contaminated outdoor air particulate matter throughout a region, via hyper-spectral imaging and analysis.

Referring now to the drawings, FIG. 1 is a (block-type) flow diagram of the main steps (procedures) of an exemplary embodiment of the method (generally indicated as, and referred to by, reference number 10) for real-time monitoring and parametric profiling contaminated outdoor air particulate matter throughout a region, via hyper-spectral imaging and analysis. In FIG. 1, each main step (procedure) of the exemplary embodiment shown is enclosed inside a separate block (frame) which is assigned a reference number. Accordingly, main steps (a), (b), (c), and (d), are enclosed inside of blocks (frames) 12, 14, 16, and 18, respectively. As shown in FIG. 1, the exemplary embodiment of the method 10 includes the following main steps or procedures, and, components and functionalities thereof.

Step (a) [12], real-time sampling, and hyper-spectrally imaging and analyzing, the contaminated outdoor air particulate matter, separately and simultaneously at each of a plurality of separate locations throughout the region, for generating a corresponding plurality of real-time local contaminated outdoor air particulate matter data-information packages each associated with a separate location in the region.

Step (b) [14], real-time measuring outdoor weather-meteorological conditions, separately and simultaneously at the plurality of separate locations, in a manner synchronized with the real-time sampling, imaging, and analyzing, for generating a corresponding plurality of real-time local outdoor weather-meteorological conditions data-information packages each associated with a separate location.

Step (c) [16], real-time processing and analyzing the real-time local contaminated outdoor air particulate matter data-information packages and the real-time local outdoor weather-meteorological conditions data-information packages, for real-time generating a set of real-time local geographical distribution parametric data-information profiles of the contaminated outdoor air particulate matter, showing real-time local geographical distributions of qualitative or/and quantitative parameters of the contaminated outdoor air particulate matter associated with each separate location, via a global data-information processing and communications unit.

Step (d) [18], real-time processing and analyzing the set of real-time local geographical distribution parametric data-information profiles of the contaminated outdoor air particulate matter, for real-time generating a set of real-time regional geographical distribution parametric data-information profiles of the contaminated outdoor air particulate matter, showing real-time regional geographical distributions of the qualitative or/and quantitative parameters of the contaminated outdoor air particulate matter throughout the region, via the global data-information processing and communications unit.

Another main aspect of some embodiments of the present invention relates to a system for real-time monitoring and parametric profiling contaminated outdoor air particulate matter throughout a region, via hyper-spectral imaging and analysis.

FIG. 2 is a schematic diagram illustrating an exemplary embodiment of the system (generally indicated as, and referred to by, reference number 30) for real-time monitoring and parametric profiling contaminated outdoor air particulate matter throughout a region, via hyper-spectral imaging and analysis, shown for an exemplary region (R-1) 20. FIG. 2 includes a reference x-y coordinate axis system (grid) for indicating x and y directions and (arbitrary) distances (e.g., kilometers, miles, etc.) with respect to a geographical origin or center (regional geographical center, abbreviated by the term 'rgc'). The exemplary embodiment of the system 30 is particularly suitable for implementing the exemplary embodiment of the method 10 presented in FIG. 1. As shown in FIG. 2, the exemplary embodiment of the system 30 includes the following main components and functionalities thereof.

A plurality of local contaminated outdoor air particulate matter monitoring, sampling, and data-information processing stations [Local Station-i, for i=1 to n local stations, where n is, for example, 7, corresponding to an exemplary seven local stations, having respective reference numbers 32, 34, 36, 38, 40, 42, and 44], configured for separately and simultaneously operating at a corresponding plurality of (i, for i=1 to n) separate locations throughout the region (R-1) 20, for real-time sampling, and hyper-spectrally imaging and analyzing the contaminated outdoor air particulate matter (via a corresponding plurality of local outdoor air particulate matter sampling units [OAPMSU], local hyper-spectral imaging and analysis units [HSIAU], and local data-information processing and communications units [LDIPCU]), separately and simultaneously at the plurality of separate locations, for generating a corresponding plurality of real-time local contaminated outdoor air particulate matter data-information packages each associated with a separate location.

A plurality of local weather-meteorological conditions measuring units [WMCMU], configured for separately and simultaneously operating at the plurality of separate locations, and for real-time measuring weather-meteorological conditions, separately and simultaneously at the plurality of separate locations, in a manner synchronized with the real-time sampling, imaging, and analyzing, for generating a corresponding plurality of real-time local outdoor weather-meteorological conditions data-information packages each associated with a separate location.

A global data-information processing and communications unit [GDIPCU] 50, configured for:

(i) real-time processing and analyzing the real-time local contaminated outdoor air particulate matter data-information packages and the real-time local outdoor weather-meteorological conditions data-information packages, for real-time generating a set of real-time local geographical distribution parametric data-information profiles of the contaminated outdoor air particulate matter, showing real-time local geographical distributions of qualitative or/and quantitative parameters of the contaminated outdoor air particulate matter associated with each separate location; and (ii) real-time processing and analyzing the set of real-time local geographical distribution parametric data-information profiles of the contaminated outdoor air particulate matter, for real-time generating a set of real-time regional geographical distribution parametric data-information profiles of the contaminated outdoor air particulate matter, showing real-time regional geographical distributions of the qualitative or/and quantitative parameters of the contaminated outdoor air particulate matter throughout the region (R-1) 20.

The exemplary embodiment of the system 30 also includes a wired or/and wireless (data/information input/output (I/O)) communications network (including appropriate signal paths and junctions), indicated in FIG. 2 (and in FIGS. 3, 4) by the network of dashed lines interconnecting each local contaminated outdoor air particulate matter monitoring, sampling, and data-information processing station [Local Station-i, for i=1 to 7 (32, 34, 36, 38, 40, 42, and 44)], for example, via the local data-information processing and communications units [LDIPCU], with global data-information processing and communications unit [GDIPCU] 50. The (data/information input/output (I/O)) communications network is configured for real-time (wired or/and wireless) communications of data or/and information (such as of the real-time local contaminated outdoor air particulate matter data-information packages, or/and of the real-time local outdoor weather-meteorological conditions data-information packages) to take place between each local contaminated outdoor air particulate matter monitoring, sampling, and data-information processing station [Local Station-i, for i=1 to 7 (32, 34, 36, 38, 40, 42, and 44)], for example, via the local data-information processing and communications units [LDIPCU], with global data-information processing and communications unit [GDIPCU] 50.

In FIG. 2, for illustrative purposes, region (R-1) 20, shown with the reference x-y coordinate axis system (grid) for indicating x and y directions and (arbitrary) distances (e.g., kilometers, miles, etc.) with respect to the geographical origin or center (regional geographical center (rgc)), is divided into four approximately equally sized 'regional' quadrants, namely, first, second, third, and fourth regional quadrants, indicated as RQ-1, RQ-2, RQ-3, and RQ-4, respectively. The plurality of local contaminated outdoor air particulate matter monitoring, sampling, and data-information processing stations [Local Station-i, for i=1 to 7 (32, 34, 36, 38, 40, 42, and 44)], including the corresponding plurality of local outdoor air particulate matter sampling units [OAPMSU], local hyper-spectral imaging and analysis units [HSIAU], and local data-information processing and communications units [LDIPCU], and the corresponding plurality of local weather-meteorological conditions measuring units [WMCMU], are set up and located, according to an exemplary 'clock-wise' pattern, throughout all of the four regional quadrants (RQ-1, RQ-2, RQ-3, and RQ-4) of the region (R-1) 20. Ground sources of contaminated outdoor air particulate matter (indicated as Ground Sources (COAPM)) 'randomly' exist throughout all of the four regional quadrants (RQ-1, RQ-2, RQ-3, and RQ-4) of the region (R-1) 20.

In FIG. 2 (as well as in FIGS. 3-6), throughout the region (R-1) 20, each appearance of the ground sources of contaminated outdoor air particulate matter (Ground Sources (COAPM)) generally refers to essentially any one or more entities, each of which is at least partially (e.g., via a bottom part, base, or foundation) located on (upon) ground level, and whose (intended or/and unintended) existence, or/and operation, or/and control, via human or/and machine type operators or/and controllers, involves being a 'source (originator)' (via emission, exhaustion, or output) of one or more contaminants (as defined hereinabove) that eventually end(s) up in outdoor air, which, as described above, either directly become contaminated outdoor air particulate matter, or first interact with particulate (or/and particulate-like) components of outdoor air which, together, then become contaminated outdoor air particulate matter.

Exemplary categories of ground sources of contaminated outdoor air particulate matter (Ground Sources (COAPM) are: (1) actively used and operative infrastructure type ground sources, such as industrial, commercial, business, public, private, and residential, entities (building and building-like structures, especially, factories, manufacturing plants, power [coal and oil burning] plants, homes, food making and cooking establishments), and, vehicular roadways, bridges, and tunnels; (2) actively used and operative vehicular traffic type ground sources, such as automobiles, buses, trucks, vans, motorbikes, and scooters; and (3) plant matter and ground surface type ground sources, such as trees, bushes, shrubs, plants, flowers, grass, and soil. Such ground sources of contaminated outdoor air particulate matter (Ground Sources (COAPM) are (directly or/and indirectly) operable and controllable via human or/and machine type operators or/and controllers.

Any of the ground sources of contaminated outdoor air particulate matter (Ground Sources (COAPM) may be a 'source (originator)' (via emission, exhaustion, or output) of the following two specific types or kinds of contaminants being in particulate (especially, as powder) forms which are emitted (output) into outdoor air or/and make their way into outdoor air: (a) dust, originating from essentially all of the above stated examples included in the three exemplary categories of ground sources, namely, infrastructure type ground sources, vehicular traffic type ground sources, and, plant matter and ground surface type ground sources, and (b) pollen, originating from plant matter and ground surface type ground sources, particularly, from (pollen generating) plants and flowers.

FIG. 3 is a schematic diagram illustrating the exemplary embodiment of the system 30 presented in FIG. 2, particularly showing performance of main Steps (a) and (b) [12 and 14, respectively, FIG. 1] of the exemplary embodiment of the method 10 presented in FIG. 1. Namely, (a) real-time sampling, and hyper-spectrally imaging and analyzing, the contaminated outdoor air particulate matter, separately and simultaneously at each of the plurality of separate locations throughout the region (R-1) 20, for generating a corresponding plurality of real-time local contaminated outdoor air particulate matter data-information packages each associated with a separate location in the region (R-1) 20, and (b) real-time measuring outdoor weather-meteorological conditions, separately and simultaneously at the plurality of separate locations, in a manner synchronized with the real-time sampling, imaging, and analyzing, for generating a corresponding plurality of real-time local outdoor weather-meteorological conditions data-information packages each associated with a separate location.

As shown in FIG. 3, each of the plurality of local contaminated outdoor air particulate matter monitoring, sampling, and data-information processing stations [Local Station-i, for i=1 to 7 (32, 34, 36, 38, 40, 42, and 44)], including its local hyper-spectral imaging and analysis unit [HSIAU] and its local weather-meteorological conditions measuring unit [WMCMU], along with its local data-information processing and communications units [LDIPCU], is operated for performing main Steps (a) and (b) of method 10 (FIG. 1). In FIG. 3, such is indicated by an arrow leading from each local contaminated outdoor air particulate matter monitoring, sampling, and data-information processing station, namely, Local Station-i, for i=1 to 7 (32, 34, 36, 38, 40, 42, and 44), to the following respective adjacently drawn parenthesized text:

$$\left\{\begin{array}{l}\text{Data-information packages}-i\\ >\text{real-time local outdoor air}\\ \text{particulate matter}-i.\\ >\text{real-time local outdoor weather-}\\ \text{meteorological conditions}-i.\end{array}\right\}$$

for i=1 to 7, having respective reference numbers 72, 74, 76, 78, 80, 82, and 84.

Accordingly, each local contaminated outdoor air particulate matter monitoring, sampling, and data-information processing station, namely, Local Station-i, for i=1 to 7 (32, 34, 36, 38, 40, 42, and 44), performs these main steps of real-time sampling, and hyper-spectrally imaging and analyzing, the contaminated outdoor air particulate matter, separately and simultaneously at each of the plurality of separate locations throughout the region (R-1) 20, for generating a corresponding plurality of real-time local contaminated outdoor air particulate matter data-information packages (i.e., >real-time local outdoor air particulate matter—i), and real-time measuring outdoor weather-meteorological conditions, separately and simultaneously at the plurality of separate locations, in a manner synchronized with the real-time sampling, imaging, and analyzing, for generating a corresponding plurality of real-time local outdoor weather-meteorological conditions data-information packages (i.e., >real-time local outdoor weather-meteorological conditions—i), where the data-information packages are associated with a separate location, indicated in FIG. 3 as Data-information packages—i.

Figure 4:
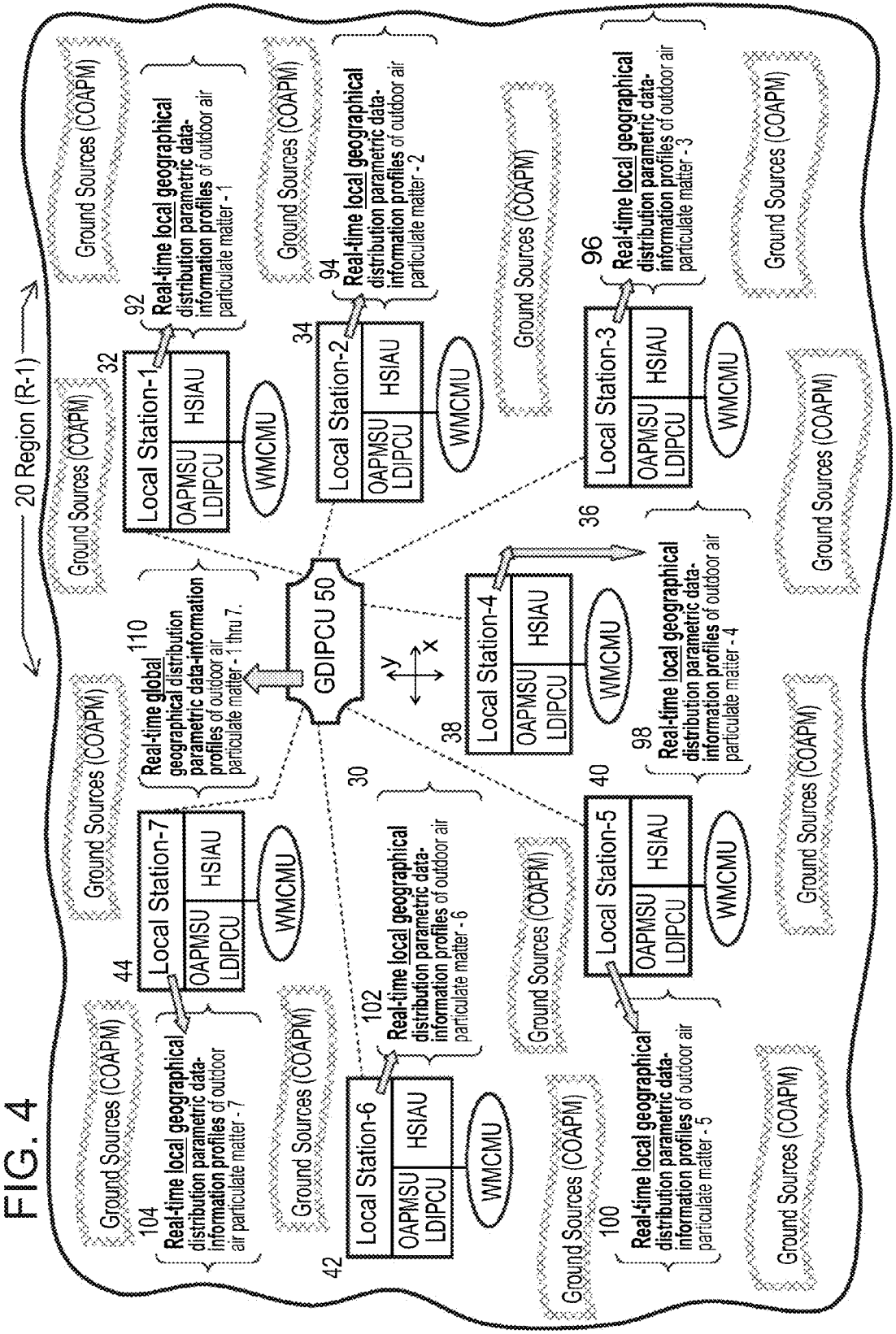
FIG. 4 is a schematic diagram illustrating the exemplary embodiment of the system presented in FIG. 2, particularly showing performance of main Steps (c) and (d) of the exemplary embodiment of the method presented in FIG. 1, in accordance with the present invention.

FIG. 4 is a schematic diagram illustrating the exemplary embodiment of the system 30 presented in FIG. 2, particularly showing performance of main Steps (c) and (d) [16 and 18, respectively, FIG. 1] of the exemplary embodiment of method 10 presented in FIG. 1. Namely, (c) real-time processing and analyzing the real-time local contaminated outdoor air particulate matter data-information packages and the real-time local outdoor weather-meteorological conditions data-information packages, for real-time generating a set of real-time local geographical distribution parametric data-information profiles of the contaminated outdoor air particulate matter, showing real-time local geographical distributions of qualitative or/and quantitative parameters of the contaminated outdoor air particulate matter associated with each separate location, via a global data-information processing and communications unit [GDIPCU] 50, and (d) real-time processing and analyzing the set of real-time local geographical distribution parametric data-information profiles of the contaminated outdoor air particulate matter, for real-time generating a set of real-time regional geographical distribution parametric data-information profiles of the contaminated outdoor air particulate matter, showing real-time regional geographical distributions of the qualitative or/and quantitative parameters of the contaminated outdoor air particulate matter throughout the region (R-1) 20, via the global data-information processing and communications unit [GDIPCU] 50.

As shown in FIG. 4, each of the plurality of local contaminated outdoor air particulate matter monitoring, sampling, and data-information processing stations [Local Station-i, for i=1 to 7 (32, 34, 36, 38, 40, 42, and 44)], including its local hyper-spectral imaging and analysis unit [HSIAU] and its local weather-meteorological conditions measuring unit [WMCMU], along with its local data-information processing and communications units [LDIPCU], is operated for performing main Step (c) of method 10 (FIG. 1). In FIG. 4, such is indicated by an arrow leading from each local contaminated outdoor air particulate matter monitoring, sampling, and data-information processing station, namely, Local Station-i, for i=1 to 7 (32, 34, 36, 38, 40, 42, and 44), to the following respective adjacently drawn parenthesized text:

{ Real-time global geographical distribution parametric data-information profiles of outdoor air particulate matter – i. } for i=1 to 7, having respective reference numbers 92, 94, 96, 98, 100, 102, and 104.

Additionally, as shown in FIG. 4, each local contaminated outdoor air particulate matter monitoring, sampling, and data-information processing station, namely, Local Station-i, for i=1 to 7 (32, 34, 36, 38, 40, 42, and 44), performs main Step (d) of real-time processing and analyzing the set of real-time local geographical distribution parametric data-information profiles of the contaminated outdoor air particulate matter (i.e., Real-time local geographical distribution parametric data-information profiles of outdoor air particulate matter—i), for real-time generating a set of real-time regional geographical distribution parametric data-information profiles of the contaminated outdoor air particulate matter, showing real-time regional geographical distributions of the qualitative or/and quantitative parameters of the contaminated outdoor air particulate matter throughout the region (R-1) 20, via global data-information processing and communications unit [GDIPCU] 50. In FIG. 4, such is indicated by the (data/information input/output (I/O)) communications network (dashed lines) interconnecting each local contaminated outdoor air particulate matter monitoring, sampling, and data-information processing station [Local Station-i, for i=1 to 7 (32, 34, 36, 38, 40, 42, and 44], for example, via the local data-information processing and communications units [LDIPCU], with global data-information processing and communications unit [GDIPCU] 50, and by the arrow leading from global data-information processing and communications unit [GDIPCU] 50 to the following adjacently drawn parenthesized text (having reference number 110):

{ Real-time global geographical distribution parametric data-information profiles of outdoor air particulate matter - 1 thru 7. }

Figure 5:
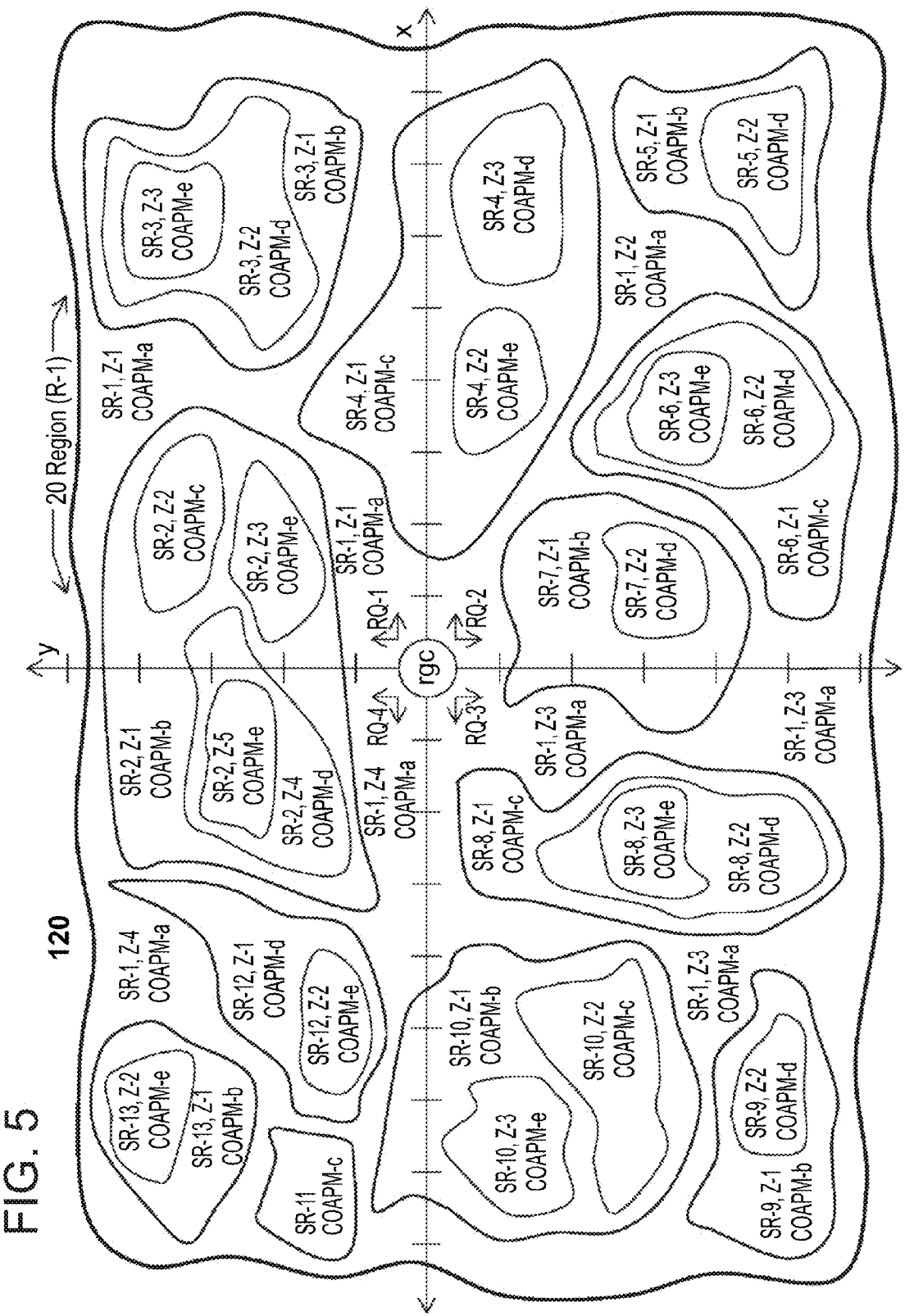
FIG. 5 is a schematic diagram illustrating implementation of the exemplary embodiments of the method and system presented in FIGS. 1-4, particularly showing a (simulated) exemplary result of performing main Step (d), being an exemplary generated real-time regional geographical distribution parametric data-information profile of the contaminated outdoor air particulate matter, showing exemplary real-time regional geographical distributions of an exemplary qualitative or/and quantitative parameter [concentration range of the contaminated outdoor air particulate matter in the outdoor air, referred to as contaminated outdoor air particulate matter concentration range (COAPM-α)], for a plurality of exemplary sub-regions (SR-j) and zones (Z-k) therein, throughout the region (R-1), in accordance with the present invention.

FIG. 5 is a schematic diagram illustrating implementation of the exemplary embodiments of the method and system presented in FIGS. 1-4, particularly showing a (simulated) exemplary result of performing main Step (d) [18, FIG. 1]. Namely, an exemplary generated real-time regional geographical distribution parametric data-information profile (generally indicated as, and referred to by, reference number 120) of the contaminated outdoor air particulate matter, showing exemplary real-time regional geographical distributions of an exemplary qualitative or/and quantitative parameter, [concentration range of the contaminated outdoor air particulate matter in the outdoor air, referred to as contaminated outdoor air particulate matter concentration range (COAPM-α), for α=a, b, c, d, or e, with each letter corresponding to a different specific concentration range of the contaminated outdoor air particulate matter in the outdoor air], for a plurality of exemplary sub-regions (SR-j) and zones (Z-k) therein, throughout the region (R-1) 20.

As shown in FIG. 5, the exemplary region (R-1) 20 is divided or segmented into a plurality of exemplary (smaller sized) sub-regions, SR-j, for j=1 to p sub-regions, where p is, for example, 13, corresponding to an exemplary thirteen sub-regions, having respective reference notations SR-1, SR-2, SR-3, SR-4, SR-5, SR-6, SR-7, SR-8, SR-9, SR-10, SR-11, SR-12, and SR-13. Furthermore, each sub-region, SR-j, for j=1 to 13 sub-regions, is divided or segmented into a plurality of exemplary (smaller sized) zones, Z-k, for k=1 to q zones, where q varies, for example, from 1 to 5, corresponding to up to an exemplary five zones in a given sub-region, SR-j, having reference notations Z-1, Z-2, Z-3, Z-4, Z-5. Each exemplary zone, Z-k, for k=1 to 5 zones, is associated with and assigned a concentration range of the contaminated outdoor air particulate matter in the outdoor air, namely, contaminated outdoor air particulate matter concentration range, COAPM-α (for α=a, b, c, d, or e, with each letter corresponding to a different specific concentration range of the contaminated outdoor air particulate matter in the outdoor air), being the exemplary qualitative or/and quantitative parameter of the contaminated outdoor air particulate matter that is shown via the exemplary generated real-time regional geographical distribution parametric data-information profile 120 of the contaminated outdoor air particulate matter.

Concentration of contaminated outdoor particulate matter (COAPM) in the outdoor air can be quantitatively expressed using various different conventions and notations. Herein, the well known and commonly used convention and notation based on mass (weight) of contaminated outdoor particulate matter (COAPM) per unit volume of outdoor air, is used for such quantitative expression. Accordingly, the concentration of contaminated outdoor air particulate matter (COAPM) in outdoor air is quantitatively expressed in terms of mass (weight) (e.g., micrograms (µg)) of contaminated outdoor air particulate matter per unit volume (e.g., cubic meter ($m^3$)) of outdoor air, namely, micrograms per cubic meter, herein abbreviated as µg/$m^3$. A contaminated outdoor air particulate matter concentration 'range' is expressed in terms of two values of contaminated outdoor air particulate matter concentration, represented as n1 µg/$m^3$ and n2 µg/$m^3$, and for brevity, as (n1-n2 µg/$m^3$).

Based on the preceding described convention and notation for quantitatively expressing concentration of contaminated outdoor particulate matter (COAPM) in the outdoor air, the concentration range of the contaminated outdoor air particulate matter in the outdoor air, namely, the contaminated outdoor air particulate matter concentration range, COAPM-α, for α=a, b, c, d, or e, with each letter corresponding to a different specific concentration range of the contaminated outdoor air particulate matter in the outdoor air, has the following notations and exemplary specific concentration range values or magnitudes:

COAPM-a, a=0-10,
COAPM-b, b=10-20,
COAPM-c, c=20-30,
COAPM-d, d=30-40, and
COAPM-e, e=40-45, micrograms per cubic meter (µg/$m^3$) of contaminated outdoor air particulate matter in the outdoor air.

Thus, as shown in FIG. 5, as a first example, in region (R-1) 20, the first sub-region, SR-1, is divided or segmented into a plurality of four (smaller sized) zones, namely, Z-1, Z-2, Z-3, and Z-4, wherein each zone is associated with and assigned a value (magnitude) of the contaminated outdoor air particulate matter concentration range, COAPM-α, as defined above. In this particular case, wherein the first sub-region, SR-1, is considered a type of a 'background' or base sub-region with respect to the other sub-regions, SR-2 through SR-12, in the first sub-region, SR-1, in each of the first, second, third, and fourth zones, Z-1, Z-2, Z-3, and Z-4, the contaminated outdoor air particulate matter concentration range is noted as COAPM-α, corresponding to a range of 0-10 micrograms per cubic meter (μg/m³) of contaminated outdoor air particulate matter in the outdoor air.

As shown in FIG. 5, as a second example, in region (R-1) 20, the second sub-region, SR-2, is divided or segmented into a plurality of five (smaller sized) zones, namely, Z-1, Z-2, Z-3, Z-4, and Z-5, wherein each zone is associated with and assigned a value (magnitude) of the contaminated outdoor air particulate matter concentration range, COAPM-α, as defined above, and as follows:

SR-2, first zone, Z-1, COAPM-b, 10-20 micrograms per cubic meter (μg/m³);
SR-2, second zone, Z-2, COAPM-c, 20-30 micrograms per cubic meter (μg/m³);
SR-2, third zone, Z-3, COAPM-e, 40-45 micrograms per cubic meter (μg/m³);
SR-2, fourth zone, Z-4, COAPM-d, 30-40 micrograms per cubic meter (μg/m³); and
SR-2, fifth zone, Z-5, COAPM-e, 40-45 micrograms per cubic meter (μg/m³).

As shown in FIG. 5, as a third example, in region (R-1) 20, the eighth sub-region, SR-8, is divided or segmented into a plurality of three (smaller sized) zones, namely, Z-1, Z-2, and Z-3, wherein each zone is associated with and assigned a value (magnitude) of the contaminated outdoor air particulate matter concentration range, COAPM-α, as defined above, and as follows:

SR-8, first zone, Z-1, COAPM-c, 20-30 micrograms per cubic meter (μg/m³);
SR-8, second zone, Z-2, COAPM-d, 30-40 micrograms per cubic meter (μg/m³); and
SR-8, third zone, Z-3, COAPM-e, 40-45 micrograms per cubic meter (μg/m³).

In FIG. 5, in the exemplary generated real-time regional geographical distribution parametric data-information profile 120 of the contaminated outdoor air particulate matter throughout the region (R-1) 20, for each sub-region, SR-j, for j=1 to 13 sub-regions, and for each (smaller sized) zone, Z-k, for k=1 to q zones, therein, the indicated concentration range of the contaminated outdoor air particulate matter in the outdoor air, namely, contaminated outdoor air particulate matter concentration range, COAPM-α (for α=a, b, c, d, or e), corresponds to the (overall or total) combined concentration of the various different types or kinds and quantities of contaminated outdoor air particulate matter in the outdoor air which result from the (overall or total) combined contributions of the various ground sources of contaminated outdoor air particulate matter (Ground Sources (COAPM)), which are 'geographically' associated with (i.e., in measurable proximity to) each respective sub-region, SR-j, and (smaller sized) zones, Z-k, therein. Moreover, either the same or different types or kinds and numbers (i.e., of the above described exemplary categories [(1), (2), (3)]) of ground sources of contaminated outdoor air particulate matter (Ground Sources (COAPM)) are 'geographically' associated with (i.e., in measurable proximity to) more than one sub-region, SR-j, and (smaller sized) zones, Z-k, therein.

Thus, for example, in the exemplary generated real-time regional geographical distribution parametric data-information profile 120 of the contaminated outdoor air particulate matter throughout the region (R-1) 20, for the second sub-region, SR-2, and for the (smaller sized) third zone, Z-3, the contaminated outdoor air particulate matter concentration range (COAPM-e) of 40-45 micrograms per cubic meter (μg/m³) corresponds to the (overall or total) combined concentration of the various different types or kinds and quantities of contaminated outdoor air particulate matter in the outdoor air which result from the (overall or total) combined contributions of the various ground sources of contaminated outdoor air particulate matter (Ground Sources (COAPM)), which are 'geographically' associated with (i.e., in measurable proximity to) the second sub-region, SR-2, and the (smaller sized) third zone, Z-3, therein. Moreover, any types or kinds and numbers (i.e., of the above described exemplary categories [(1), (2), (3)]) of ground sources of contaminated outdoor air particulate matter (Ground Sources (COAPM)) are 'geographically' associated with (i.e., in measurable proximity to) the second sub-region, SR-2, and the (smaller sized) third zone, Z-3, therein.

More specifically, such ground sources of contaminated outdoor air particulate matter (Ground Sources (COAPM)) which are 'geographically' associated with (i.e., in measurable proximity to) the second sub-region, SR-2, and the (smaller sized) third zone, Z-3, therein, are any combination of the above described exemplary categories (1), (2), or/and (3), namely, (1) actively used and operative infrastructure type ground sources, such as industrial, commercial, business, public, private, and residential, entities (building and building-like structures, especially, factories, manufacturing plants, power [coal and oil burning] plants, homes, food making and cooking establishments), and, vehicular roadways, bridges, and tunnels; or/and (2) actively used and operative vehicular traffic type ground sources, such as automobiles, buses, trucks, vans, motorbikes, and scooters; and (3) plant matter and ground surface type ground sources, such as trees, bushes, shrubs, plants, flowers, grass, and soil.

Figure 6:
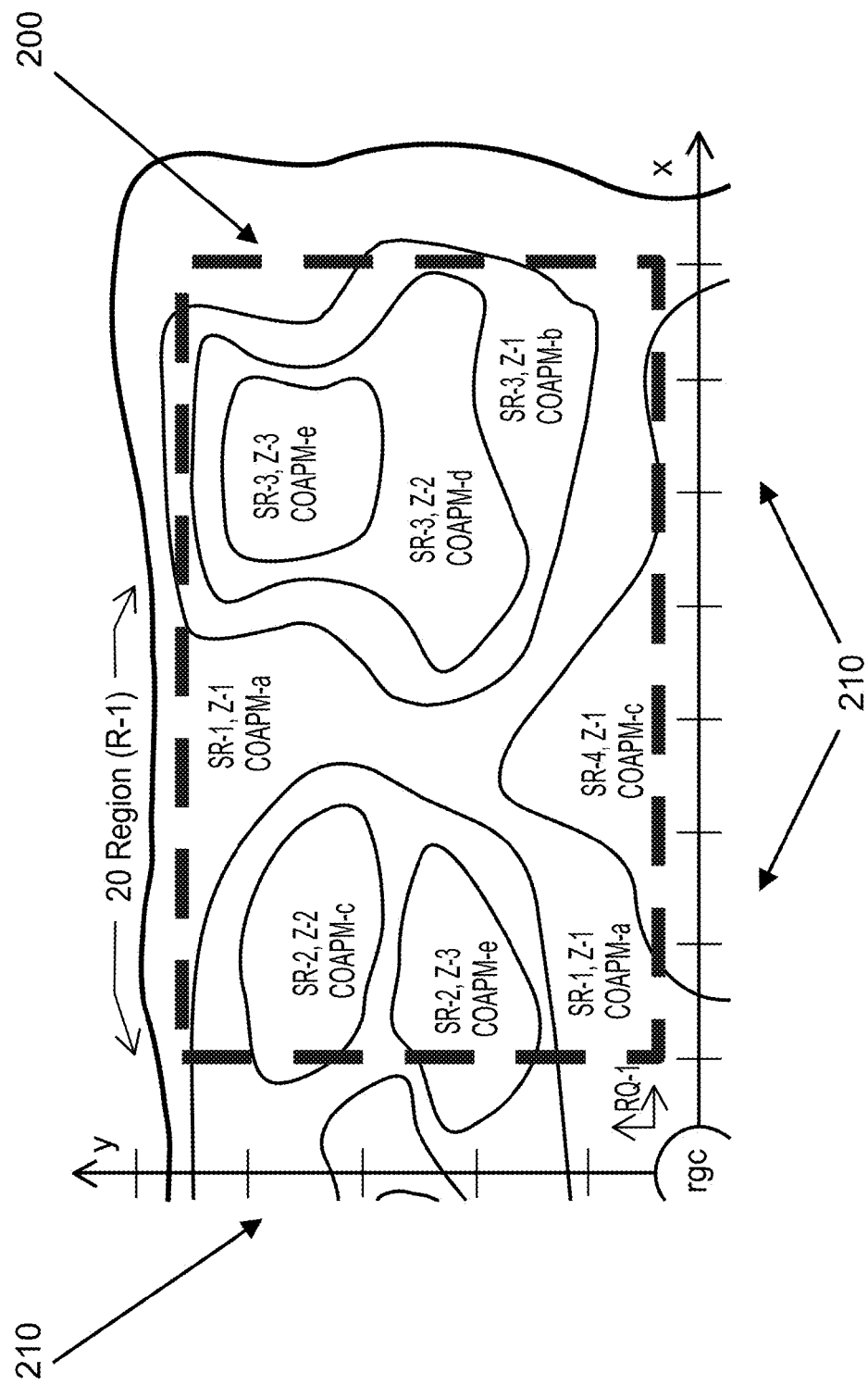
FIG. 6 is a schematic diagram illustrating an exemplary window or view within the first regional quadrant (RQ-1) of the exemplary generated real-time regional geographical distribution parametric data-information profile of the contaminated outdoor air particulate matter presented in FIG. 5, showing therein an exemplary real-time regional geographical distribution of the contaminated outdoor air particulate matter concentration range (COAPM-α) of the contaminated outdoor air particulate matter in the outdoor air, for parts of exemplary sub-regions (SR-1, SR-2, SR-3, and SR-4) and zones (Z-k) therein, in the first regional quadrant (RQ-1) of the region (R-1), in accordance with the present invention.

FIG. 6 is a schematic diagram illustrating an exemplary window or view (reference number 200) within the first regional quadrant (RQ-1) of the exemplary generated real-time regional geographical distribution parametric data-information profile 120 of the contaminated outdoor air particulate matter presented in FIG. 5, showing therein an exemplary real-time regional geographical distribution of the contaminated outdoor air particulate matter concentration range (COAPM-α) of the contaminated outdoor air particulate matter in the outdoor air, for parts of the four exemplary sub-regions (SR-1, SR-2, SR-3, and SR-4) and zones (Z-k) therein, in the first regional quadrant (RQ-1) of the region (R-1) 20.

In FIG. 6, the contents, and frame (border), of the exemplary window or view within the first regional quadrant (RQ-1) are together indicated by reference number 200. The reference x-y coordinate axis system (grid) for indicating x and y directions and (arbitrary) distances (e.g., kilometers, miles, etc.) with respect to the geographical origin or center (regional geographical center (rgc)), is indicated by reference number 210.

Figure 7:
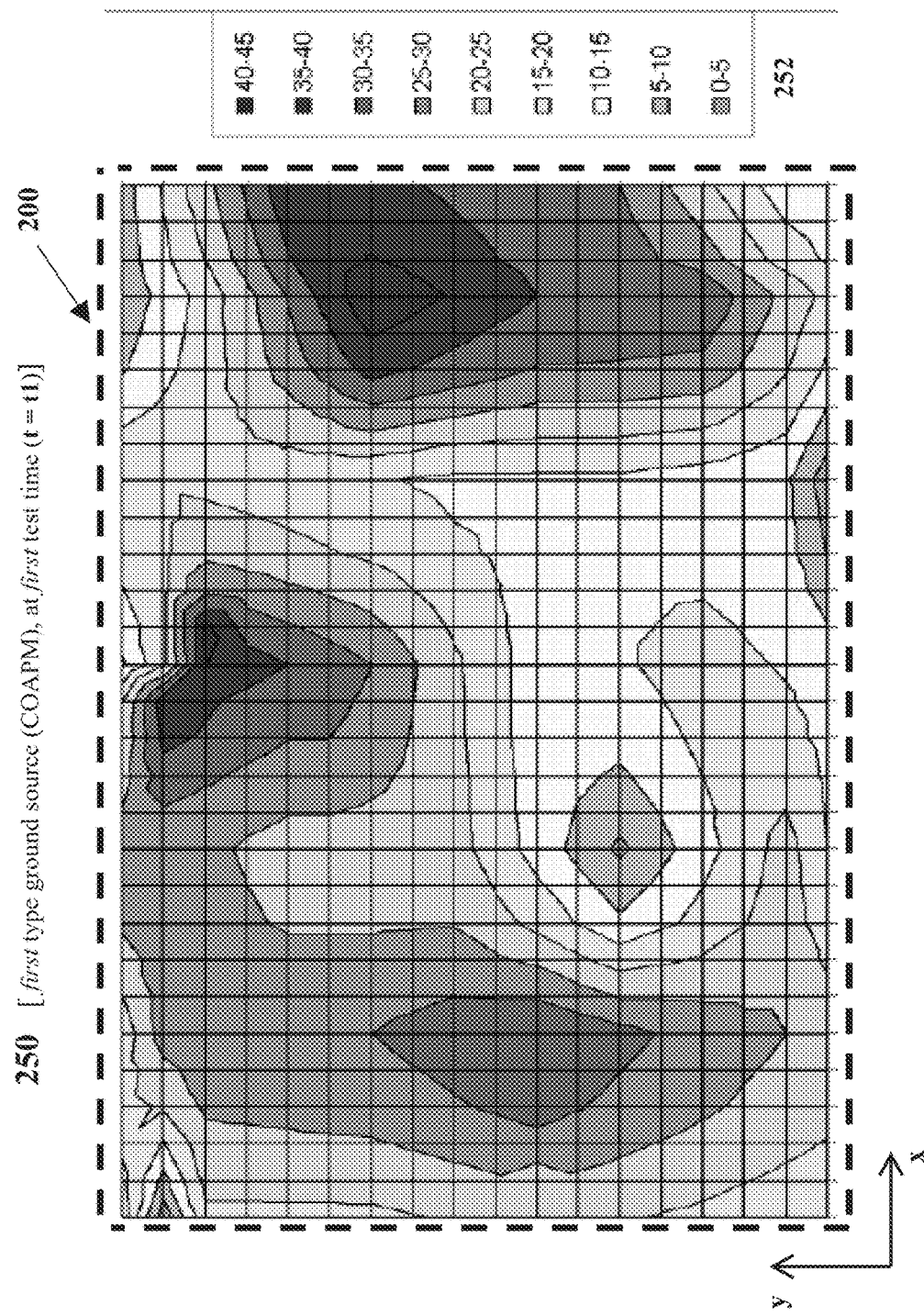
FIG. 7 is a schematic diagram illustrating a (simulated) exemplary real-time geographical distribution parametric data-information profile (in the form of a multi-color coded map) of the contaminated outdoor air particulate matter concentration range (n1-n2 μg/m$^3$) associated with an exemplary first type of ground source of contaminated outdoor air particulate matter (Ground Source (COAPM)), at an exemplary first test time (t=t1), for the exemplary window or view within the first regional quadrant (RQ-1) presented in FIG. 6, in accordance with the present invention.

FIG. 7 is a schematic diagram illustrating a (simulated) exemplary real-time geographical distribution parametric data-information profile (in the form of a multi-color coded map) 250 of the contaminated outdoor air particulate matter concentration range (n1-n2 μg/m³) associated with (originating from) an exemplary first type of ground source of contaminated outdoor air particulate matter (Ground Source (COAPM)), at an exemplary first test time (t=t1), for the exemplary window or view 200 within the first regional quadrant (RQ-1) presented in FIG. 6.

Figure 8:
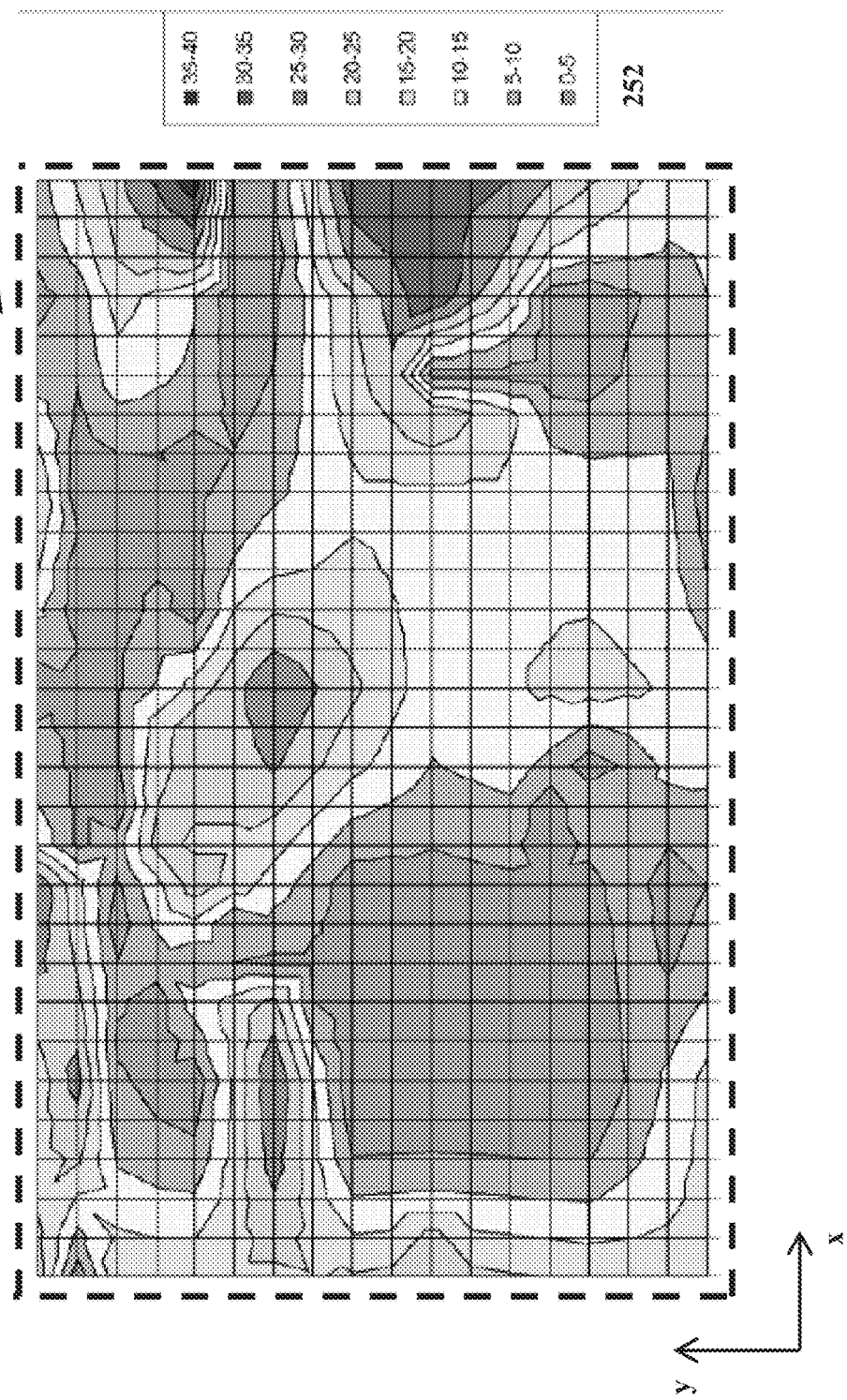
FIG. 8 is a schematic diagram illustrating a (simulated) exemplary real-time geographical distribution parametric data-information profile (in the form of a multi-color coded map) of the contaminated outdoor air particulate matter concentration range (n1–n2 μg/m$^3$) associated with an exemplary second type of ground source of contaminated outdoor air particulate matter (Ground Source (COAPM)), at the 'same' exemplary first test time (t=t1) of FIG. 7, for the 'same' exemplary window or view within the first regional quadrant (RQ-1) presented in FIG. 6, in accordance with the present invention.

FIG. 8 is a schematic diagram illustrating a (simulated) exemplary real-time geographical distribution parametric data-information profile (in the form of a multi-color coded map) 260 of the contaminated outdoor air particulate matter concentration range (n1-n2 µg/m$^3$) associated with (originating from) an exemplary second type of ground source of contaminated outdoor air particulate matter (Ground Source (COAPM)), at the 'same' exemplary first test time (t=t1) of FIG. 7, for the 'same' exemplary window or view 200 within the first regional quadrant (RQ-1) presented in FIG. 6.

FIGS. 7 and 8 include reference x and y coordinate axes, and a grid, for indicating x and y directions and (arbitrary) distances (e.g., kilometers, miles, etc.) with respect to an arbitrarily positioned geographical origin of exemplary window or view 200. A set or series of the different (color coded) levels (and corresponding values thereof) of the contaminated outdoor air particulate matter concentration range, quantitatively expressed in terms of n1-n2 µg/m$^3$, and associated with (originating from) the exemplary first or second type of ground source of contaminated outdoor air particulate matter (Ground Source (COAPM)), is indicated by reference number 252. As shown thereby, the contaminated outdoor air particulate matter concentration range is represented by, and has, the following set or series 252 of exemplary different (color coded) levels and corresponding values or magnitudes thereof: bright green, 0-5; green, 5-10; light yellow, 10-15; yellow, 15-20; dark yellow, 20-25; orange, 25-30; red, 30-35; brown, 35-40; and dark green, 40-45, micrograms per cubic meter (µg/m$^3$) of contaminated outdoor air particulate matter in the outdoor air.

Figure 9:
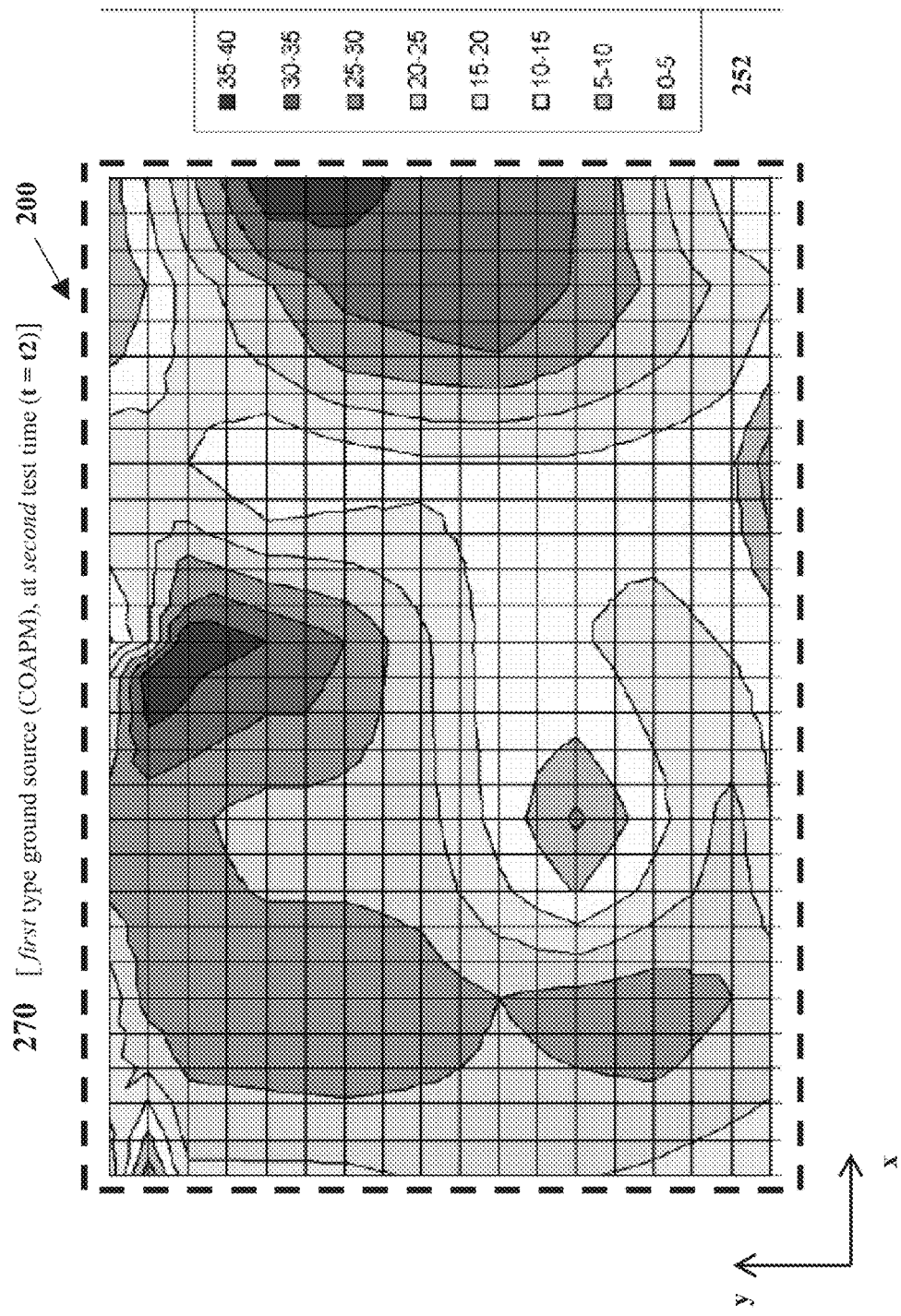
FIGS. 9, 10, and 11 are schematic diagrams illustrating (simulated) exemplary real-time geographical distribution parametric data-information profiles (in the form of multi-color coded maps) of the contaminated outdoor air particulate matter concentration range (n1–n2 μg/m$^3$) associated with the 'same' exemplary first type of ground source of contaminated outdoor air particulate matter (Ground Source (COAPM)), at exemplary second, third, and fourth, test times (t=t2, t3, and t4, respectively), for the 'same' exemplary window or view within the first regional quadrant (RQ-1) presented in FIG. 6, in accordance with the present invention.
Figure 10:
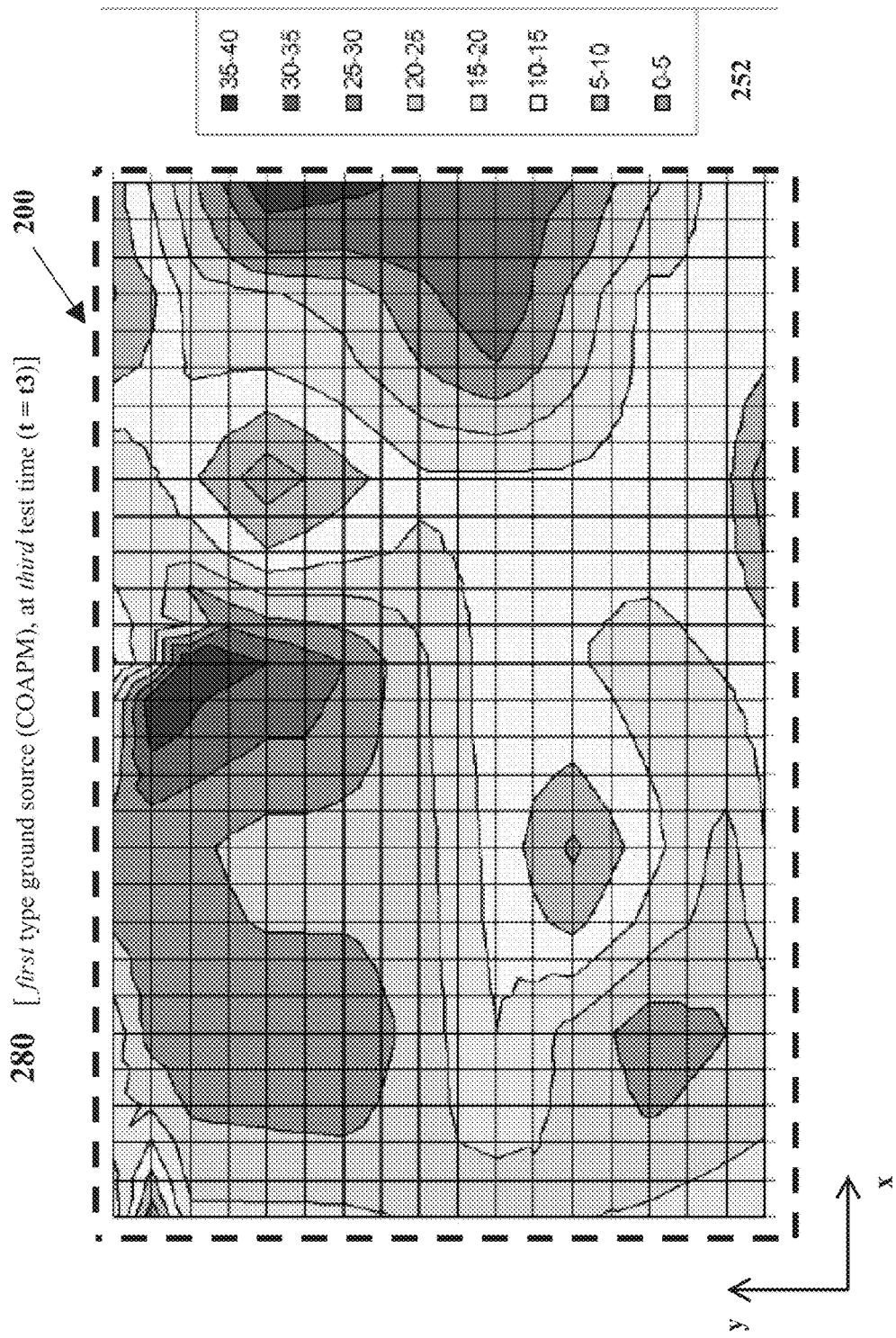
Figure 11:
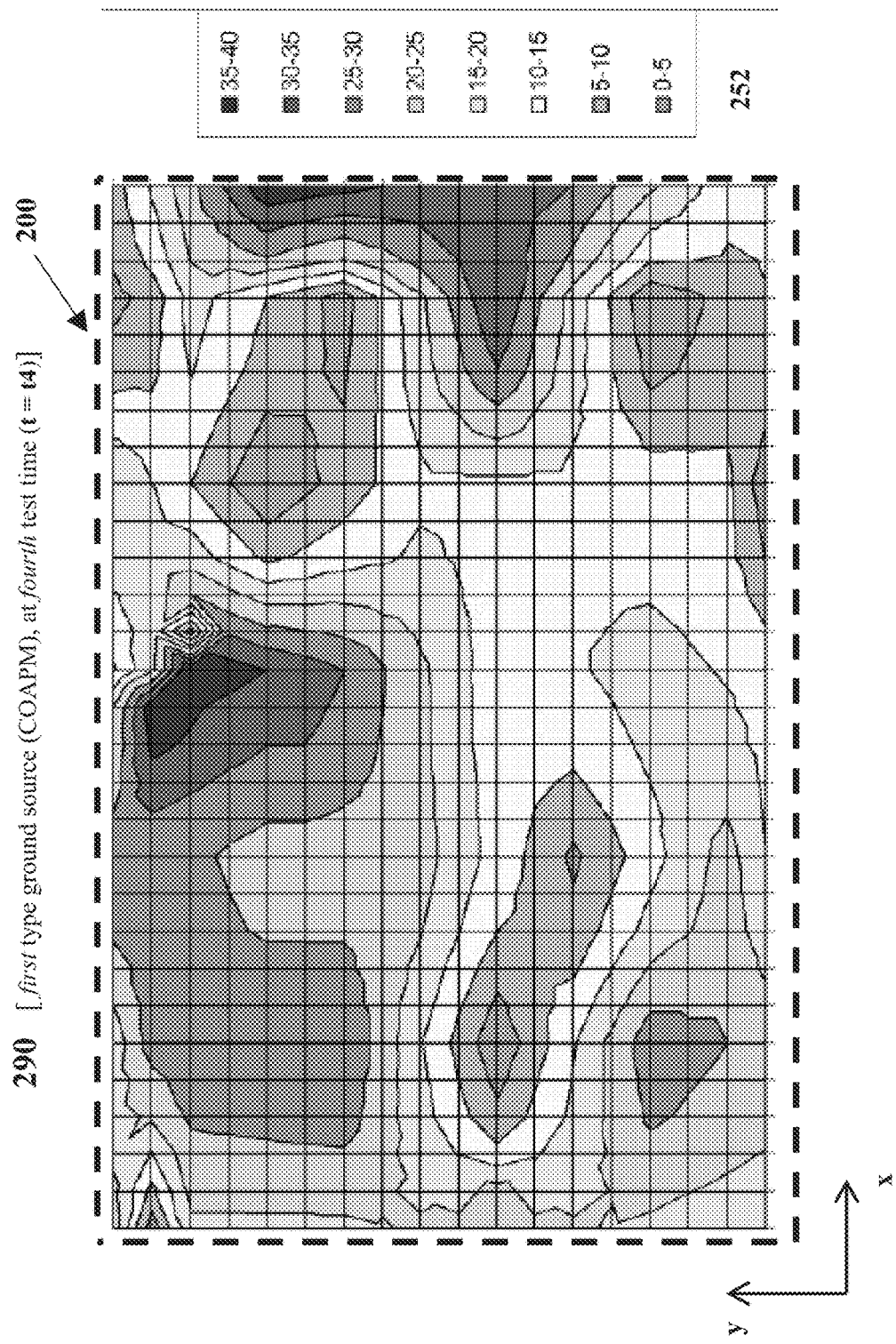

FIGS. 9, 10, and 11 are schematic diagrams illustrating (simulated) exemplary real-time geographical distribution parametric data-information profiles (in the form of multi-color coded maps) 270, 280, and 290, respectively, of the contaminated outdoor air particulate matter concentration range (n1-n2 µg/m$^3$) associated with (originating from) the 'same' exemplary first type of ground source of contaminated outdoor air particulate matter (Ground Source (COAPM)), at exemplary second, third, and fourth, test times (t=t2, t3, and t4, respectively), for the 'same' exemplary window or view within the first regional quadrant (RQ-1) presented in FIG. 6.

Figure 12:
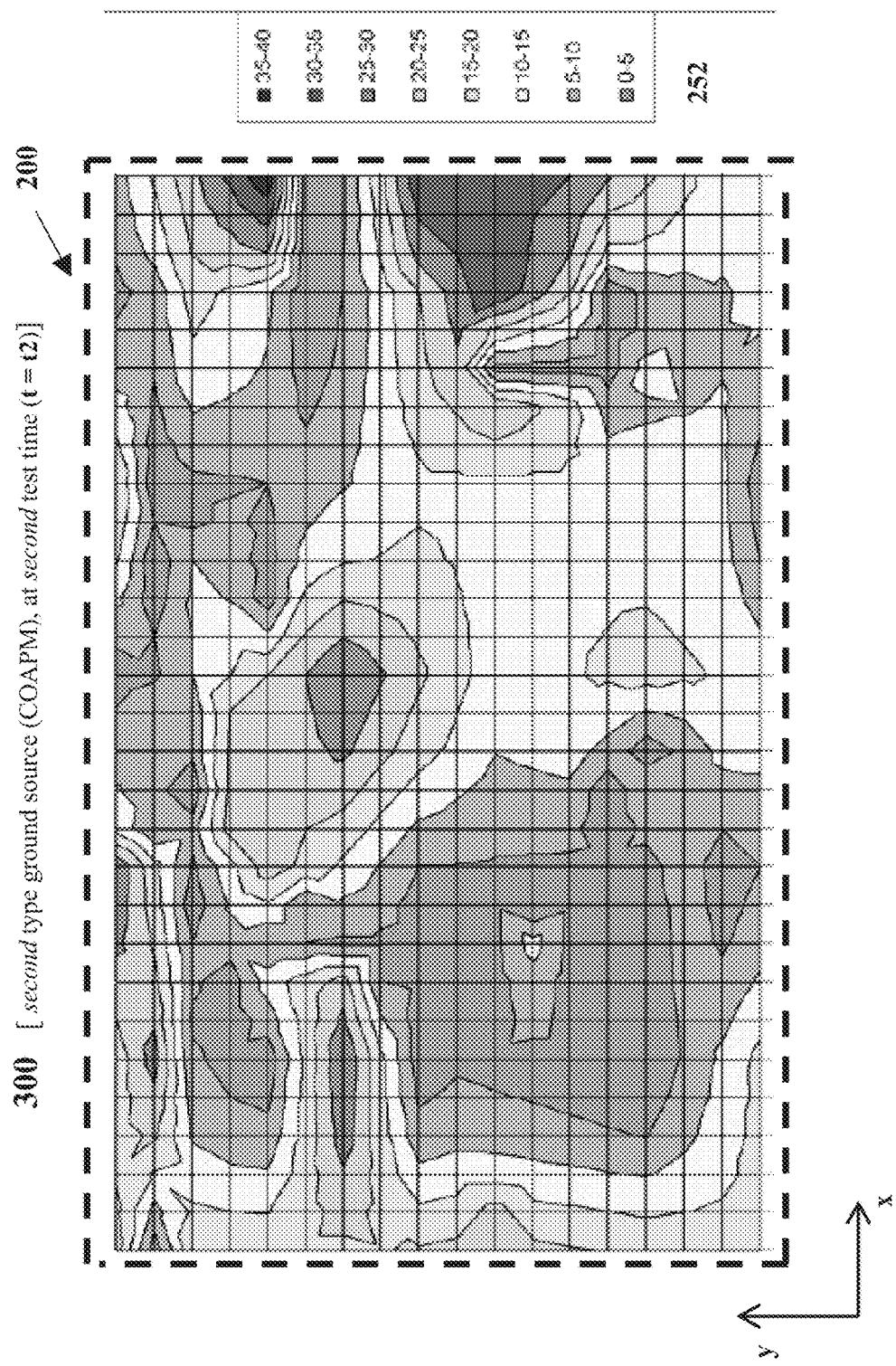
FIGS. 12, 13, and 14 are schematic diagrams illustrating (simulated) exemplary real-time geographical distribution parametric data-information profiles (in the form of multi-color coded maps) of the contaminated outdoor air particulate matter concentration range (n1-n2 μg/m$^3$) associated with the 'same' exemplary second type of ground source of contaminated outdoor air particulate matter (Ground Source (COAPM)), at the 'same' exemplary second, third, and fourth, test times (t=t2, t3, and t4, respectively), for the 'same' exemplary window or view within the first regional quadrant (RQ-1) presented in FIG. 6, in accordance with the present invention.
Figure 13:
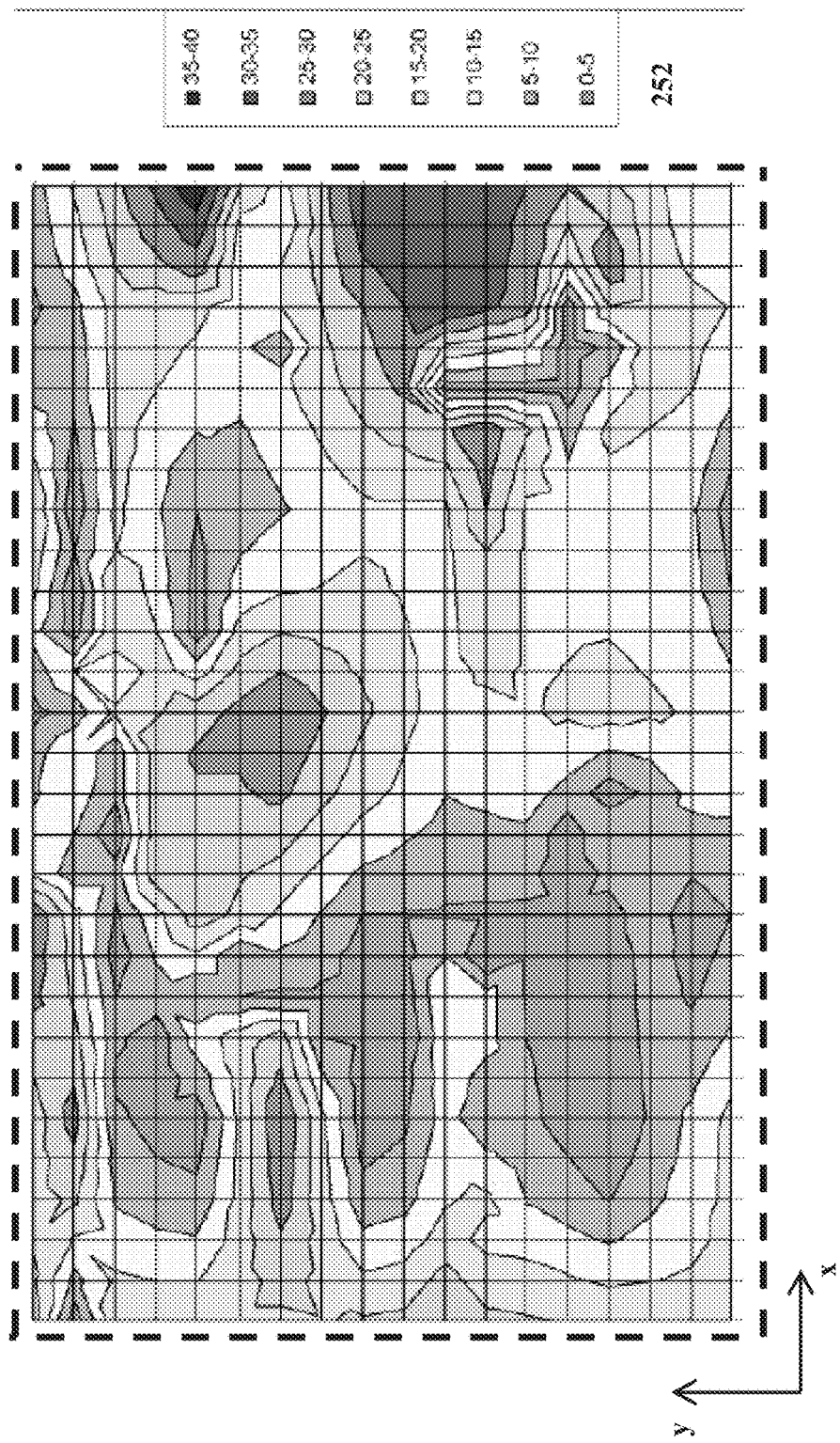
Figure 14:
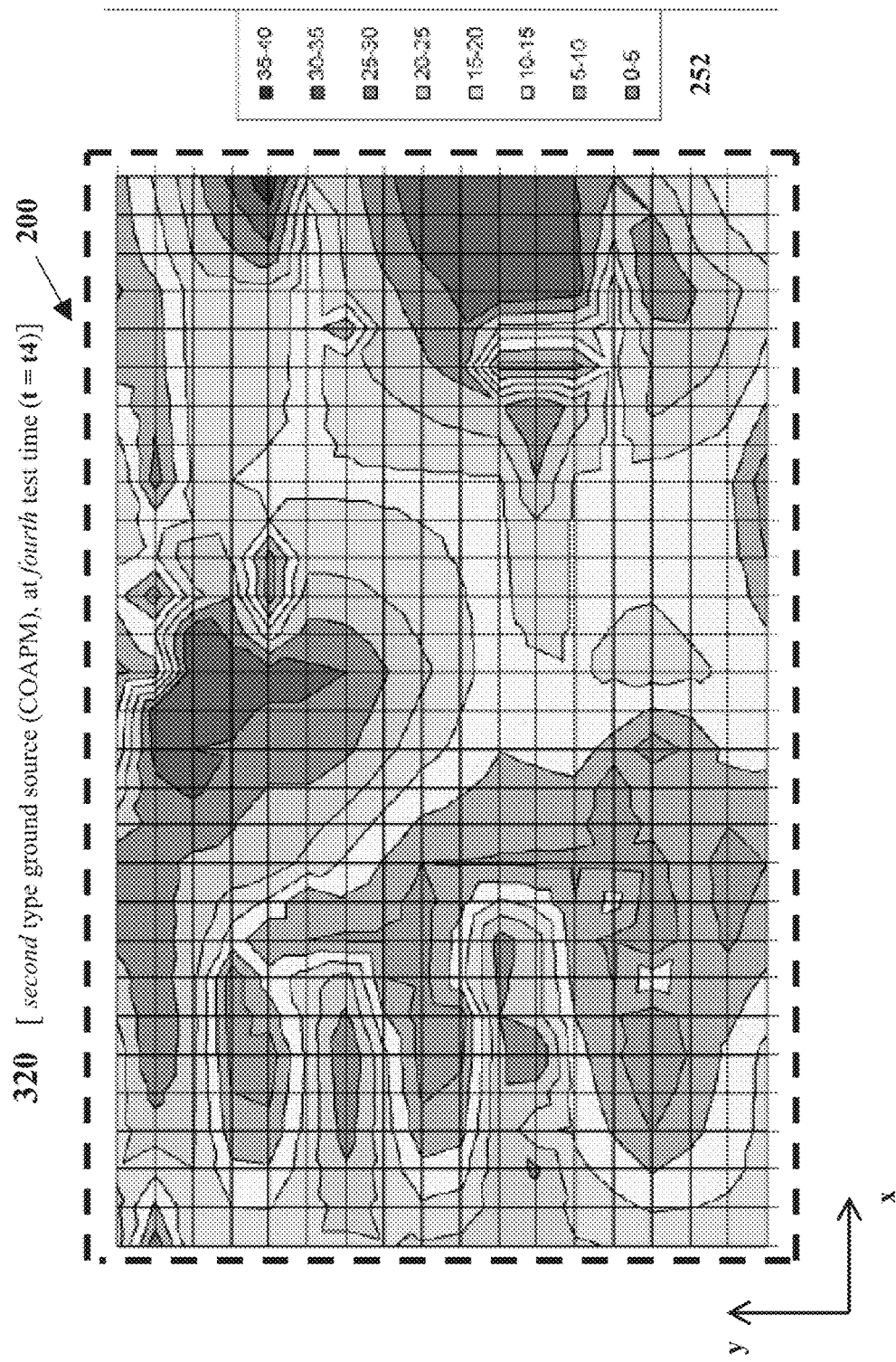

FIGS. 12, 13, and 14 are schematic diagrams illustrating (simulated) exemplary real-time geographical distribution parametric data-information profiles (in the form of multi-color coded maps) 300, 310, and 320, respectively, of the contaminated outdoor air particulate matter concentration range (n1-n2 µg/m$^3$) associated with (originating from) the 'same' exemplary second type of ground source of contaminated outdoor air particulate matter (Ground Source (COAPM)), at the 'same' exemplary second, third, and fourth, test times (t=t2, t3, and t4, respectively) of FIGS. 9, 10, and 11, for the 'same' exemplary window or view within the first regional quadrant (RQ-1) presented in FIG. 6.

FIGS. 9-14 include the same reference x and y coordinate axes, and grid, presented in FIGS. 7 and 8, for indicating x and y directions and (arbitrary) distances (e.g., kilometers, miles, etc.) with respect to an arbitrarily positioned geographical origin of exemplary window or view 200. FIGS. 9-14 also include the same set or series 252 of different (color coded) levels (and corresponding values thereof) of the contaminated outdoor air particulate matter concentration range, quantitatively expressed in terms of n1-n2 µg/m$^3$, and associated with (originating from) the exemplary first or second type of ground source of contaminated outdoor air particulate matter (Ground Source (COAPM)).

In FIGS. 7-14, the exemplary first and second types of ground sources of contaminated outdoor air particulate matter (Ground Sources (COAPM)) are, for example, ground sources which correspond to two of the three above described exemplary categories [(1), (2), (3)] of ground sources of contaminated outdoor air particulate matter (Ground Sources (COAPM)). More specifically, the exemplary first type of ground source of contaminated outdoor air particulate matter (Ground Source (COAPM)), associated with FIGS. 7, 9, 10, and 11, is, for example, a ground source which corresponds to an exemplary category (1) ground source of contaminated outdoor air particulate matter (Ground Source (COAPM)), namely, any one of (1) actively used and operative infrastructure type ground sources, such as industrial, commercial, business, public, private, and residential, entities (building and building-like structures, especially, factories, manufacturing plants, power [coal and oil burning] plants, homes, food making and cooking establishments), and, vehicular roadways, bridges, and tunnels. Similarly, the exemplary second type of ground source of contaminated outdoor air particulate matter (Ground Source (COAPM)), associated with FIGS. 8, 12, 13, and 14, is, for example, a ground source which corresponds to an exemplary category (3) ground source of contaminated outdoor air particulate matter (Ground Source (COAPM)), namely, any one of (3) plant matter and ground surface type ground sources, such as trees, bushes, shrubs, plants, flowers, grass, and soil.

Operational Details for Implementing Exemplary Embodiments of the Method (10, FIG. 1) and System (30, FIG. 2) for Real-Time Monitoring and Parametric Profiling Contaminated Outdoor Air Particulate Matter Throughout a Region, Via Hyper-Spectral Imaging and Analysis As illustratively described above, the main Steps (a)-(d) of the exemplary embodiment of the method 10 (FIG. 1: 12, 14, 16, and 18; FIG. 3: 72, 74, 76, 78, 80, 82, and 84; FIG. 4: 92, 94, 96, 98, 100, 102, 104, and 110; and FIG. 5: 120) are performed via operation of the main components of the exemplary embodiments of the system 30 (FIGS. 2-4), namely, via operation of: (a) the plurality of local contaminated outdoor air particulate matter monitoring, sampling, and data-information processing stations [Local Stations-i (32, 34, 36, 38, 40, 42, and 44)] which include the corresponding plurality of local outdoor air particulate matter sampling units [OAPMSU], local hyper-spectral imaging and analysis units [HSIAU], and local data-information processing and communications units [LDIPCU]); (b) the plurality of local weather-meteorological conditions measuring units [WMCMU]; and (c) the global data-information processing and communications unit [GDIPCU] 50.

Real-Time Sampling the Contaminated Outdoor Air Particulate Matter, and Apparatus Therefor Real-time sampling the contaminated outdoor air particulate matter at each location is performed by using an appropriately configured and operative local outdoor air particulate matter sample collection apparatus. Accordingly, each of the plurality of local contaminated outdoor air particulate matter monitoring, sampling, and data-information processing stations [Local Stations-i (32, 34, 36, 38, 40, 42, and 44)] includes an outdoor air particulate matter sample collection apparatus, namely, the outdoor air particulate matter sampling unit [OAPMSU].

Real-time sampling the contaminated outdoor air particulate matter (COAPM), separately and simultaneously at each of the plurality of separate locations throughout the region (R-1) 20, for generating real-time samples of local contaminated outdoor air particulate matter each associated with a separate location in the region (R-1) 20, and providing the samples for real-time hyper-spectrally imaging and analyzing the contaminated outdoor air particulate matter (COAPM), at each location in the region (R-1) 20, are done by using an appropriately configured and operative outdoor air particulate matter sampling unit [OAPMSU]. Each local outdoor air particulate matter sampling unit [OAPMSU] includes main components: (i) an outdoor air capturing apparatus, (ii) an outdoor air particulate matter sample capturing (collecting) apparatus, (iii) an outdoor air particulate matter sample holding and transporting (forwarding) apparatus, and (iv) a power supply and control apparatus, such as an electrical power supply and control circuitry.

In the local outdoor air particulate matter sampling unit [OAPMSU], the outdoor air capturing apparatus is for capturing (pumping or sucking in) the outdoor air from the local environment. An exemplary outdoor air capturing apparatus is a pumping device, including a pump, for pumping in the outdoor air, and pipes (tubes) for guiding the outdoor air into the pump.

The outdoor air particulate matter sample capturing (collecting) apparatus is for capturing (collecting) samples of the outdoor air particulate matter from the outdoor air which is captured by the outdoor air capturing apparatus. An exemplary outdoor air particulate matter sample capturing (collecting) apparatus is an air filtering device, including air filters (also functioning as solid substrates), for filtering the outdoor air in a manner such that samples of the outdoor air particulate matter are captured (collected) and held onto the air filters. Suitable air filters are made or composed of various different materials, singly or in combination. Exemplary materials are: (i) synthetic or synthetic-based materials, such as plastics, for example, Teflon®; and (ii) natural or natural-based materials, such as silicon based materials, for example, quartz, and fiberglass (material consisting of extremely fine glass fibers).

The outdoor air particulate matter sample holding and transporting (forwarding) apparatus is for holding the (filter) samples of the outdoor air particulate matter, and for transporting (forwarding) the (filter) samples of the outdoor air particulate matter from the local outdoor air particulate matter sampling unit [OAPMSU] to the local hyper-spectral imaging and analysis units [HSIAU]. An exemplary outdoor air particulate matter sample holding and transporting (forwarding) apparatus is a mobile supporting and conveying device, such as a conveyor.

The power supply and control apparatus is for supplying electrical power to, and for controlling, the local outdoor air particulate matter sampling unit [OAPMSU], in general, and in particular, the outdoor air capturing apparatus (e.g., pump), and the outdoor air particulate matter sample holding and transporting (forwarding) apparatus (e.g., conveyor). The power supply and control apparatus includes an electrical power supply and control circuitry.

Additional details regarding real-time sampling contaminated outdoor air particulate matter (COAPM), and providing the samples for real-time hyper-spectrally imaging and analyzing the contaminated outdoor air particulate matter (COAPM), are illustratively described [1] by the same applicant/assignee of the present invention. Additional details regarding structure and function (operation) of an exemplary outdoor air particulate matter sampling unit [OAPMSU], which is particularly suitable for implementing exemplary embodiments of the present invention, with respect to real-time sampling contaminated outdoor air particulate matter (COAPM), and providing the samples for real-time hyper-spectrally imaging and analyzing the contaminated outdoor air particulate matter (COAPM), are illustratively described [8] by the same applicant/assignee of the present invention.

Real-Time Hyper-Spectral Imaging and Analyzing, the Contaminated Outdoor Air Particulate Matter, and Apparatus Therefor (Local Hyper-Spectral Imaging and Analysis Units [HSIAU])

Separately and simultaneously at each of the plurality of separate locations throughout the region (R-1) 20, real-time samples of local contaminated outdoor air particulate matter (COAPM) each associated with a separate location in the region (R-1) 20, are transported (forwarded) from the local outdoor air particulate matter sampling unit [OAPMSU] to the local hyper-spectral imaging and analysis units [HSIAU].

Hyper-spectral image data and information of the local contaminated outdoor air particulate matter (COAPM) are generated and collected during real-time. During the hyper-spectral imaging, an object or objects (e.g., in a sample of the contaminated outdoor air particulate matter (COAPM)), typically as part of a scene (i.e., of the samples), is/are exposed to electromagnetic radiation, followed by generation and collection of multiple spectral (i.e., hyper-spectral) images, via a single field of view, or via a plurality of fields of view, of the object(s) emitting electromagnetic radiation having wavelengths (or frequencies, energies) associated with different selected (relatively narrow) portions or bands, or bands therein, of an entire spectrum emitted by the object(s).

Hyper-spectral images of the object(s) are generated and collected from the object(s) emitting electromagnetic radiation having wavelengths (or frequencies, energies) associated with one or more of the following portions or bands, or bands therein, of an entire spectrum emitted by the object(s): the ultra-violet (UV) band, spanning the wavelength range of about 100-350 nanometers; the visible (VIS) band, spanning the wavelength range of about 400-700 nanometers [blue band: about 400-500 nm, green band: about 500-600 nm, red band: about 600-700 nm]; the infra-red (IR) band, spanning the wavelength range of about 800-1200 nanometers; and the deep infra-red band, spanning the wavelength range of about 3-12 microns. Such hyper-spectral images generated by, and collected from, the imaged object(s), correspond to spectral 'fingerprint' or 'signature' pattern types of identification and characterization of the imaged object(s), which, subsequently, are processed and analyzed in accordance with exemplary embodiments of the present invention.

Real-time sampling, and hyper-spectrally imaging and analyzing, the contaminated outdoor air particulate matter (COAPM), separately and simultaneously at each of the plurality of separate locations throughout the region (R-1) 20, for generating a corresponding plurality of real-time local contaminated outdoor air particulate matter data-information packages each associated with a separate location in the region (R-1) 20, and real-time processing and analyzing the real-time local contaminated outdoor air particulate matter data-information packages, at each location in the region (R-1) 20, are done by using an appropriately configured and operative hyper-spectral imaging and analysis unit [HSIAU]. Such a hyper-spectral imaging and analysis unit [HSIAU] is of appropriate design and construction, and operates, for performing main tasks of generating, detecting, measuring, acquiring, collecting, processing, analyzing, and displaying, a wide variety of different types of hyper-spectral image data and information of the contaminated outdoor air particulate matter (COAPM) at each location in the region (R-1) 20.

For performing these tasks, each of the plurality of local contaminated outdoor air particulate matter monitoring, sampling, and data-information processing stations [Local Stations-i (32, 34, 36, 38, 40, 42, and 44)] includes a 'generalized' hyper-spectral imaging and analysis unit [HSIAU] that includes as main components: (i) an illuminating apparatus, for generating and optically supplying electromagnetic radiation to individual objects among a plurality, collection, or ensemble, of several objects (i.e., entities, materials, substances, or structures) of (included or contained in) the surroundings or place of each scene (e.g., in samples of the contaminated outdoor air particulate matter (COAPM)) which is imaged in a plurality of hyper-spectral images, via one or more fields of view, for forming illuminated objects; (ii) a hyper-spectral imaging apparatus, for optically detecting the affected energies or emission beams emitted by, and emerging from, illuminated objects, and for generating optical forms of hyper-spectral images of the illuminated objects of the imaged scenes; (iii) a hyper-spectral image converting apparatus, for converting the optical forms of the hyper-spectral images to corresponding electronic forms of the hyper-spectral images; and (iv) a data-information processing and analyzing apparatus, for programming, processing, analyzing, and storing the various data and information, or/and signals thereof, of the units and components thereof, of the hyper-spectral imaging and analysis unit [HSIAU].

Optionally, each hyper-spectral imaging and analysis unit [HSIAU] further includes a synchronizing apparatus, for synchronizing overall operation and operating parameters of the apparatuses and components thereof, singly, in combination with each other, and, optionally, in combination with peripheral, auxiliary, or/and external, equipment (hardware or/and software) and, operation and operating parameters thereof.

Optionally, each hyper-spectral imaging and analysis unit [HSIAU] further includes an operator workstation apparatus, for enabling an operator to send operating commands, instructions, and data, to the data-information processing and analyzing apparatus, as well as to receive data and information therefrom, during real-time (on-line) or/and during non-real time (off-line) operation.

In each hyper-spectral imaging and analysis unit [HSIAU], each of the illuminating apparatus, the hyper-spectral imaging apparatus, and the hyper-spectral image converting apparatus, is operatively (electrically or/and electronically) connected to the data-information processing and analyzing apparatus, and to the other apparatuses, as needed, and optionally, to the optional synchronizing apparatus, or/and to the optional operator workstation apparatus, via appropriate data and information input/output (I/O) signal paths and junctions.

Each of the several above stated main components, and optional components, of the hyper-spectral imaging and analysis unit [HSIAU], is of design and construction, and operates, for providing the 'ultimate' combination of exceptionally high accuracy, 'and' high precision (reproducibility), 'and' high sensitivity, 'and' at high speed (short time scale), all at the same time (i.e., simultaneously), be it during real-time or during non-real time, in an optimum or highly efficient manner. Additionally, each of the several above stated main components, and optional components, of the hyper-spectral imaging and analysis unit [HSIAU] provides high performance, including, for example, relatively high resolution at high speed (short time scale), along with providing low false positive and false negative error rates.

In general, the hyper-spectral imaging and analysis unit [HSIAU] includes a hyper-spectral imaging apparatus that is essentially any type of device, mechanism, or assembly, which is capable of operating as just described. For example, the hyper-spectral imaging apparatus is designed, constructed, and operative, as an optical interferometer, which optically detects affected energy or emission beams, emitted by, and emerging from, illuminated objects, in the form of whole images, and then optically processes the whole images for generating optical forms of hyper-spectral images of the illuminated objects of (included or contained in) the imaged scenes of the samples of contaminated outdoor air particulate matter (COAPM).

For example, the hyper-spectral imaging apparatus is appropriately designed, constructed, and operative, according to a high performance, high resolution high speed (short time scale) hyper-spectral mode of hyper-spectral imaging and analysis, for example, as illustratively described [3] by the same applicant/assignee of the present invention. Such a hyper-spectral imaging apparatus has spectral and spatial resolutions on the order of less than about 30 nm, for example, on the order of about 5 nm. As disclosed therein, such a hyper-spectral imaging apparatus involves the use of a specially designed, constructed, and operative, piezoelectric optical interferometer, based on using piezoelectric technology with closed loop control and analysis algorithms, for enabling real time high resolution high speed nanometer accuracy movement of a movable mirror in the optical interferometer, along with using a specially designed and constructed optical interferometer mount as part of the optical interferometer, for achieving high thermo-mechanical stability of mounted optical interferometer components during real time hyper-spectral imaging of objects.

As further disclosed therein, operation of such a hyper-spectral imaging apparatus involves using a specially designed optical path distance (OPD) calibration procedure, and image processing software algorithms, for enabling high speed (on the order of less than about 100 milliseconds scanning per image) generating of high spectral and spatial resolution (for example, on the order of less than about 5 nm) interferogram images, which in turn would be used for synthesizing and analyzing high resolution highly reproducible three-dimensional hyper-spectral (cube) images of objects of (included or contained in) the imaged scenes.

Alternatively, for example, the hyper-spectral imaging apparatus is designed, constructed, and operative, as a dispersion prism, which optically detects the affected energies or emission beams emitted by, and emerging from, the illuminated objects, in the form of single lines of a whole image, and then optically processes the single lines of the whole images for generating optical forms of hyper-spectral images of the illuminated objects of the imaged scenes.

The hyper-spectral imaging apparatus can include components designed, constructed, and operative, according to multiplexing/demultiplexing (demux) fiber optics technology. In particular, an exemplary embodiment of such a hyper-spectral imaging apparatus includes a 'detecting' bundle of a plurality of individual or demultiplexed flexible fiber optic tubes which is operatively connected to an illuminating bundle of a plurality of flexible fiber optic tubes of an illuminating unit. The detecting bundle of flexible fiber optic tubes is positioned relative to the output of the illuminating apparatus and to objects of (included or contained in) a scene, in a manner such that the detecting bundle of flexible fiber optic tubes detects, receives, and then transmits (forwards), individual or demultiplexed optically detected affected energies or emission beams, emitted by, and emerging from, the illuminated objects, in the form of whole images, or in the form of single lines of a whole image, to other components of the hyper-spectral imaging apparatus, which then optically process the whole images, or the single lines of whole images, respectively, for generating optical forms of hyper-spectral images of illuminated objects of the imaged scenes.

In each local hyper-spectral imaging and analysis unit [HSIAU], the hyper-spectral image converting apparatus is for converting the optical forms of the hyper-spectral images to corresponding electronic forms of the hyper-spectral images of the illuminated objects in the imaged scenes. In general, the hyper-spectral image converting apparatus is essentially any type of device, mechanism, or assembly, which is capable of operating as just described. For example, the hyper-spectral image converting apparatus is designed, constructed, and operative, as a plurality of line detectors/cameras, or alternatively, as a CCD (charged coupled detector) type of detector/camera, or alternatively, as a diode array type of detector/camera, each of which converts the optical forms of the hyper-spectral images to corresponding electronic forms of the hyper-spectral images of the illuminated objects in the imaged scenes. For example, the image exposure time of the detector/camera device, mechanism, or assembly, of the hyper-spectral image converting apparatus is, for example, in a range of between about 0.1 millisecond and about 5 milliseconds, and the image conversion time of the spectral image converting unit is, for example, in a range of between about 1 millisecond and about 10 milliseconds.

In each local hyper-spectral imaging and analysis unit [HSIAU], the data-information processing and analyzing apparatus is for programming, processing, analyzing, and storing the various data and information, or/and signals thereof, of the apparatuses and components thereof, of the hyper-spectral imaging and analysis unit [HSIA]. Accordingly, the various data and information, or/and signals thereof, of the apparatuses and components thereof, of the hyper-spectral imaging and analysis unit [HSIA] are programmed, processed, analyzed, and stored, by the data-information processing and analyzing apparatus.

In particular, data and information, or/and signals thereof, of the illuminating apparatus, of the hyper-spectral imaging apparatus, and of the hyper-spectral image converting apparatus, and optionally, of the optional synchronizing apparatus, and optionally, of the optional operator workstation apparatus, of the hyper-spectral imaging and analysis unit [HSIA] which are sent and received via appropriate data and information input/output (I/O) signal paths and junctions, are programmed, processed, analyzed, and stored by the data-information processing and analyzing apparatus.

More specifically, the data-information processing and analyzing apparatus is for programming, processing, analyzing, and storing, the various data and information, or/and signals thereof, associated with: (1) incident electromagnetic radiation generated and optically supplied by the illuminating apparatus to the objects of (included or contained in) the imaged scenes; (2) affected energies or emission beams emitted by, and emerging from, the illuminated objects, which are optically detected and processed by the hyper-spectral imaging apparatus, for generating optical forms of hyper-spectral images of the illuminated objects of the imaged scenes; and (3) optical forms of the hyper-spectral images of the illuminated objects, which are generated by the hyper-spectral imaging apparatus, and are converted to corresponding electronic forms of the hyper-spectral images, by the hyper-spectral image converting apparatus.

The data-information processing and analyzing apparatus is also for programming, processing, analyzing, and storing data and information, or/and signals thereof, associated with optional, and preferable, synchronization of overall operation and operating parameters of the apparatuses and components thereof, of the hyper-spectral imaging and analysis unit [HSIA], singly, in combination with each other, and, optionally, in combination with peripheral, auxiliary, or/and external, equipment (hardware or/and software) and, operation and operating parameters thereof, by the optional synchronizing apparatus.

The data-information processing and analyzing apparatus includes all the necessary software, including operatively connected and functioning written or printed data, in the form of software programs, software routines, software sub-routines, software symbolic languages, software code, software instructions or protocols, software algorithms, or/and a combination thereof, and includes all the necessary hardware, for programming, processing, analyzing, and storing data and information, or/and signals thereof, which are associated with performing the above described functions and operations of the local hyper-spectral imaging and analysis unit [HSIA], and which are associated with implementing and practicing the herein illustratively described exemplary embodiments of the present invention.

In particular, the data-information processing and analyzing apparatus includes all the necessary software for performing the steps or procedures of exemplary embodiments of the method 10, during real time or/and during non-real time (off-line), for optimally and highly efficiently, integrating the two main activities of processing, and analyzing, hyper-spectral image data and information, namely, (i) automatic (i.e., computerized) data and information manipulating, handling, or/and moving, types of procedures or/and operations, and, (ii) automatic (i.e., computerized) data and information analyzing, identifying (recognizing), discriminating, comparing, filtering, sorting, quantifying, characterizing, and classifying, types of procedures or/and operations.

Additionally, exemplary embodiments of the method 10 and system 30 for real-time monitoring and parametric profiling contaminated outdoor air particulate matter throughout a region, via hyper-spectral imaging and analysis, are implementable or operable for being generally applicable to, and integratable with, various different types or kinds of physical hardware equipment and instrumentation, and, (computer) software, which comprise a given hyper-spectral imaging and analysis unit [HSIA] which is operable during real time or/and during non-real time.

Exemplary embodiments of the method 10 and system 30 are implementable by including the use of the same or/and specially modified methodologies of automatic pattern recognition (APR) and classification types of spectral or hyper-spectral image data and information processing and analyzing which are described in same applicant/assignee prior disclosures [e.g., 1-8], and described in references cited therein. This is especially the case where, for example, a particular biological, physical, or/and chemical, object (entity, material, substance, or structure) of (included or contained in) an imaged scene either is, or contains, particulate matter or particulate-like matter (i.e., matter having particle-like features, characteristics, properties, and behavior).

For performing the automatic pattern recognition (APR) and classification types of hyper-spectral image data and information processing and analyzing, there is applying one or more image analysis algorithms, such as detection, pattern recognition and classification, and/or decision image analysis algorithms, to the hyper-spectral image data and information. The imaged scenes include or contain hyper-spectral image data and information relating to the imaged object(s) (of the contaminated outdoor air particulate matter (COAPM)), particularly in the form of spectral representations, such as spectral fingerprint or signature pattern types of identification and characterization, of the imaged object(s).

In each of the plurality of local contaminated outdoor air particulate matter monitoring, sampling, and data-information processing stations [Local Stations-i (32, 34, 36, 38, 40, 42, and 44)], the data-information processing and analyzing apparatus of the hyper-spectral imaging and analysis unit [HSIA] is operatively connected to and in communication with, via appropriate data and information input/output (I/O) signal paths and junctions, the respective local data-information processing and communications units [LDIPCU], which, in turn, is operatively connected to and in communication with, via the wired or/and wireless (data/information input/output (I/O)) communications network (including appropriate signal paths and junctions) [dashed lines network shown in FIGS. 2, 3, and 4], the global data-information processing and communications unit [GDIPCU] 50.

Real-Time Measuring Outdoor Weather-Meteorological Conditions, and Apparatus Therefor (Local Weather-Meteorological Conditions Measuring Units [WMCMU])

Real-time measuring outdoor weather-meteorological conditions (of the outdoor air), separately and simultaneously at the plurality of separate locations throughout the region (R-1) 20, in a manner synchronized with the real-time sampling, imaging, and analyzing, of the contaminated outdoor air particulate matter (COAPM), for generating a corresponding plurality of real-time local outdoor weather-meteorological conditions data-information packages each associated with a separate location in the region (R-1) 20, and real-time processing and analyzing the real-time local contaminated outdoor air particulate matter data-information packages, at each location in the region (R-1) 20, are done by using an appropriately configured and operative weather-meteorological conditions measuring unit [WMCMU]. Such a local weather-meteorological conditions measuring unit [WMCMU] is of appropriate design and construction, and operates, for performing main tasks of detecting, measuring, acquiring, collecting, processing, analyzing, generating, and displaying, a wide variety of different types of (local) weather-meteorological conditions data and information of the outdoor air, at each location in the region (R-1) 20.

Exemplary weather-meteorological conditions data and information of the outdoor air, at each location, are: (a) temperature; (b) humidity (water vapor content) [e.g., absolute, relative]; (c) (barometric) pressure; (d) wind (movement [speed, direction, patterns] thereof); (e) precipitation (type [e.g., rain, snow, sleet] thereof), extent (amount, rate) thereof, and movement [speed, direction, patterns] thereof); and (f) clouds (type [e.g., cumulus (Cu), stratocumulus (Sc), nimbostratus (Ns), stratus (St)] thereof, extent (coverage) thereof, and movement [speed, direction, patterns] thereof).

For performing these tasks, each of the plurality of local contaminated outdoor air particulate matter monitoring, sampling, and data-information processing stations [Local Stations-i (32, 34, 36, 38, 40, 42, and 44)] includes a local outdoor air weather-meteorological conditions measuring unit [WMCMU] that includes any number and combination (i.e., at least one) of the following main components (outdoor air parametric measuring apparatuses): (i) an outdoor air temperature measuring apparatus; (ii) an outdoor air (absolute or/and relative) humidity measuring apparatus; (iii) an outdoor air (barometric) pressure measuring apparatus; (iv) an outdoor air wind (movement) measuring apparatus; (v) an outdoor air precipitation (type, extent, and movement) measuring apparatus; or/and (vi) an outdoor air cloud (type, extent, and movement) measuring apparatus. The outdoor air parametric measuring apparatuses (i)-(vi) continuously or/and periodically measure the various respective outdoor air weather-meteorological conditions data and information, which are then sent, via the local outdoor air weather-meteorological conditions measuring unit [WMCMU], to the local data-information processing and communications unit [LDIPCU]. Each of the outdoor air parametric measuring apparatuses (i)-(vi) are readily commercially available for inclusion in the local outdoor air weather-meteorological conditions measuring unit [WMCMU] of each respective local contaminated outdoor air particulate matter monitoring, sampling, and data-information processing stations [Local Stations-i (32, 34, 36, 38, 40, 42, and 44)].

In each of the plurality of local contaminated outdoor air particulate matter monitoring, sampling, and data-information processing stations [Local Stations-i (32, 34, 36, 38, 40, 42, and 44)], the main components (i)-(vi) of the local outdoor air weather-meteorological conditions measuring unit [WMCMU], singly or in combination, are operatively connected to and in communication with, via appropriate data and information input/output (I/O) signal paths and junctions, the respective local data-information processing and communications units [LDIPCU], which, in turn, is operatively connected to and in communication with, via the wired or/and wireless (data/information input/output (I/O)) communications network (including appropriate signal paths and junctions) [dashed lines network shown in FIGS. 2, 3, and 4], the global data-information processing and communications unit [GDIPCU] 50. Each respective local data-information processing and communications units [LDIPCU] is involved in performing various tasks of main Step (b), namely, real-time measuring outdoor weather-meteorological conditions, separately and simultaneously at the plurality of separate locations, in a manner synchronized with the real-time sampling, imaging, and analyzing, for generating a corresponding plurality of real-time local outdoor weather-meteorological conditions data-information packages each associated with a separate location. Additionally, each respective local data-information processing and communications units [LDIPCU] operates along with the global data-information processing and communications unit [GDIPCU] 50 for performing various tasks of main Step (c) which involve the real-time processing and analyzing the real-time local outdoor weather-meteorological conditions data-information packages.

Real-Time Processing and Analyzing the Real-Time Local Contaminated Outdoor Air Articulate Matter Data-Information Packages and the Real-Time Local Outdoor Weather-Meteorological Conditions Data-Information Packages; and Real-Time Processing and Analyzing the Set of Real-Time Local Geographical Distribution Parametric Data-Information Profiles of the Contaminated Outdoor Air Particulate Matter, Via the Global Data-Information Processing and Communications Unit [GDIPCU]

Main Steps (c) and (d) of the exemplary embodiment of the method 10 (FIG. 1: 16 and 18; FIG. 3: 72, 74, 76, 78, 80, 82, and 84; FIG. 4: 92, 94, 96, 98, 100, 102, 104, and 110; and FIG. 5: 120), namely, (c) real-time processing and analyzing the real-time local contaminated outdoor air particulate matter data-information packages and the real-time local outdoor weather-meteorological conditions data-information packages, for real-time generating a set of real-time local geographical distribution parametric data-information profiles of the contaminated outdoor air particulate matter, showing real-time local geographical distributions of qualitative or/and quantitative parameters of the contaminated outdoor air particulate matter associated with each separate location, via global data-information processing and communications unit [GDIPCU] 50 (FIGS. 2-4); and (d) real-time processing and analyzing the set of real-time local geographical distribution parametric data-information profiles of the contaminated outdoor air particulate matter, for real-time generating a set of real-time regional geographical distribution parametric data-information profiles of the contaminated outdoor air particulate matter, showing real-time regional geographical distributions of the qualitative or/and quantitative parameters of the contaminated outdoor air particulate matter throughout the region, via global data-information processing and communications unit [GDIPCU] 50, are performed by using any number of various different types or kinds of data-information processing and analyzing techniques and procedures, which are applicable to processing and analyzing data and information relating to, and characterizing, contaminated outdoor air, in general, and contaminated outdoor air particulate (or/and particulate-like) matter, and components thereof, in particular, and which can also be applied to processing and analyzing, and accounting for, hyper-spectral imaging data and information of particulate (or/and particulate-like) matter.

Two exemplary categories of such data-information processing and analyzing techniques and procedures are: (1) bottom-up (ground to air) based data-information processing and analyzing techniques and procedures, also known and referred to as source based, or chemical mass balance [CMB] based, or output (emission) inventory based, data-information processing and analyzing techniques and procedures; and (2) top-down (air to ground) based data-information techniques and procedures, also known and referred to as receptor based source apportionment data-information processing and analyzing techniques and procedures.

Bottom-up (ground-air) based data-information processing and analyzing techniques and procedures are based on identifying ground sources of contaminated outdoor air and their output (emission) factors, which can be combined with weather-meteorological conditions data and information (e.g., weather patterns) for predicting composition and levels of contaminated outdoor air. Major limitations of the bottom-up (ground-air) based approach are that they are not derived from 'actual' air samples, and the ground sources of the contaminated air must be pre-identified. Additionally, spectral and temporal resolutions of results obtained therefrom are significantly less than spectral and temporal resolutions of results obtained from top-down (air-ground) based data-information techniques and procedures.

Top-down (air-ground) based data-information techniques and procedures are based on sampling air in a given area or region, and then inferring the most likely ground sources of the contaminated outdoor air by comparing, and contrasting, the various chemical, physical, or/and biological, characteristics and parameters of the air samples to those of the ground sources. This results in quantifying the relative contributions of the different ground sources to the contaminated outdoor air. Currently used top-down (air-ground) based data-information techniques and procedures are relatively complicated, expensive, and slow, to implement, especially for large scale commercial or industrial applications.

Ideally, results obtained by applying the above described two approaches should agree with each other, but this is rarely the case for most applications. Proper analysis of the differences between the two approaches, and efforts to reconcile between them attempts to provide results which are in acceptable agreement. Top-down (air-ground) based data-information techniques and procedures are more commonly used in most countries. Moreover, using this approach is a good way to supplement and improve results obtained by applying bottom-up (ground-air) based data-information processing and analyzing techniques and procedures, as well as for either supporting or questioning the validity of such results, by being based on obtaining, processing, and analyzing 'actual' samples of contaminated air. For example, top-down (air-ground) based approaches have occasionally revealed over/underestimations of certain air contaminants as calculated according to bottom-up (ground-air) based approaches. Such data and information is extremely important when it comes to applications which are based on, or/and, involve monitoring, profiling, maintaining, operating and controlling, developing, and planning, infrastructure and vehicular traffic, of human populated regions, where such applications include the important objective of achieving and maintaining high quality levels of outdoor air of the human populated regions, which, in turn, contributes to achieving and maintaining high quality levels of public health, welfare, and activities throughout the human populated regions.

Exemplary embodiments of the present invention are implemented by using top-down (air-ground) based (receptor based source apportionment) data-information techniques and procedures. Some exemplary embodiments of the present invention are implemented by accounting for (e.g., comparing/contrasting) data and information obtained from, or/and relating to, bottom-up (ground-air) based (source based, chemical mass balance [CMB] based, output (emission) inventory based) data-information processing and analyzing techniques and procedures.

In some exemplary embodiments of the present invention, there is development of a contaminated outdoor air particulate matter profile (source) library (database), according to the following procedure:

collecting samples of the contaminated outdoor air particulate matter;

creating a 'scenario', for eventual storing of hyper-spectral image data and information of the contaminated outdoor air particulate matter, based on exemplary parameters of: (i) magnifying power, (ii) area of the region of interest (ROI) in each scene, (iii) exposure time, and (iv) spectral output (e.g., intensity, shape);

hyper-spectrally imaging the collected samples of the contaminated outdoor air particulate matter, for generating hyper-spectral image data and information;

setting of a target detection level, which enables separating target pixels from background pixels of a hyper-spectral image;

creating a database, which includes the hyper-spectral image data and information;

identifying targets in the hyper-spectral images of the contaminated outdoor air particulate matter samples; targets correspond to contaminated outdoor air particulate matter, and components thereof, in the outdoor air which originate from the above described various different types or kinds of ground sources of contaminated outdoor air particulate matter;

repeating the above after a pre-determined time interval, for example, at least once a day, for a pre-determined period of time, for example, a week, or a month.

The contaminated outdoor air particulate matter profile (source) library (database) is then usable for performing above illustratively described main Steps (c) and (d) of the exemplary embodiment of the method 10 (FIG. 1: 16 and 18; FIG. 3: 72, 74, 76, 78, 80, 82, and 84; and FIG. 4: 92, 94, 96, 98, 100, 102, 104, and 110).

Main Steps (c) and (d) of the exemplary embodiment of the method 10 (FIG. 1: 16 and 18; FIG. 3: 72, 74, 76, 78, 80, 82, and 84; FIG. 4: 92, 94, 96, 98, 100, 102, 104, and 110; and FIG. 5: 120), for real-time monitoring and parametric profiling contaminated outdoor air particulate matter throughout a region, via hyper-spectral imaging and analysis, can be performed by including the use of highly specific, 'additional' data-information processing and analyzing techniques or/and procedures, for the purpose of refining and improving the accuracy and precision (reproducibility) of the results generated by these main steps.

A first exemplary 'additional' data-information processing and analyzing technique or/and procedure is based on accounting for, and using, (continuously or periodically updated) real-time local (bottom-up [ground to air] type) inventory data and information of the exemplary categories of the ground sources of contaminated outdoor air particulate matter (Ground Sources (COAPM)) throughout the region (R-1) 20, namely, of: (1) actively used and operative infrastructure type ground sources, such as industrial, commercial, business, public, private, and residential, entities (building and building-like structures, especially, factories, manufacturing plants, power [coal and oil burning] plants, homes, food making and cooking establishments), and, vehicular roadways, bridges, and tunnels; (2) actively used and operative vehicular traffic type ground sources, such as automobiles, buses, trucks, vans, motorbikes, and scooters; and (3) plant matter and ground surface type ground sources, such as trees, bushes, shrubs, plants, flowers, grass, and soil.

This first exemplary 'additional' data-information processing and analyzing technique or/and procedure accounts for, and uses, (continuously or periodically updated) real-time local (bottom-up [ground to air] type) inventory data and information focusing on, for example, (physical and structural) topographical data and information about or/and relating to: (1) the actively used and operative infrastructure type ground sources, such as industrial, commercial, business, public, private, and residential, entities (building and building-like structures, especially, factories, manufacturing plants, power [coal and oil burning] plants, homes, food making and cooking establishments), and, vehicular roadways, bridges, and tunnels, throughout the region (R-1) 20. Such topographical data and information may include: (i) detailed, precise descriptions of the actively used and operative infrastructure type ground sources, or/and (ii) pictorial or/and graphical representations of external features of the actively used and operative infrastructure type ground sources, which can also include data and information indicating their relative positions, geometrical dimensions, elevations, or/and densities (i.e., quantity or number per area), throughout the region (R-1) 20.

This first exemplary 'additional' data-information processing and analyzing technique or/and procedure, alternatively or additionally, accounts for, and uses, (continuously or periodically updated) real-time local (bottom-up [ground to air] type) inventory data and information focusing on, for example, (physical and structural) topographical data and information about or/and relating to, for example, (continuously or periodically updated) real-time local vehicular traffic conditions or/and patterns of: (2) the actively used and operative vehicular traffic type ground sources, such as automobiles, buses, trucks, vans, motorbikes, and scooters, throughout the region (R-1) 20. Such topographical data and information may include: (i) detailed, precise descriptions of the actively used and operative vehicular traffic type ground sources, or/and (ii) pictorial or/and graphical representations of external features of the actively used and operative vehicular traffic type ground sources, which can also include data and information indicating their relative positions, geometrical dimensions, or/and densities (i.e., quantity or number per area), throughout the region (R-1) 20.

A second exemplary 'additional' data-information processing and analyzing technique or/and procedure is based on accounting for, and using, (continuously or periodically updated) real-time local (bottom-up [ground to air] type) inventory data and information of atmospheric gas content, particularly with respect to potential gas phase contaminants in the outdoor air, throughout the region (R-1) 20.

The (continuously or periodically updated) real-time local (bottom-up [ground to air] type) inventory data and information of the first and second exemplary 'additional' data-information processing and analyzing techniques or/and procedures are obtained from various different entities, for example, public (governmental) entities [e.g., national, regional, local, public health agencies, departments, offices, institutes] or/and private entities [e.g., private institutes]. These entities compile and issue such real-time local inventory type data and information for the above stated exemplary categories of ground sources of the contaminated outdoor air particulate matter (Ground Sources (COAPM)), particularly, with respect to, in view of, establishing, or/and maintaining threshold levels thereof which are suitable for human (internal or/and external) contact with (exposure to) the contaminated outdoor air particulate matter, as part of working towards achieving and maintaining high quality levels of public health, welfare, and activities throughout human populated regions.

The preceding exemplary 'additional' data-information processing and analyzing techniques or/and procedures may be included as part of performing main Steps (c) and (d) of the exemplary embodiment of the method 10, for real-time monitoring and parametric profiling contaminated outdoor air particulate matter throughout a region, via hyper-spectral imaging and analysis, for the purpose of refining and improving the accuracy and precision (reproducibility) of the results generated by these main steps. Specifically, with respect to generating (continuously or periodically updated) interpolative type of data and information about the ground sources of contaminated outdoor air particulate matter (Ground Sources (COAPM)) throughout the region (R-1) 20, particularly, at locations in between the plurality of local contaminated outdoor air particulate matter monitoring, sampling, and data-information processing stations [Local Stations-i (32, 34, 36, 38, 40, 42, and 44)].

Moreover, in exemplary embodiments, results of the preceding exemplary 'additional' data-information processing and analyzing techniques or/and procedures may be correlated with each other. Specifically, results of the first exemplary additional data-information processing and analyzing technique or procedure which accounts for, and uses, (continuously or periodically updated) real-time local (bottom-up [ground to air] type) inventory data and information of the exemplary categories of the ground sources of contaminated outdoor air particulate matter (Ground Sources (COAPM)) throughout the region (R-1) 20, may be correlated with results of the second exemplary additional data-information processing and analyzing technique or procedure which accounts for, and uses, (continuously or periodically updated) real-time local (bottom-up [ground to air] type) inventory data and information of atmospheric gas content, particularly with respect to potential gas phase contaminants in the outdoor air, throughout the region (R-1) 20.

Another main aspect of some embodiments of the present invention relates to a method for real-time monitoring and regulating contaminated outdoor air particulate matter throughout a region, via hyper-spectral imaging and analysis.

Referring again to the drawings, FIGS. 15A and 15B are (block-type) flow diagrams of [main steps (a)-(d), and main steps (e)-(h), respectively] of an exemplary embodiment of the method (generally indicated as, and referred to by, reference number 400) for real-time monitoring and regulating contaminated outdoor air particulate matter throughout a region, via hyper-spectral imaging and analysis. In FIGS. 15A and 15B, each main step (procedure) of the exemplary embodiment shown is enclosed inside a separate block (frame) which is assigned a reference number. Accordingly, main steps (a), (b), (c), (d), (e), (f), (g), and (h), are enclosed inside of blocks (frames) 402, 404, 406, 408, 410, 412, 414, and 416, respectively. As shown in FIGS. 15A and 15B, the exemplary embodiment of the method 400 includes the following main steps or procedures, and, components and functionalities thereof.

Step (a) [402], identifying and classifying ground sources of the contaminated outdoor air particulate matter, wherein the ground sources are located throughout the region, for generating data-information of identified and classified ground sources of the contaminated outdoor air particulate matter throughout the region.

Step (b) [404], real-time sampling, and hyper-spectrally imaging and analyzing, the contaminated outdoor air particulate matter, separately and simultaneously at each of a plurality of separate locations throughout the region, for generating a corresponding plurality of real-time local contaminated outdoor air particulate matter data-information packages each associated with a separate location.

Step (c) [406], real-time measuring outdoor weather-meteorological conditions, separately and simultaneously at the plurality of separate locations, in a manner synchronized with the real-time sampling, imaging, and analyzing, for generating a corresponding plurality of real-time local outdoor weather-meteorological conditions data-information packages each associated with a separate location.

Step (d) [408], real-time processing and analyzing the real-time local contaminated outdoor air particulate matter data-information packages and the real-time local outdoor weather-meteorological conditions data-information packages, for real-time generating a set of real-time local geographical distribution parametric data-information profiles of the contaminated outdoor air particulate matter, showing real-time local geographical distributions of qualitative or/and quantitative parameters of the contaminated outdoor air particulate matter associated with each separate location, via a global data-information processing and communications unit.

Step (e) [410], real-time processing and analyzing the set of real-time local geographical distribution parametric data-information profiles of the contaminated outdoor air particulate matter, for real-time generating a set of real-time regional geographical distribution parametric data-information profiles of the contaminated outdoor air particulate matter, showing real-time regional geographical distributions of the qualitative or/and quantitative parameters of the contaminated outdoor air particulate matter throughout the region, via the global data-information processing and communications unit.

Step (f) [412], real-time processing and analyzing the set of real-time regional geographical distribution parametric data-information profiles of the contaminated outdoor air particulate matter, in relation to the data-information of the identified and classified ground sources of the contaminated outdoor air particulate matter, for determining at least one indication of needing to change operating conditions and contaminated air output of one or more of the ground sources, via the global data-information processing and communications unit.

Step (g) [414], real-time communicating the at least one indication to an operator or/and controller of each of the one or more ground sources of the contaminated outdoor air particulate matter.

Step (h) [416], real-time changing, in a controlled manner, the operating conditions and the contaminated air output of the one or more ground sources, by each operator or controller, in response to the at least one indication, thereby regulating the contaminated outdoor air particulate matter throughout the region.

Another main aspect of some embodiments of the present invention relates to a system for real-time monitoring and regulating contaminated outdoor air particulate matter throughout a region, via hyper-spectral imaging and analysis.

Referring again to FIG. 2, the exemplary embodiment of the system 30 for real-time monitoring and parametric profiling contaminated outdoor air particulate matter throughout a region, via hyper-spectral imaging and analysis, shown for an exemplary region (R-1) 20, which is particularly suitable for implementing the exemplary embodiment of the method 10 presented in FIG. 1, is also particularly suitable for implementing the exemplary embodiment of the method 400 for real-time monitoring and regulating contaminated outdoor air particulate matter throughout a region, via hyper-spectral imaging and analysis, presented in FIGS. 15A and 15B. Accordingly, the exemplary embodiment of the system 30 is also referred to with respect to real-time monitoring and regulating contaminated outdoor air particulate matter throughout a region, via hyper-spectral imaging and analysis. For such implementation, as shown in FIG. 2, the exemplary embodiment of the system 30 includes the following main components and functionalities thereof.

A plurality of local contaminated outdoor air particulate matter monitoring, sampling, and data-information processing stations [Local Station-i, for i=1 to n local stations, where n is, for example, 7, corresponding to an exemplary seven local stations, having respective reference numbers 32, 34, 36, 38, 40, 42, and 44], configured for separately and simultaneously operating at a corresponding plurality of (i, for i=1 to n) separate locations throughout the region (R-1) 20, for real-time sampling, and hyper-spectrally imaging and analyzing the contaminated outdoor air particulate matter (via a corresponding plurality of local outdoor air particulate matter sampling units [OAPMSU], local hyper-spectral imaging and analysis units [HSIAU], and local data-information processing and communications units [LDIPCU]), separately and simultaneously at the plurality of separate locations, for generating a corresponding plurality of real-time local contaminated outdoor air particulate matter data-information packages each associated with a separate location.

A plurality of local weather-meteorological conditions measuring units [WMCMU], configured for separately and simultaneously operating at the plurality of separate locations, and for real-time measuring weather-meteorological conditions, separately and simultaneously at the plurality of separate locations, in a manner synchronized with the real-time sampling, imaging, and analyzing, for generating a corresponding plurality of real-time local outdoor weather-meteorological conditions data-information packages each associated with a separate location.

A global data-information processing and communications unit [GDIPCU] 50, configured for:

(i) classifying identified ground sources of the contaminated outdoor air particulate matter (Ground Sources (COAPM)), wherein the ground sources are located throughout the region, for generating data-information of identified and classified ground sources of the contaminated outdoor air particulate matter throughout the region;

(ii) real-time processing and analyzing the real-time local contaminated outdoor air particulate matter data-information packages and the real-time local outdoor weather-meteorological conditions data-information packages, for real-time generating a set of real-time local geographical distribution parametric data-information profiles of the contaminated outdoor air particulate matter, showing real-time local geographical distributions of qualitative or/and quantitative parameters of the contaminated outdoor air particulate matter associated with each separate location;

(iii) real-time processing and analyzing the set of real-time local geographical distribution parametric data-information profiles of the contaminated outdoor air particulate matter, for real-time generating a set of real-time regional geographical distribution parametric data-information profiles of the contaminated outdoor air particulate matter, showing real-time regional geographical distributions of the qualitative or/and quantitative parameters of the contaminated outdoor air particulate matter throughout the region (R-1) 20; and (iv) real-time processing and analyzing the set of real-time regional geographical distribution parametric data-information profiles of the contaminated outdoor air particulate matter, in relation to the data-information of the identified and classified ground sources of the contaminated outdoor air particulate matter (Ground Sources (COAPM)), for determining at least one indication of needing to change operating conditions and contaminated air output of one or more of the ground sources.

For implementing the exemplary embodiment of the method 400 presented in FIGS. 15A and 15B, the exemplary embodiment of the system 30 for real-time monitoring and regulating contaminated outdoor air particulate matter throughout a region, via hyper-spectral imaging and analysis, further includes (wired or/and wireless) communications equipment, configured for real-time (wired or/and wireless) communicating the at least one indication [of needing to change operating conditions and contaminated air output of one or more of the ground sources of the contaminated outdoor air particulate matter (Ground Sources (COAPM))] to a (human or/and machine type) operator or/and controller of each of the one or more ground sources of the contaminated outdoor air particulate matter, in order for each operator or controller of the one or more ground sources to real-time change, in a controlled manner, the operating conditions and contaminated air output thereof, in response to the at least one indication, thereby regulating the contaminated outdoor air particulate matter throughout the region (R-1) 20.

Operational Details for Implementing Exemplary Embodiments of the Method (400, FIGS. 15A-15B) and System (30, FIG. 2) for Real-Time Monitoring and Regulating Contaminated Outdoor Air Particulate Matter Throughout a Region, Via Hyper-Spectral Imaging and Analysis Identifying and Classifying Ground Sources of the Contaminated Outdoor Air Particulate Matter Main Step (a) of the exemplary embodiment of the method 400 (FIG. 15A: 404) is of identifying and classifying ground sources of the contaminated outdoor air particulate matter (Ground Sources (COAPM)), wherein the ground sources are located throughout the region (R-1) 20 (FIGS. 2-4), for generating data-information of identified and classified ground sources of the contaminated outdoor air particulate matter throughout the region (R-1) 20. For example, with reference to FIG. 2 (also applicable to FIGS. 3 and 4), this main step is performed by identifying and classifying the various different types or kinds, and quantities, of the ground sources of the contaminated outdoor air particulate matter (Ground Sources (COAPM)) which are located throughout the region (R-1) 20. As stated hereinabove, exemplary categories of such ground sources are: (1) actively used and operative infrastructure type ground sources, such as industrial, commercial, business, public, private, and residential, entities (building and building-like structures, especially, factories, manufacturing plants, power [coal and oil burning] plants, homes, food making and cooking establishments), and, vehicular roadways, bridges, and tunnels; (2) actively used and operative vehicular traffic type ground sources, such as automobiles, buses, trucks, vans, motorbikes, and scooters; and (3) plant matter and ground surface type ground sources, such as trees, bushes, shrubs, plants, flowers, grass, and soil.

Existing data and information, or/and newly obtained data and information, is obtained regarding the existence and operative states of such ground sources located throughout region (R-1) 20, particularly with respect to such ground sources being 'sources (originators)' (via emission, exhaustion, or output) of one or more contaminants (as defined hereinabove) that eventually end(s) up in outdoor air, which, as described above, either directly become contaminated outdoor air particulate matter, or first interact with particulate (or/and particulate-like) components of outdoor air which, together, then become contaminated outdoor air particulate matter.

Existing data and information regarding the existence and operative states of ground sources of the contaminated outdoor air particulate matter (Ground Sources (COAPM)) located throughout region (R-1) 20 are obtained from various different entities, for example, public (governmental) entities [e.g., national, regional, local, public health agencies, departments, offices, institutes] or/and private entities [e.g., private institutes]. Such entities compile and issue chemical 'source (originator)' (emission, exhaustion, or output) inventory type data and information for the above stated exemplary categories of ground sources of the contaminated outdoor air particulate matter (Ground Sources (COAPM)), particularly, with respect to, in view of, establishing, or/and maintaining threshold levels thereof which are suitable for human (internal or/and external) contact with (exposure to) the contaminated outdoor air particulate matter, as part of working towards achieving and maintaining high quality levels of public health, welfare, and activities throughout human populated regions.

Newly obtained data and information regarding the existence and operative states of such ground sources located throughout region (R-1) 20 can be obtained by contacting, and surveying, the various different types or kinds, and quantities, of ground sources of the contaminated outdoor air particulate matter (Ground Sources (COAPM)) which are located throughout the region (R-1) 20, for the purpose of compiling chemical 'source (originator)' (emission, exhaustion, or output) inventory type data and information for the above stated exemplary categories of ground sources of the contaminated outdoor air particulate matter (Ground Sources (COAPM)).

The main Steps (b)-(e) of the exemplary embodiment of the method 400 (FIG. 15A: 404, 406, and 408; and FIG. 15B: 410) for real-time monitoring and regulating contaminated outdoor air particulate matter throughout a region, via hyper-spectral imaging and analysis, are performed in a manner similar to the above illustratively described performance of the main Steps (a)-(d) of the exemplary embodiment of the method 10 (FIG. 1: 12, 14, 16, and 18; FIG. 3: 72, 74, 76, 78, 80, 82, and 84; FIG. 4: 92, 94, 96, 98, 100, 102, 104, and 110; and FIG. 5: 120) for real-time monitoring and parametric profiling contaminated outdoor air particulate matter throughout a region, via hyper-spectral imaging and analysis, via operation of the main components of the exemplary embodiments of the system 30 (FIGS. 2-4). Namely, via operation of: (a) the plurality of local contaminated outdoor air particulate matter monitoring, sampling, and data-information processing stations [Local Stations-i (32, 34, 36, 38, 40, 42, and 44)] which include the corresponding plurality of local outdoor air particulate matter sampling units [OAPMSU], local hyper-spectral imaging and analysis units [HSIAU], and local data-information processing and communications units [LDIPCU]); (b) the plurality of local weather-meteorological conditions measuring units [WMCMU]; and (c) the global data-information processing and communications unit [GDIPCU] 50.

Real-Time Processing and Analyzing the Set of Real-Time Regional Geographical Distribution Parametric Data-Information Profiles of the Contaminated Outdoor Air Particulate Matter Main Step (f) of the exemplary embodiment of the method 400 (FIG. 15B: 412) is of real-time processing and analyzing the set of real-time regional geographical distribution parametric data-information profiles of the contaminated outdoor air particulate matter, in relation to the data-information of the identified and classified ground sources of the contaminated outdoor air particulate matter, for determining at least one indication of needing to change operating conditions and contaminated air output of one or more of the ground sources, via the global data-information processing and communications unit.

This main step is implemented, for example, by real-time comparing specific features or/and elements of the set of real-time regional geographical distribution parametric data-information profiles of the contaminated outdoor air particulate matter, to the data-information of the identified and classified ground sources of the contaminated outdoor air particulate matter, as obtained via preceding main Step (a), namely, the chemical 'source (originator)' (emission, exhaustion, or output) inventory type data and information for the above stated exemplary categories of ground sources of the contaminated outdoor air particulate matter (Ground Sources (COAPM)), particularly, with respect to the threshold levels thereof which are suitable for human (internal or/and external) contact with (exposure to) the contaminated outdoor air particulate matter. Based on such comparisons, logical operations are performed, logical conclusions are arrived at, and logical decisions are made, via global data-information processing and communications unit [GDIPCU] 50, for determining at least one indication of needing to change operating conditions and contaminated air output of one or more of the ground sources of the contaminated outdoor air particulate matter (Ground Sources (COAPM)) which are located throughout the region (R-1) 20.

Real-Time Communicating the at Least One Indication to an Operator or/and Controller of Each of the One or More Ground Sources of the Contaminated Outdoor Air Particulate Matter Main Step (g) of the exemplary embodiment of the method 400 (FIG. 15B: 414) is of real-time communicating the at least one indication to an operator or/and controller of each of the one or more ground sources of the contaminated outdoor air particulate matter.

The real-time (wired or/and wireless) communicating the at least one indication [of needing to change operating conditions and contaminated air output of one or more of the ground sources of the contaminated outdoor air particulate matter (Ground Sources (COAPM))] to a (human or/and machine type) operator or/and controller of each of the one or more ground sources of the contaminated outdoor air particulate matter, can be effected in different ways. As a first example, communicating the at least one indication to an operator or/and controller of each of the one or more ground sources of the contaminated outdoor air particulate matter (Ground Sources (COAPM)) is effected via one or more of the local contaminated outdoor air particulate matter monitoring, sampling, and data-information processing stations [Local Station-i, for i=1 to 7 (32, 34, 36, 38, 40, 42, and 44)], for example, via the local data-information processing and communications units [LDIPCU], communicating with the operator or/and controller of each of the one or more ground sources of the contaminated outdoor air particulate matter (Ground Sources (COAPM)). Alternatively, as a second example, communicating the at least one indication to an operator or/and controller of each of the one or more ground sources of the contaminated outdoor air particulate matter (Ground Sources (COAPM)) is effected via global data-information processing and communications unit [GDIPCU] 50 communicating with the operator or/and controller of each of the one or more ground sources of the contaminated outdoor air particulate matter (Ground Sources (COAPM)). Alternatively, as a third example, communicating the at least one indication to an operator or/and controller of each of the one or more ground sources of the contaminated outdoor air particulate matter (Ground Sources (COAPM)) is effected via a combination of the preceding first and second examples.

Real-Time Changing, in a Controlled Manner, the Operating Conditions and the Contaminated Air Output of the One or More Ground Sources, by Each Operator or Controller, in Response to the at Least One Indication, Thereby Regulating the Contaminated Outdoor Air Particulate Matter Throughout the Region Main Step (h) of the exemplary embodiment of the method 400 (FIG. 15B: 416) is of real-time changing, in a controlled manner, the operating conditions and the contaminated air output of the one or more ground sources, by each operator or controller, in response to the at least one indication, thereby regulating the contaminated outdoor air particulate matter throughout the region.

The present invention, in exemplary embodiments thereof, as illustratively described and exemplified hereinabove, has several beneficial and advantageous aspects, characteristics, and features.

Exemplary embodiments of the present invention are particularly applicable to those fields and areas of technology which are based on, or/and, involve monitoring, profiling, maintaining, controlling, and providing public health information and advisories about, outdoor air quality of human populated regions. Exemplary embodiments are especially applicable to urban (city) regions wherein there co-exist large sized, densely located human populations with large numbers of densely located ground sources of contaminated outdoor air particulate matter, where exemplary categories of such ground sources are: (1) actively used and operative infrastructure type ground sources, such as industrial, commercial, business, public, private, and residential entities (building and building-like structures, especially, factories, manufacturing plants, power [coal and oil burning] plants, homes, food making and cooking establishments), and, vehicular roadways, bridges, and tunnels; (2) actively used and operative vehicular traffic type ground sources, such as automobiles, buses, trucks, motorbikes, and scooters; and (3) plant matter and ground surface type ground sources, such as trees, bushes, shrubs, plants, flowers, grass, and soil.

Exemplary embodiments of the present invention are particularly suitable for applications which are based on, or/and, involve monitoring, profiling, maintaining, operating and controlling, developing, and planning, infrastructure and vehicular traffic, of human populated regions, where such applications include the important objective of achieving and maintaining high quality levels of outdoor air of the human populated regions, which, in turn, contributes to achieving and maintaining high quality levels of public health, welfare, and activities throughout the human populated regions.

Exemplary embodiments of the present invention successfully address and overcome at least some of the various shortcomings or/and limitations, and widen the scope, of teachings relating to monitoring, parametric profiling, and regulating contaminated outdoor air particulate matter throughout a region. Exemplary embodiments of the present invention are readily commercially (industrially) applicable.

It is to be fully understood that certain aspects, characteristics, and features, of the present invention, which are illustratively described and presented in the context or format of a plurality of separate embodiments, may also be illustratively described and presented in any suitable combination or sub-combination in the context or format of a single embodiment. Conversely, various aspects, characteristics, and features, of the present invention, which are illustratively described and presented in combination or sub-combination in the context or format of a single embodiment, may also be illustratively described and presented in the context or format of a plurality of separate embodiments.

Although the present invention has been illustratively described and presented by way of specific embodiments, and examples thereof, it is evident that many alternatives, modifications, and variations, thereof, will be apparent to those skilled in the art. Accordingly, it is intended that all such alternatives, modifications, and variations, fall within, and are encompassed by, the scope of the appended claims.

All patents, patent applications, and publications, cited or referred to in this specification are herein incorporated in their entirety by reference into the specification, to the same extent as if each individual patent, patent application, or publication, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

REFERENCES

1. WIPO PCT Pat. Appl. Int'l. Pub. No. WO 2008/099407, published Aug. 21, 2008, of PCT Pat. Appl. No. IL2008/000205, filed Feb. 14, 2008, of same applicant/assignee as the present invention, entitled: "Hyper-spectral Imaging And Analysis Of A Sample Of Matter, And Preparing A Solution Or Suspension Therefrom".
2. WIPO PCT Pat. Appl. Int'l. Pub. No. WO 2007/0990540, published Sep. 7, 2007, of PCT Pat. Appl. No. IL2007/000268, filed Mar. 1, 2007, of same applicant/assignee as the present invention, entitled: "Processing And Analyzing Hyper-spectral Image Data And Information Via Dynamic Database Updating".
3. U.S. Pat. No. 7,411,682, to Moshe, of same applicant/assignee as the present invention, entitled: "Real Time High Speed High Resolution Hyper-spectral Imaging".
4. U.S. Pat. No. 6,697,510, to Moshe, of same applicant/assignee as the present invention, entitled: "Method For Generating Intra-particle Crystallographic Parameter Maps And Histograms Of A Chemically Pure Crystalline Particulate Substance".
5. U.S. Pat. No. 6,694,048, to Moshe, of same applicant/assignee as the present invention, entitled: "Method For Generating Intra-particle Morphological Concentration/Density Maps And Histograms Of A Chemically Pure Particulate Substance".
6. U.S. Pat. No. 6,438,261, to Moshe, et al., of same applicant/assignee as the present invention, entitled: "Method Of In-situ Focus-Fusion Multi-layer Spectral Imaging And Analysis".
7. U.S. Pat. No. 6,091,843, to Horesh, et al., of same applicant/assignee as the present invention, entitled: "Method Of Calibration And Real-time Analysis Of Particulates".
8. U.S. Pat. No. 5,880,830, to Schechter, of same applicant/assignee as the present invention, entitled: "Spectral Imaging Method For On-line Analysis Of Polycyclic Aromatic Hydrocarbons In Aerosols".

What is claimed is:

1. A method for real-time monitoring and parametric profiling contaminated outdoor air particulate matter (COAPM) throughout a region, via hyper-spectral imaging and analysis, said method being source-based for predicting composition and levels of contaminated outdoor air in the region, the method comprising:

A. at a global data-information processing and communications unit, identifying and classifying a plurality of ground sources of the COAPM throughout the region, said identifying and classifying including identifying a location of each of said plurality of ground sources throughout the region and classifying each of said plurality of ground sources according to one of a preselected set of types of ground sources, for generating data-information of the identified and classified ground sources of the COAPM;

for a first monitoring time, perform:

B. at each of a plurality of local COAPM monitoring, sampling, and data-information processing stations at separate locations throughout the region, simultaneously real-time sampling, and hyper-spectrally imaging and analyzing, the COAPM output from the plurality of ground sources, for generating a corresponding plurality of real-time local COAPM data-information packages each associated with a said separate location;

C. at each of a plurality of local weather-meteorological conditions measuring units, simultaneously real-time measuring outdoor weather-meteorological conditions, in a manner synchronized with said real-time sampling, imaging, and analyzing, for generating a corresponding plurality of real-time local outdoor weather-meteorological conditions data-information packages each associated with a said separate location; and D. at the global data-information processing and communications unit:
  (a) real-time processing and analyzing said real-time local COAPM data-information packages and said real-time local outdoor weather-meteorological conditions data-information packages, for real-time generating a set of real-time local geographical distribution parametric data-information profiles of the COAPM, indicating real-time local geographical distributions of qualitative or/and quantitative parameters of the COAPM associated with each said separate location; and
  (b) real-time processing and analyzing said set of real-time local geographical distribution parametric data-information profiles of the COAPM, for real-time generating a set of real-time regional geographical distribution parametric data-information profiles of the COAPM, indicating real-time regional geographical distributions of said qualitative or/and quantitative parameters of the COAPM throughout the region;

perform said B, C, and D for at least a second monitoring time; and

E. at the global data-information processing and communications unit, comparing and contrasting:
  said sets of real-time regional geographical distribution parametric data-information profiles of the COAPM generated at D(b) at each of said first and at least a second monitoring times, each of said sets containing data-information regarding COAPM associated with a respective one of the plurality of ground sources; with
  said data-information of the identified and classified ground sources of the COAPM, generated at (A),
  to quantify relative contributions of the different ground sources to the contaminated outdoor air and/or to infer the most likely ground sources contributing each type of COAPM to the contaminated outdoor air.

2. The method of claim 1, wherein said outdoor weather-meteorological conditions are selected from the group consisting of: (a) temperature; (b) humidity; (c) barometric pressure; (d) wind movement; (e) precipitation type, extent, and movement; and (f) clouds type, extent, and movement.

3. The method of claim 1, wherein said real-time measuring outdoor weather-meteorological conditions is performed using a weather-meteorological conditions measuring unit configured and operative for detecting, measuring, acquiring, collecting, processing, analyzing, and generating, local weather-meteorological conditions data and information of outdoor air, at each said separate location.

4. The method of claim 1, wherein weather-meteorological conditions data and information of said real-time local outdoor weather-meteorological conditions data-information package are detected, measured, and acquired, by at least one of the following outdoor air parametric measuring apparatuses: (i) an outdoor air temperature measuring apparatus; (ii) an outdoor air humidity measuring apparatus; (iii) an outdoor air barometric pressure measuring apparatus; (iv) an outdoor air wind movement measuring apparatus; (v) an outdoor air precipitation type, extent, and movement measuring apparatus; and (vi) an outdoor air cloud type, extent, and movement measuring apparatus.

5. The method of claim 1, wherein said real-time local outdoor weather-meteorological conditions data-information packages are sent from a local outdoor air weather-meteorological conditions measuring unit to a local data-information processing and communications unit which is operatively connected to and in communication with said global data-information processing and communications unit.

6. The method of claim 1, wherein said real-time processing and analyzing said real-time local outdoor air particulate matter data-information packages and said real-time local outdoor weather-meteorological conditions data-information packages, is performed using: (1) bottom-up, ground to air, based data-information processing and analyzing techniques and procedures, and (2) top-down, air to ground, based data-information techniques and procedures.

7. The method of claim 1, further including a data-information processing and analyzing technique based on accounting for, and using, continuously or periodically updated real-time local bottom-up, ground to air, type inventory data and information of said ground sources of the contaminated outdoor air particulate matter throughout the region.

8. The method of claim 1, further including a data-information processing and analyzing technique based on accounting for, and using, continuously or periodically updated real-time local bottom-up, ground to air, type inventory data and information of atmospheric gas content in outdoor air throughout the region.

9. The method of claim 1, further including correlating results obtained from using a data-information processing and analyzing technique based on accounting for, and using, continuously or periodically updated real-time local bottom-up, ground to air, type inventory data and information of ground sources of the contaminated outdoor air particulate matter throughout the region, with results obtained from using a data-information processing and analyzing technique based on accounting for, and using, continuously or periodically updated real-time local bottom-up, ground to air, type inventory data and information of atmospheric gas content in outdoor air throughout the region.

10. The method of claim 1, wherein said identifying and classifying ground sources of the COAPM includes identifying and classifying different types or kinds and quantities of the ground sources of the COAPM throughout the region.

11. Method according to claim 1, wherein said ground sources are selected from at least one of actively used and operative infrastructure type ground sources, actively used and operative vehicular traffic type ground sources, and plant matter and ground surface type ground sources.

12. Method according to claim 1, wherein said ground sources are one of directly and indirectly operable and controllable via at least one of human and machine type operators and human and machine type controllers.

13. Method according to claim 1, wherein said identifying and classifying ground sources includes real-time hyper-spectrally imaging and analyzing said ground sources of the contaminated outdoor air particulate matter, said hyper-spectrally imaging said ground sources generating ground source images having at least one of spectral 'fingerprint' and 'signature' pattern types of identification.

14. Method according to claim 6, wherein said bottom-up, ground to air, based data-information processing and analyzing techniques and procedures are source based data-information processing and analyzing techniques and procedures.

15. Method according to claim 1, wherein the plurality of ground sources is at least one of:
operable via at least one of a human and a machine operator; and
controllable via at least one of human and machine controller.

16. Method according to claim 1, wherein, real-time regional geographical distribution parametric data-information profiles of the COAPM include a mapping of the relative concentrations of COAPM throughout the region, for each of the identified and classified plurality of ground sources.

17. Method according to claim 1, wherein accuracy of said method is improved by performing said B, C, and D for at least one further monitoring time.

18. Method according to claim 1, wherein said hyper-spectrally imaging and analyzing the COAPM output from the plurality of ground sources includes optically supplying electromagnetic radiation to the COAPM and imaging the COAPM in a plurality of hyper-spectral images, via one or more fields of view.

19. Method according to claim 1, wherein said hyper-spectrally imaging and analyzing the COAPM output from the plurality of ground sources includes optically detecting affected energy or emission beam emitted by, and emerging from the COAPM, in the form of a plurality of whole images, and optically processing the whole images for generating optical forms of hyper-spectral images of the illuminated COAPM.

20. Method according to claim 1, wherein said hyper-spectral imaging includes producing a plurality of hyper-spectral images having spectral and spatial resolution on an order of less than about 30 nm.

21. Method according to claim 1, wherein said hyper-spectrally imaging is performed by a piezoelectric optical interferometer.

22. A method for real-time monitoring and regulating contaminated outdoor air particulate matter (COAPM) throughout a region, via hyper-spectral imaging and analysis, said method being source-based for predicting composition and levels of contaminated outdoor air in the region, the method comprising:
A. at a global data-information processing and communications unit, identifying and classifying the plurality of ground sources of the COAPM throughout the region, said identifying and classifying including identifying a location of each of said plurality of ground sources throughout the region and classifying each of said plurality of ground sources according to one of a preselected set of types of ground sources, for generating data-information of the identified and classified ground sources of the COAPM;

for a first monitoring time, perform:

B. at each of a plurality of local COAPM monitoring, sampling, and data-information processing stations at separate locations throughout the region, simultaneously real-time sampling, and hyper-spectrally imaging and analyzing, the COAPM output from the plurality of ground sources, for generating a corresponding plurality of real-time local COAPM data-information packages each associated with a said separate location;

C. at each of a plurality of local weather-meteorological conditions measuring units, simultaneously real-time measuring outdoor weather-meteorological conditions, in a manner synchronized with said real-time sampling, imaging, and analyzing, for generating a corresponding plurality of real-time local outdoor weather-meteorological conditions data-information packages each associated with a said separate location; and D. at the global data-information processing and communications unit:

(a) real-time processing and analyzing said real-time local COAPM data-information packages and said real-time local outdoor weather-meteorological conditions data-information packages, for real-time generating a set of real-time local geographical distribution parametric data-information profiles of the COAPM, indicating real-time local geographical distributions of qualitative or/and quantitative parameters of the COAPM associated with each said separate location; and (b) real-time processing and analyzing said set of real-time local geographical distribution parametric data-information profiles of the COAPM, for real-time generating a set of real-time regional geographical distribution parametric data-information profiles of the COAPM, indicating real-time regional geographical distributions of said qualitative or/and quantitative parameters of the COAPM throughout the region;

perform said B, C, and D for at least a second monitoring time;

E. at the global data-information processing and communications unit, comparing and contrasting:

said sets of real-time regional geographical distribution parametric data-information profiles of the COAPM generated at D(b) at each of said first and at least a second monitoring times, each of said sets containing data-information regarding COAPM associated with a respective one of the plurality of ground sources; with said data-information of the identified and classified ground sources of the COAPM, generated at (A), to quantify relative contributions of the different ground sources to the contaminated outdoor air and/or to infer the most likely ground sources contributing each type of COAPM to the contaminated outdoor air; and F. at the global data-information processing and communications unit:

(a) real-time processing and analyzing said set of real-time regional geographical distribution parametric data-information profiles of the COAPM, in relation to said data-information of said identified and classified ground sources of the COAPM, for determining at least one indication of needing to change operating conditions and contaminated air output of one or more of said ground sources;

(b) using communications equipment, real-time communicating said at least one indication of needing to change to an operator or controller of each of said one or more ground sources of the COAPM; and (c) real-time changing, in a controlled manner, said operating conditions and said contaminated air output of said one or more ground sources, by each said operator or controller, in response to said at least one indication of needing to change, thereby regulating the COAPM throughout the region.

23. The method of claim 22, wherein said outdoor weather-meteorological conditions are selected from the group consisting of: (a) temperature; (b) humidity; (c) barometric pressure; (d) wind movement; (e) precipitation type, extent, and movement; and (f) clouds type, extent, and movement.

24. The method of claim 22, wherein said real-time measuring outdoor weather-meteorological conditions is performed using a weather-meteorological conditions measuring unit configured and operative for detecting, measuring, acquiring, collecting, processing, analyzing, and generating, local weather-meteorological conditions data and information of outdoor air, at each said separate location.

25. The method of claim 22, wherein weather-meteorological conditions data and information of said real-time local outdoor weather-meteorological conditions data-information package are detected, measured, and acquired, by at least one of the following outdoor air parametric measuring apparatuses: (i) an outdoor air temperature measuring apparatus; (ii) an outdoor air humidity measuring apparatus; (iii) an outdoor air barometric pressure measuring apparatus; (iv) an outdoor air wind movement measuring apparatus; (v) an outdoor air precipitation type, extent, and movement measuring apparatus; and (vi) an outdoor air cloud type, extent, and movement measuring apparatus.

26. The method of claim 22, wherein said real-time local outdoor weather-meteorological conditions data-information packages are sent from a local outdoor air weather-meteorological conditions measuring unit to a local data-information processing and communications unit which is operatively connected to and in communication with said global data-information processing and communications unit.

27. The method of claim 22, wherein said real-time processing and analyzing said real-time local outdoor air particulate matter data-information packages and said real-time local outdoor weather-meteorological conditions data-information packages, is performed using: (1) bottom-up, ground to air, based data-information processing and analyzing techniques and procedures, and (2) top-down, air to ground, based data-information techniques and procedures.

28. The method of claim 22, further including a data-information processing and analyzing technique based on accounting for, and using, continuously or periodically updated real-time local bottom-up, ground to air, type inventory data and information of ground sources of the contaminated outdoor air particulate matter throughout the region.

29. The method of claim 22, further including a data-information processing and analyzing technique based on accounting for, and using, continuously or periodically updated real-time local bottom-up, ground to air, type inventory data and information of atmospheric gas content in outdoor air throughout the region.

30. The method of claim 22, further including correlating results obtained from using a data-information processing and analyzing technique based on accounting for, and using, continuously or periodically updated real-time local bottom-up, ground to air, type inventory data and information of ground sources of the contaminated outdoor air particulate matter throughout the region, with results obtained from using a data-information processing and analyzing technique based on accounting for, and using, continuously or periodically updated real-time local bottom-up, ground to air, type inventory data and information of atmospheric gas content in outdoor air throughout the region.

31. A system for real-time monitoring and parametric profiling contaminated outdoor air particulate matter (COAPM) throughout a region, via hyper-spectral imaging and analysis, said system configured to be source-based for predicting composition and levels of contaminated outdoor air in the region, the system comprising:

A. a global data-information processing and communications unit, configured for: (a) identifying and classifying the plurality of ground sources of the COAPM throughout the region, said identifying and classifying including identifying a location of each of said plurality of ground sources throughout the region and classifying each of said plurality of ground sources according to one of a preselected set of types of ground sources, for generating data-information of identified and classified ground sources of the COAPM;

B. a plurality of local COAPM monitoring, sampling, and data-information processing stations, configured for separately and simultaneously operating at a corresponding plurality of separate locations throughout the region, including real-time sampling, and hyper-spectrally imaging and analyzing the COAPM output from the plurality of ground sources, for generating a corresponding plurality of real-time local COAPM data-information packages each associated with a said separate location;

C. a plurality of local weather-meteorological conditions measuring units, configured for separately and simultaneously operating at said plurality of separate locations, including real-time measuring weather-meteorological conditions, in a manner synchronized with said real-time sampling, imaging, and analyzing, for generating a corresponding plurality of real-time local outdoor weather-meteorological conditions data-information packages each associated with a said separate location; and wherein said global data-information processing and communications unit is further configured for:

D. (b) real-time processing and analyzing said real-time local COAPM data-information packages and said real-time local outdoor weather-meteorological conditions data-information packages, for real-time generating a set of real-time local geographical distribution parametric data-information profiles of the COAPM, indicating real-time local geographical distributions of qualitative or/and quantitative parameters of the COAPM associated with each said separate location; and (c) real-time processing and analyzing said set of real-time local geographical distribution parametric data-information profiles of the COAPM, for real-time generating a set of real-time regional geographical distribution parametric data-information profiles of the COAPM, indicating real-time regional geographical distributions of said qualitative or/and quantitative parameters of the COAPM throughout the region;

wherein said plurality of local COAPM monitoring, sampling and data-information processing stations; said plurality of local weather-meteorological conditions measuring units; and said global data-information processing and communications unit are configured to perform said respective operations in B, C, and D, for at least two monitoring times; and E. wherein said global data-information processing and communications unit is further configured for comparing and contrasting:

said sets of real-time regional geographical distribution parametric data-information profiles of the COAPM generated at D(b) at each of said at least two monitoring times, each of said sets containing data-information regarding COAPM associated with a respective one of the plurality of ground sources; with said data-information of the identified and classified ground sources of the COAPM, generated at (A), to quantify relative contributions of the different ground sources to the contaminated outdoor air and/or to infer the most likely ground sources contributing each type of COAPM to the contaminated outdoor air.

32. The system of claim 31, wherein said outdoor weather-meteorological conditions are selected from the group consisting of: (a) temperature; (b) humidity; (c) barometric pressure; (d) wind movement; (e) precipitation type, extent, and movement; and (f) clouds type, extent, and movement.

33. The system of claim 31, wherein each said local weather-meteorological conditions measuring unit includes at least one of the following outdoor air parametric measuring apparatuses: (i) an outdoor air temperature measuring apparatus; (ii) an outdoor air humidity measuring apparatus; (iii) an outdoor air barometric pressure measuring apparatus; (iv) an outdoor air wind movement measuring apparatus; (v) an outdoor air precipitation type, extent, and movement measuring apparatus; and (vi) an outdoor air cloud type, extent, and movement measuring apparatus.

34. The system of claim 31, wherein said real-time local outdoor weather-meteorological conditions data-information packages are sent from said local weather-meteorological conditions measuring unit to a local data-information processing and communications unit which is operatively connected to and in communication with said global data-information processing and communications unit.

35. The system of claim 31, wherein said global data-information processing and communications unit is further configured for said real-time processing and analyzing said real-time local outdoor air particulate matter data-information packages and said real-time local outdoor weather-meteorological conditions data-information packages, by using: (1) bottom-up, ground to air, based data-information processing and analyzing techniques and procedures, and (2) top-down, air to ground, based data-information techniques and procedures.

36. The system of claim 31, wherein said global data-information processing and communications unit is further configured for including a data-information processing and analyzing technique based on accounting for, and using, continuously or periodically updated real-time local bottom-up, ground to air, type inventory data and information of ground sources of the contaminated outdoor air particulate matter throughout the region.

37. The system of claim 31, wherein said global data-information processing and communications unit is further configured for including a data-information processing and analyzing technique based on accounting for, and using, continuously or periodically updated real-time local bottom-up, ground to air, type inventory data and information of atmospheric gas content in outdoor air throughout the region.

38. The system of claim 31, wherein said global data-information processing and communications unit is further configured for correlating results obtained from using a data-information processing and analyzing technique based on accounting for, and using, continuously or periodically updated real-time local bottom-up, ground to air, type inventory data and information of ground sources of the contaminated outdoor air particulate matter throughout the region, with results obtained from using a data-information processing and analyzing technique based on accounting for, and using, continuously or periodically updated real-time local bottom-up, ground to air, type inventory data and information of atmospheric gas content in outdoor air throughout the region.

39. A system for real-time monitoring and regulating contaminated outdoor air particulate matter (COAPM) throughout a region, via hyper-spectral imaging and analysis, said system configured to be source-based for predicting composition and levels of contaminated outdoor air in the region, the system comprising:

A. a global data-information processing and communications unit, configured for:
  (a) identifying and classifying the plurality of ground sources of the COAPM throughout the region, said identifying and classifying including identifying a location of each of said plurality of ground sources throughout the region and classifying each of said plurality of ground sources according to one of a preselected set of types of ground sources, for generating data-information of identified and classified ground sources of the COAPM;

B. a plurality of local COAPM monitoring, sampling, and data-information processing stations, configured for separately and simultaneously operating at a corresponding plurality of separate locations throughout the region, including real-time sampling, and hyper-spectrally imaging and analyzing the COAPM output from the plurality of ground sources, for generating a corresponding plurality of real-time local COAPM data-information packages each associated with a said separate location;

C. a plurality of local weather-meteorological conditions measuring units, configured for separately and simultaneously operating at said plurality of separate locations, including real-time measuring weather-meteorological conditions, in a manner synchronized with said real-time sampling, imaging, and analyzing, for generating a corresponding plurality of real-time local outdoor weather-meteorological conditions data-information packages each associated with a said separate location; and wherein said global data-information processing and communications unit is further configured for:

D. (b) real-time processing and analyzing said real-time local COAPM data-information packages and said real-time local outdoor weather-meteorological conditions data-information packages, for real-time generating a set of real-time local geographical distribution parametric data-information profiles of the COAPM, indicating real-time local geographical distributions of qualitative or/and quantitative parameters of the COAPM associated with each said separate location; and (c) real-time processing and analyzing said set of real-time local geographical distribution parametric data-information profiles of the COAPM, for real-time generating a set of real-time regional geographical distribution parametric data-information profiles of the COAPM, indicating real-time regional geographical distributions of said qualitative or/and quantitative parameters of the COAPM throughout the region;

wherein said plurality of local COAPM monitoring, sampling and data-information processing stations; said plurality of local weather-meteorological conditions measuring units; and said global data-information processing and communications unit are configured to perform said respective operations in B, C, and D, for at least two monitoring times; and wherein said global data-information processing and communications unit is further configured for:
(d) comparing and contrasting:

said sets of real-time regional geographical distribution parametric data-information profiles of the COAPM generated at D(b) at each of said at least two monitoring times, each of said sets containing data-information regarding COAPM associated with a respective one of the plurality of ground sources; with said data-information of the identified and classified ground sources of the COAPM, generated at (A), to quantify relative contributions of the different ground sources to the contaminated outdoor air and/or to infer the most likely ground sources contributing each type of COAPM to the contaminated outdoor air; and (e) real-time processing and analyzing said set of real-time regional geographical distribution parametric data-information profiles of the COAPM, in relation to said data-information of said identified and classified ground sources of the COAPM, for determining at least one indication of needing to change operating conditions and contaminated air output of one or more of said ground sources; and E. communications equipment, configured for real-time communicating said at least one indication of needing to change to an operator or controller of each of said one or more said ground sources of the COAPM, in order for each said operator or controller to real-time change, in a controlled manner, said operating conditions and contaminated air output thereof, in response to said at least one indication of needing to change, thereby regulating the COAPM throughout the region.

40. The system of claim 39, wherein said outdoor weather-meteorological conditions are selected from the group consisting of: (a) temperature; (b) humidity; (c) barometric pressure; (d) wind movement; (e) precipitation type, extent, and movement; and (f) clouds type, extent, and movement.

41. The system of claim 39, wherein each said local weather-meteorological conditions measuring unit includes at least one of the following outdoor air parametric measuring apparatuses: (i) an outdoor air temperature measuring apparatus; (ii) an outdoor air humidity measuring apparatus; (iii) an outdoor air barometric pressure measuring apparatus; (iv) an outdoor air wind movement measuring apparatus; (v) an outdoor air precipitation type, extent, and movement measuring apparatus; and (vi) an outdoor air cloud type, extent, and movement measuring apparatus.

42. The system of claim 39, wherein said real-time local outdoor weather-meteorological conditions data-information packages are sent from said local weather-meteorological conditions measuring unit to a local data-information processing and communications unit which is operatively connected to and in communication with said global data-information processing and communications unit.

43. The system of claim 39, wherein said global data-information processing and communications unit is further configured for said real-time processing and analyzing said real-time local outdoor air particulate matter data-information packages and said real-time local outdoor weather-meteorological conditions data-information packages, by using: (1) bottom-up, ground to air, based data-information processing and analyzing techniques and procedures, and (2) top-down, air to ground, based data-information techniques and procedures.

44. The system of claim 39, wherein said global data-information processing and communications unit is further configured for including a data-information processing and analyzing technique based on accounting for, and using, continuously or periodically updated real-time local bottom-up, ground to air, type inventory data and information of ground sources of the contaminated outdoor air particulate matter throughout the region.

45. The system of claim 39, wherein said global data-information processing and communications unit is further configured for including a data-information processing and analyzing technique based on accounting for, and using, continuously or periodically updated real-time local bottom-up, ground to air, type inventory data and information of atmospheric gas content in outdoor air throughout the region.

46. The system of claim 39, wherein said global data-information processing and communications unit is further configured for correlating results obtained from using a data-information processing and analyzing technique based on accounting for, and using, continuously or periodically updated real-time local bottom-up, ground to air, type inventory data and information of ground sources of the contaminated outdoor air particulate matter throughout the region, with results obtained from using a data-information processing and analyzing technique based on accounting for, and using, continuously or periodically updated real-time local bottom-up, ground to air, type inventory data and information of atmospheric gas content in outdoor air throughout the region.

* * * * *